US010494397B2

(12) United States Patent
Bonorden et al.

(10) Patent No.: US 10,494,397 B2
(45) Date of Patent: Dec. 3, 2019

(54) REBAUDIOSIDE ANALOGS

(71) Applicant: PepsiCo, Inc., Purchase, NY (US)

(72) Inventors: William Bonorden, Brewster, NY (US); Shawn Erickson, Leonia, NJ (US); Christophe Galopin, Rye Brook, NY (US); Laura Nattress, Tarrytown, NY (US)

(73) Assignee: pepsico, inc., Purchase, NY (US)

( * ) Notice: Subject to any disclaimer, the term of this patent is extended or adjusted under 35 U.S.C. 154(b) by 205 days.

(21) Appl. No.: 15/211,058

(22) Filed: Jul. 15, 2016

(65) Prior Publication Data

US 2018/0016291 A1 Jan. 18, 2018

(51) Int. Cl.
C07H 15/24 (2006.01)
A23L 27/30 (2016.01)
A23L 2/60 (2006.01)

(52) U.S. Cl.
CPC ............... C07H 15/24 (2013.01); A23L 2/60 (2013.01); A23L 27/36 (2016.08); A23V 2002/00 (2013.01)

(58) Field of Classification Search
None
See application file for complete search history.

(56) References Cited

U.S. PATENT DOCUMENTS

| 4,353,889 | A | * | 10/1982 | DuBois | A23L 27/30 424/48 |
|---|---|---|---|---|---|
| 4,830,862 | A | | 5/1989 | Braun et al. | |
| 4,925,686 | A | | 5/1990 | Kastin | |
| 8,877,922 | B2 | | 11/2014 | Tachdjian et al. | |
| 9,215,889 | B2 | | 12/2015 | Morita et al. | |
| 2008/0064753 | A1 | | 3/2008 | Palladino et al. | |
| 2014/0093630 | A1 | | 4/2014 | Shigemura et al. | |
| 2014/0094453 | A1 | | 4/2014 | Tachdjian et al. | |
| 2014/0271996 | A1 | | 9/2014 | Prakash et al. | |
| 2014/0272068 | A1 | | 9/2014 | Prakash et al. | |
| 2014/0296499 | A1 | | 10/2014 | Chen et al. | |
| 2014/0343262 | A1 | | 11/2014 | Prakash et al. | |
| 2014/0357588 | A1 | | 12/2014 | Markosyan et al. | |

FOREIGN PATENT DOCUMENTS

| WO | WO 2009/038978 A2 | 3/2009 | |
|---|---|---|---|
| WO | WO-2012125991 A2 * | 9/2012 | ............ C07H 1/00 |
| WO | WO 2016/040577 A1 | 3/2016 | |

OTHER PUBLICATIONS

CN 104341470 A, Feb. 2, 2015, machine translation.*
International Search Report dated Nov. 9, 2017 for International Application No. PCT/US2017/041860, 4 pages.
Wölwer-Rieck, Ursula, "*The Leaves of Stevia rebaudiana (Bertoni), Their Constituents and the Analyses Thereof: A Review*," Journal of Agricultural and Food Chemistry, 2012, vol. 60, American Chemical Society, pp. 886-895.
Al'Fonsov, V.A., et al., "*Chemistry and Structure of Diterpenoids: X.[1] Isosteviol Amides*," Russian Journal of General Chemistry, vol. 75, No. 2, 2005, pp. 248-253. Translated from Zhurnal Obshchei Khimii, vol. 75, No. 2, 2005, pp. 276-281.
Chaturvedula, Venkata Sai Prakash, et al., "*A New Diterpene Glycoside from Stevia rebaudiana*," Molecules, 2011, 16, pp. 2937-2943, www.mdpi.com/journal/molecules.

* cited by examiner

*Primary Examiner* — Layla D Berry
(74) *Attorney, Agent, or Firm* — Sterne, Kessler, Goldstein & Fox P.L.L.C.

(57) ABSTRACT

The present disclosure provides novel compounds that are steviol derivatives. The compounds generally can be characterized by a structure according to Formula I:

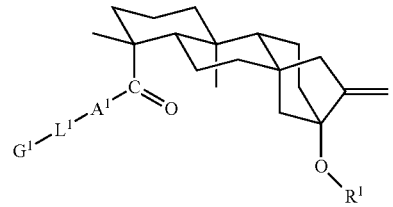

Formula I wherein $R^1$, $A^1$, $L^1$, and $G^1$ are described herein. Also provided are sweetener compositions comprising the compound described herein either as a sweetener or a sweetener enhancer. Additionally, the compound or the sweetener composition can be included in a product such as a beverage product or a food product, which can reduce the amount of sweetener in the product required to achieve the same sweetness level in an otherwise identical product not including the compound or the sweetener composition.

23 Claims, 18 Drawing Sheets

REBAUDIOSIDE ANALOGS

FIELD OF DISCLOSURE

The present disclosure is generally directed to steviol derivatives that may be used in a product, for example, a beverage product or a food product, to modify the product's sweetness, taste, and/or flavor.

BACKGROUND

Naturally occurring steviol glycosides are sweet-tasting compounds extracted from the *stevia* plant (*Stevia rebaudiana* Bertoni). Typically, *stevia* plant extract includes stevioside (4-13% dry weight), steviolbioside (trace), the rebaudiosides, including rebaudioside ("Reb") A (1-6%), rebaudioside B (trace), rebaudioside C (1-2%), rebaudioside D (trace), and rebaudioside E (trace), and dulcoside A (0.4-0.7%). Many steviol glycosides are potent, non-nutritive sweeteners. For example, Rebaudioside A has a sweetness about 200 to 300 times the sweetness of sucrose.

The food and beverage industry has become interested in steviol glycosides in the pursuit of alternative sweeteners. However, replacing nutritive sweeteners with known potent non-nutritive sweeteners is difficult due to slow on-set or off-tastes associated with these sweeteners, including, for example, bitter, licorice, or lingering aftertastes. Thus, there remains a need for high-potency sweeteners that better mimic sugar's taste profile.

BRIEF SUMMARY

In various embodiments, the present disclosure provides novel compounds that are steviol derivatives. In some embodiments, the compound can be characterized as having a structure according to Formula I:

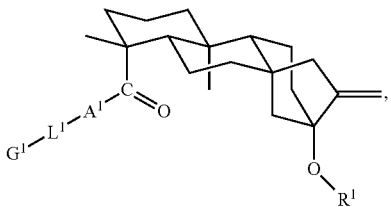

Formula I wherein $R^1$, $A^1$, $L^1$, and $G^1$ are described herein. In some embodiments, $R^1$ is 2,3-bis(1-β-D-glucopyranosyl)-1-β-D-glucopyranosyl. In some embodiments, $A^1$-$L^1$-$G^1$ represents a sugar residue, for example, a monosaccharide pyranose. In some embodiments, $A^1$-$L^1$-$G^1$ represents a sugar alcohol residue, for example, a residue of glycerol, erythritol, xylitol, sorbitol, and mannitol. In some embodiments, $A^1$-$L^1$-$G^1$ represents an amino acid residue, for example, an amino acid residue of glycine, alanine, phenylalanine, or valine. In some embodiments, $A^1$-$L^1$-$G^1$ represents an alkoxyl group, which forms an ester with the carbonyl group it attached to. In some embodiments, $A^1$-$L^1$-$G^1$ represents a residue of a dipeptide, a tripeptide, a disaccharide, a trisaccharide, a lactate or ester, or an amino ester. In any of the embodiments described herein, the compound of Formula I can be in the form of a salt.

Certain embodiments of the present disclosure are directed to a sweetener composition comprising the compound described herein either as a sweetener or a sweetener enhancer.

Certain embodiments of the present disclosure are directed to a product comprising the compound or the sweetener composition described herein. In some embodiments, the product is a beverage product. In some embodiments, the product is a food product.

Certain embodiments of the present disclosure are directed to a method of reducing the amount of sweetener in a product, for example, a food product or a beverage product. In some embodiments, the method comprises replacing at least a portion of the sweetener in the food or beverage product with the compound described herein.

BRIEF DESCRIPTION OF THE DRAWINGS

The foregoing summary, as well as the following detailed description of the embodiments, will be better understood when read in conjunction with the appended figures. For the purpose of illustration, the figures may describe the use of specific embodiments. It should be understood, however, that the compounds, formulations and compositions described herein are not limited to the precise embodiments discussed or described in the figures.

DETAILED DESCRIPTION

Figure 1:
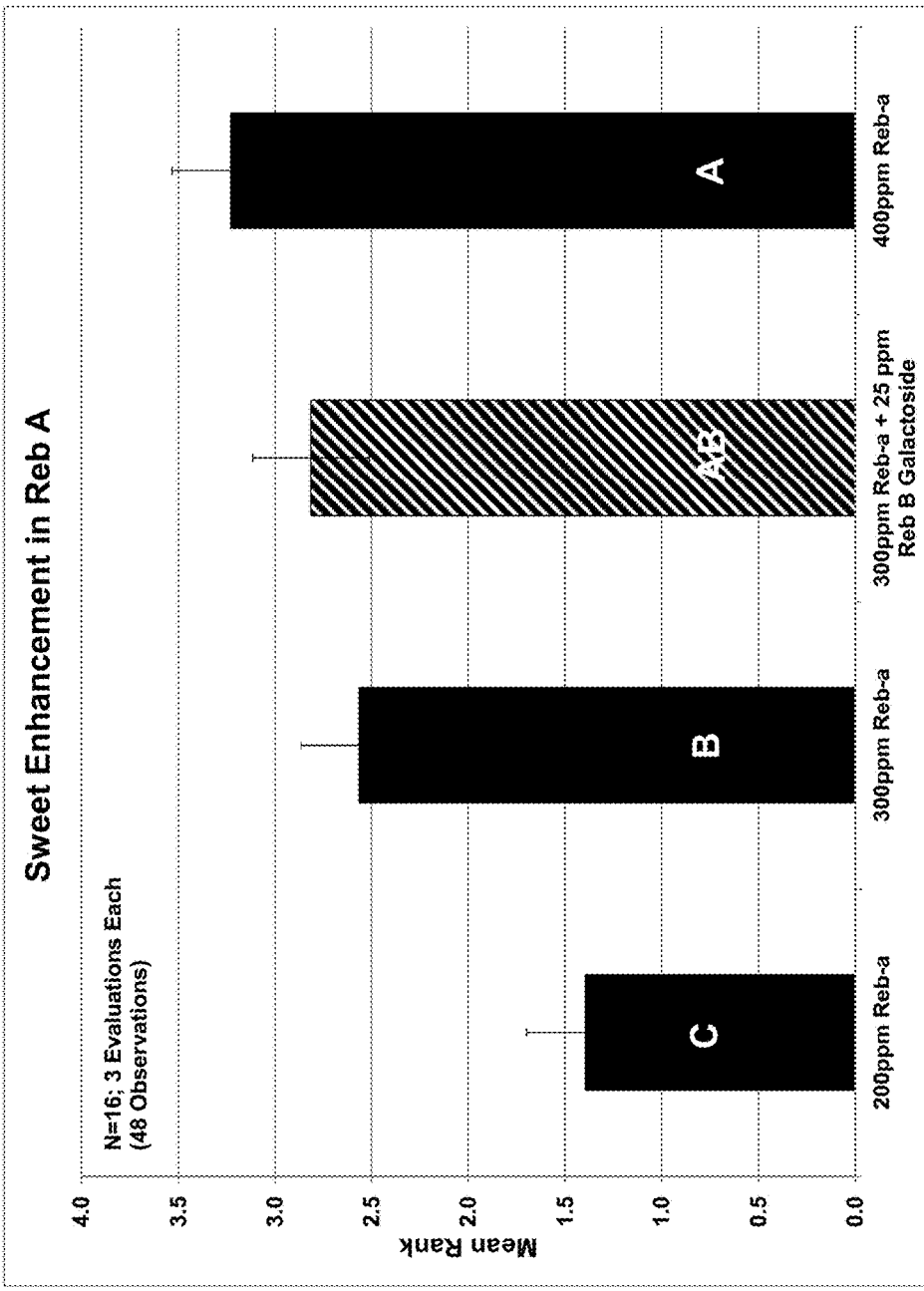
FIG. 1 depicts bar graphs showing that adding 25 ppm of Reb B galactoside to Rebaudioside A enhances the sweetness of the Rebaudioside A.

Various examples and embodiments of the inventive subject matter disclosed here are possible and will be apparent to the person of ordinary skill in the art, given the benefit of this disclosure. In this disclosure reference to "some embodiments," "certain embodiments," "certain exemplary embodiments" and similar phrases each means that those embodiments are non-limiting examples of the inventive subject matter, and there are alternative embodiments which are not excluded.

Unless otherwise indicated or unless otherwise clear from the context in which it is described, alternative and optional elements or features in any of the disclosed embodiments and examples are interchangeable with each other. That is, an element described in one embodiment or example should be understood to be interchangeable or substitutable for one or more corresponding but different elements in another described example or embodiment and, likewise, an optional feature of one embodiment or example may optionally also be used in other embodiments and examples. More generally, the elements and features of any disclosed example or embodiment should be understood to be disclosed generally for use with other aspects and other examples and embodiments. A reference to a component or ingredient being operative or configured to perform one or more specified functions, tasks and/or operations or the like, is intended to mean that it can perform such function(s), task(s), and/or operation(s) in at least certain embodiments, and may well be able to perform also one or more other functions, tasks, and/or operations.

The articles "a," "an," and "the" are used herein to refer to one or to more than one (i.e., to at least one) of the grammatical object of the article. By way of example, "an element" means one element or more than one element.

The word "comprising" is used in a manner consistent with its open-ended meaning, that is, to mean that a given product or process can optionally also have additional features or elements beyond those expressly described. It is understood that wherever embodiments are described with the language "comprising," otherwise analogous embodiments described in terms of "consisting of" and/or "consisting essentially of" are also provided.

As used herein, the term "about" means ±10% of the noted value. By way of example only, a composition comprising "about 30 weight percent" of a compound could include from 27 weight percent of the compound up to and including 33 weight percent of the compound.

The terms "beverage concentrate," "concentrate," and "syrup" are used interchangeably throughout this disclosure and refer to an aqueous sweetener composition suitable for use in beverage preparation. Exemplary embodiments are described elsewhere in this disclosure.

As used herein, the term "Brix" means the sugar content of an aqueous solution (w/w). By way of example only, a solution that is 1 degree Brix contains 1 g of sucrose in 100 grams of solution, while a solution that is 5 degrees Brix contains 5 g sucrose in 100 g solution.

The term "sweetness recognition threshold concentration," as generally used herein, is the lowest known concentration of a given sweetener or combination of sweeteners that is perceivable by the human sense of taste, typically around about 1.5% sucrose equivalence.

As used herein, "taste" refers to a combination of sweetness perception, temporal effects of sweetness perception, i.e., on-set and duration, off-tastes, e.g. bitterness and metallic taste, residual perception (aftertaste), and tactile perception, e.g. body and thickness.

The term "nutritive sweetener" refers generally to sweeteners which provide significant caloric content in typical usage amounts, e.g., more than about 5 calories per 8 oz. serving of a beverage.

As used herein, the term "non-nutritive sweetener" refers to all sweeteners other than nutritive sweeteners.

As used herein, a "potent sweetener" means a sweetener which is at least twice as sweet as sugar, i.e. a sweetener which on a weight basis requires no more than half the weight of sugar to achieve an equivalent sweetness. For example, a potent sweetener may require less than one-half the weight of sugar to achieve an equivalent sweetness in a beverage sweetened to a level of 10 degrees Brix with sugar. Potent sweeteners include both nutritive (e.g., Lo Han Guo juice concentrate) and non-nutritive sweeteners (e.g., typically, Lo Han Guo powder). In addition, potent sweeteners include both natural potent sweeteners (e.g., steviol glycosides, Lo Han Guo, etc.) and artificial potent sweeteners (e.g., neotame, etc.).

As used herein, the term "alkyl" as used by itself or as part of another group refers to unsubstituted straight- or branched-chain aliphatic hydrocarbons containing from one to six carbon atoms, i.e., $C_{1-6}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-6}$ alkyl. In another embodiment, the alkyl is a $C_{1-4}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-6}$ alkyl groups include methyl, ethyl, propyl, isopropyl, butyl, sec-butyl, tert-butyl, iso-butyl, 3-pentyl, and hexyl. Non-limiting exemplary $C_{1-4}$ alkyl groups include methyl, ethyl, propyl, isopropyl, butyl, sec-butyl, tert-butyl, and iso-butyl.

As used herein, the term "alkylene linker" used by itself or as part of another group refers to a straight chain alkyl group having the formula $—(CH_2)_m—$. In one embodiment, the alkylene linker is a $C_{1-12}$ straight chain alkyl linker, i.e., m is up to 12. In one embodiment, the alkylene linker is a straight chain $C_{1-10}$ alkyl linker, i.e., m is up to 10. In one embodiment, the alkylene linker is a straight chain $C_{1-8}$ alkyl linker, i.e., m is up to 8. In one embodiment, the alkylene linker is a straight chain $C_{1-6}$ alkyl linker, i.e., m is up to 6. In another embodiment, the alkylene linker is a straight chain $C_{1-4}$ alkyl, i.e., m is up to 4. Non-limiting exemplary alkylene linkers include:

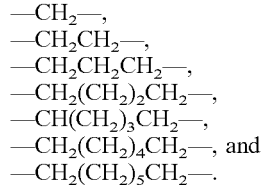

As used herein, the term "cycloalkyl" used by itself or as part of another group refers to saturated and partially unsaturated (i.e., containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

As used herein, the term "aryl" used by itself or as part of another group refers to a monocyclic or bicyclic aromatic ring system having from six to ten carbon atoms (i.e., $C_6$-$C_{10}$ aryl). Non-limiting exemplary aryl groups include phenyl (abbreviated as "Ph"), naphthyl, indenyl, and azulenyl, groups. In one embodiment, the aryl group is chosen from phenyl or naphthyl.

As used herein, the term "heteroaryl" refers to monocyclic and bicyclic aryls having 5 to 10 ring atoms (i.e., $C_5$-$C_{10}$ heteroaryl), wherein at least one aryl carbon atom is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. The term "heteroaryl" is also meant to include possible N-oxides. A non-limiting exemplary N-oxide is pyridyl N-oxide. In one embodiment, the heteroaryl is a 5- or 6-membered heteroaryl. In one embodiment, the heteroaryl is a 5-membered heteroaryl. Non-limiting exemplary 5-membered heteroaryl groups include thienyl, furyl, pyrrolyl, oxazolyl, pyrazolyl, imidazolyl, thiazolyl, isothiazolyl, and isoxazolyl. In another embodiment, the heteroaryl is a 6-membered heteroaryl. Non-limiting exemplary 6-membered heteroaryl groups include pyridyl, pyrazinyl, pyrimidinyl, and pyridazinyl.

As used herein, the term "heterocycle" or "heterocyclic" as used by itself or as part of another group refers to saturated and partially unsaturated (e.g., containing one or two double bonds) cyclic groups containing one, two, or three rings having from three to ten ring members (i.e., a 3- to 10-membered heterocyclo) wherein at least one atom of one of the rings is a heteroatom. Each heteroatom is independently selected from the group consisting of oxygen, sulfur, including sulfoxide and sulfone, and/or nitrogen atoms, which can be oxidized or quaternized. The term "heterocyclic" is meant to include groups wherein a ring —$CH_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclic" is also meant to include groups having fused optionally substituted aryl groups, e.g., indolinyl, chroman-4-yl. Non-limiting exemplary heterocyclic groups include thietanyl, tetrahydropyranyl and tetrahydrofuranyl.

As used herein, the term "pyranosyl" refers to a residue of a pyranose compound. For example, a "pyranosyl" group can have a structure according to the following formula:

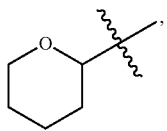 [SMILES: *C1CCCCO1]

wherein the tetrahydropyran ring can have 1-6 substituents in accordance with the pyranose compound. Examples of "pyranosyl" groups include α-mannopyranosyl, β-mannopyranosyl, α-glucopyranosyl, β-glucopyranosyl, α-xylopyranosyl, β-xylopyranosyl, α-galactopyranosyl, β-galactopyranosyl, α-rhamnopyranosyl, and β-rhamnopyranosyl etc. In some embodiments, a "pyranosyl" group can be selected from the group consisting of:

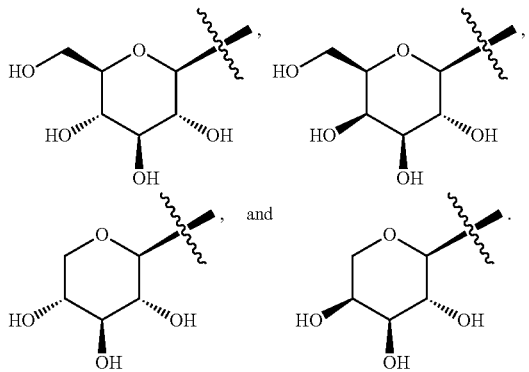

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer.

The term "diastereomeric excess" or "de" refers to a measure for how much of one diastereomer is present compared to the other and is defined by analogy to enantiomeric excess. Thus, for a mixture of diastereomers, D1 and D2, the percent diastereomeric excess is defined as $|D1-D2|*100$, where D1 and D2 are the respective mole or weight fractions of diastereomers in a mixture such that $D1+D2=1$.

The determination of diastereomeric and/or enantiomeric excess is possible using a variety of analytical techniques, including NMR spectroscopy, chiral column chromatography, and/or optical polarimetry according to routine protocols will be familiar to those of ordinary skill in the art.

As used herein, unless otherwise specified, the term "added," "combined," and terms of similar character mean that the ingredients or components referred to (e.g., one or more sweeteners, sweetness enhancers, etc.) are combined in any manner and in any order, with or without stirring.

Rebaudioside Analogs

In various embodiments, the present disclosure provides novel high-potency sweeteners that can be prepared from Steviol, the structure of which is shown below.

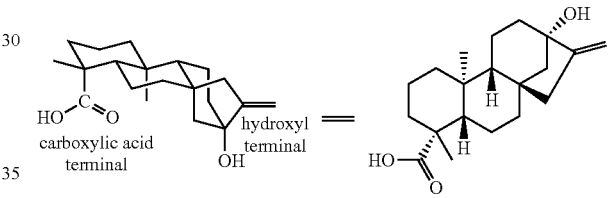

Structural of Steviol

In some embodiments, the compound described herein can incorporate a structural unit from a sweetener and/or sweetener enhancer, or a flavor modifying molecule through the carboxylic acid terminal of steviol. The sweetener and/or sweetener enhancer, or flavor modifying molecule can be, for example, a sugar, such as a monosaccharide pyranose, disaccharides, trisaccharides, or tetrasaccharides, a sugar alcohol, an amino acid, an amino ester, a dipeptide, or a tripeptide. In some embodiments, the compound described herein can incorporate a sugar unit through the hydroxyl terminal of steviol. For example, the sugar unit can be a monosaccharide pyranose, a disaccharide, a trisaccharide, or a tetrasaccharide. In some embodiment, the sugar unit attached to the hydroxyl terminal of steviol can be the same corresponding sugar unit as naturally occurring in rebaudiosides. In some embodiments, the compound described herein is not naturally occurring. For example, in some embodiments, the compound described herein is not rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, or rebaudioside O. In some embodiments, the compound described herein is chemically synthesized from a rebaudioside, for example, rebaudioside B.

In any of the embodiments described herein, the compound can be a substantially purified compound, for example, having a purity of at least 80%, at least 85%, at least 90%, at least 95%, or at least 99% by weight. In some embodiments, the compound can be a substantially purified compound having a purity of at least 80%, at least 85%, at least 90%, at least 95%, or at least 99% by HPLC measurement, for example, using the method described in the Examples section. In some embodiments, the compound can be a substantially purified compound having a purity by weight of about 80%, about 85%, about 90%, about 95%, about 99%, or any ranges between the specified values. In some embodiments, the compound can be a substantially purified compound having a purity by HPLC measurement of about 80%, about 85%, about 90%, about 95%, about 99%, or any ranges between the specified values.

In some embodiments, the compound can be characterized by having a structure according to Formula I:

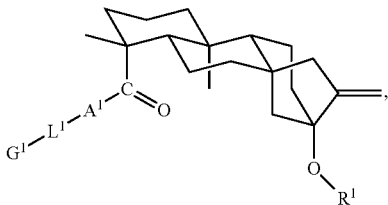

(Formula I)

wherein:
$R^1$ is hydrogen, 1-β-D-glucopyranosyl, 2-(1-β-3-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L-rhamnopyranosyl)-3-(1-β-D-glucopyranosyl)-1-β-D-glucopyranosyl, 2-(1-β-D-xylopyranosyl)-3-(1-β-D-glucopyranosyl)-1-β-D-glucopyranosyl;
$A^1$ is $NR^{10}$ or O;
$L^1$ is a bond linking $A^1$ and $G^1$, a $C_{1-6}$ alkylene linker, a tetrahydropyran ring, or forms a 5- to 7-membered heterocyclic ring with $A^1$ when $A^1$ is $NR^{10}$,
$G^1$ is OH, $CH_2OH$, COOH, $OR^{12}$, $CONR^{13}R^{14}$, $COOR^{15}$, a tetrahydropyran ring, or

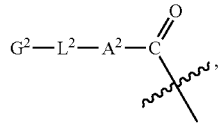

wherein $A^2$ is $NR^{20}$ or O;
$L^2$ is a bond linking $A^2$ and $G^2$, a $C_{1-6}$ alkylene linker, a tetrahydropyran ring, or forms a 5- to 7-membered heterocyclic ring with $A^2$ when $A^2$ is $NR^{20}$;
and $G^2$ is OH, $CH_2OH$, COOH, $R^{21}$, $OR^{22}$, $CONR^{23}R^{24}$ or $COOR^{25}$,
wherein
the $C_{1-6}$ alkylene linker at each occurrence is independently optionally substituted, for example, with one or more substituents independently selected from the group consisting of OH and alkyl, wherein the alkyl is optionally substituted, for example, with one or more groups each independently selected from the group consisting of optionally substituted aryl, optionally substituted heteroaryl, COOH, $CONH_2$, $NH_2$, NHC(=N)$NH_2$, SH, SMe, OMe, OH, and $Me_3N^+$; each of the tetrahydropyran ring at each occurrence is independently optionally substituted, for example, with one or more groups each independently selected from the group consisting of OH, Cl, $CH_2Cl$, $CH_2OH$, COOH, alkyl, and $OR^{30}$, wherein $R^{30}$ is a pyranosyl or a tetrahydrofuran ring;
each of the tetrahydrofuran ring at each occurrence is independently optionally substituted, for example, with one or more groups each independently selected from the group consisting of OH, Cl, $CH_2Cl$, $CH_2OH$, COOH, and alkyl; and
each of $R^{10}$, $R^{11}$, $R^{12}$, $R^{13}$, $R^{14}$, $R^{20}$, $R^{21}$, $R^{22}$, $R^{23}$, and $R^{24}$ is independently selected from the group consisting of H, alkyl, cycloalkyl, and heterocycle, wherein each of the alkyl, cycloalkyl, and heterocycle is optionally substituted, for example, with one or more groups each independently selected from the group consisting of alkyl, optionally substituted aryl, optionally substituted heteroaryl, COOH, $CONH_2$, $NH_2$, NHC(=N)$NH_2$, SH, SMe, OMe, OH, and $Me_3N^+$; and
$R^{15}$ and $R^{25}$ are each independently a $C_{1-6}$ alkyl.
or a salt thereof,
provided that the compound of Formula I is not rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, or rebaudioside O.

In some embodiments, $R^1$ in Formula I can be a corresponding sugar unit in naturally occurring rebaudiosides. For example, in one embodiment, the $R^1$ group in Formula I is 2,3-bis(1-β-D-glucopyranosyl)-1-β-D-glucopyranosyl, which corresponds to the sugar unit attached to the hydroxyl terminal of steviol in rebaudiosides A and B. In one embodiment, the $R^1$ group in Formula I is 2-(1-α-L-rhamnopyranosyl)-3-(1-β-D-glucopyranosyl)-1-β-D-glucopyranosyl. In one embodiment, the $R^1$ group in Formula I is 2-(1-β-D-xylopyranosyl)-3-(1-β-D-glucopyranosyl)-1-β-D-glucopyranosyl.

In some embodiments, $A^1$ in Formula I is O.

In other embodiments, $A^1$ in Formula I is $NR^{10}$. In some embodiments, $R^{10}$ is H. In some embodiments, $R^{10}$ is a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, NHC(=N)$NH_2$, SH, SMe, OMe, OH and $Me_3N^+$. In some embodiments, $R^{10}$ is a $C_{1-4}$ alkyl optionally substituted with one of a $C_{1-4}$ alkyl, phenyl, and 3'-hydroxy-4'-methoxyphenyl. In some embodiments, $R^{10}$ is a $C_{1-4}$ alkyl, which is not substituted.

In some embodiments, $L^1$ in Formula I is a bond linking $A^1$ and $G^1$. In some embodiments, $L^1$ in Formula I is a $C_{1-6}$ alkylene linker. In some embodiments, the $C_{1-6}$ alkylene linker is not substituted, and can be, for example, a $CH_2$ or $CH_2CH_2$ group.

In some embodiment, the $C_{1-6}$ alkylene linker is substituted with one or more substituents independently selected from the group consisting of OH and alkyl, wherein the alkyl is optionally substituted with one or more groups each independently selected from the group consisting of optionally substituted aryl, optionally substituted heteroaryl, COOH, $CONH_2$, $NH_2$, NHC(=N)$NH_2$, SH, SMe, OMe, OH, and $Me_3N^+$.

For example, in some embodiments, the $C_{1-6}$ alkylene linker is substituted with one or more OH groups, such as 1, 2, 3, 4, 5, or 6 OH groups. In some embodiments, the $C_{1-6}$ alkylene linker together with the $A^1$ and $G^1$ represents a sugar alcohol residue. In some embodiments, the sugar alcohol is selected from the group consisting of glycerol, erythritol, threitol, arabitol, xylitol, ribitol, mannitol, sorbitol, galactitol, fucitol, and iditol. In some embodiments, the sugar alcohol is selected from the group consisting of glycerol, erythritol, xylitol, sorbitol, and mannitol. The sugar alcohol residue can be in a D-configuration or a L-configuration. In some embodiments, the sugar alcohol residue is in a D-configuration.

In some embodiment, the $C_{1-6}$ alkylene linker is substituted with one or more optionally substituted alkyl groups. In some embodiments, the one or more optionally substituted alkyl groups are not substituted. For example, in some embodiments, the $C_{1-6}$ alkylene linker can be —(CHMe)-. In some embodiments, the one or more alkyl groups are independently substituted with one or more groups each independently selected from the group consisting of optionally substituted aryl, optionally substituted heteroaryl, COOH, CONH$_2$, NH$_2$, NHC(=N)NH$_2$, SH, SMe, OMe, OH, and Me$_3$N$^+$. In some embodiments, the $C_{1-6}$ alkylene linker is CHR$^{101}$, wherein R$^{101}$ is an alkyl group, such as a $C_{1-4}$ alkyl group, substituted with an optionally substituted aryl, optionally substituted heteroaryl, COOH, CONH$_2$, NH$_2$, NHC(=N)NH$_2$, SH, SMe, OMe, OH, or Me$_3$N$^+$. In some embodiments, R$^{101}$ is a $C_{1-4}$ alkyl group substituted with a phenyl, 4-hydroxyphenyl, imidazolyl, COOH, CONH$_2$, NH$_2$, NHC(=N)NH$_2$, SH, SMe, OMe, OH, or Me$_3$N$^+$. In some embodiments, R$^{101}$ represents a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine. As understood by those skilled in the art, the substituted carbon or carbons of the $C_{1-6}$ alkylene linker can be chiral center(s). Each of the chiral center(s) can have either an R or an S configuration for the embodiments described herein. For example, the amino acid side chain can be from either a D-amino acid or an L-amino acid.

In some embodiments, L$^1$ in Formula I is a tetrahydropyran ring. For example, the tetrahydropyran ring, which links A$^1$ and can have a structure of Formula P:

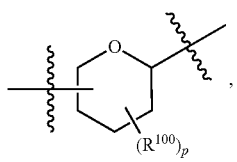

Formula P wherein p can be an integer up to 8, for example, up to 4, and R$^{100}$ at each occurrence can be independently selected from the group consisting of OH, CH$_2$OH, Cl, COOH, CH$_2$Cl, Me, and OR$^{30}$, wherein R$^{30}$ is a pyranosyl or a tetrahydrofuran ring. In some embodiments, p can be 2, 3, or 4. In some embodiments, the tetrahydropyran ring together with G$^1$ is a monosaccharide pyranosyl structure. For example, the tetrahydropyran ring together with G$^1$ can form a structure selected from the group consisting of

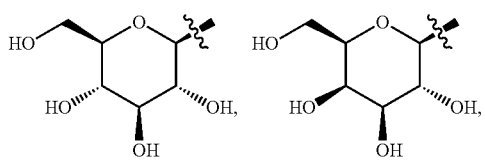

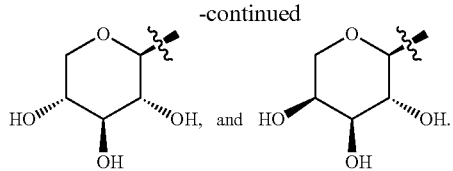

In some embodiments, the tetrahydropyran ring with G$^1$ is a disaccharide or a trisaccharide, with a pyranosyl unit connected to A$^1$. For example, the tetrahydropyran ring with G$^1$ can form a structure selected from the group consisting of

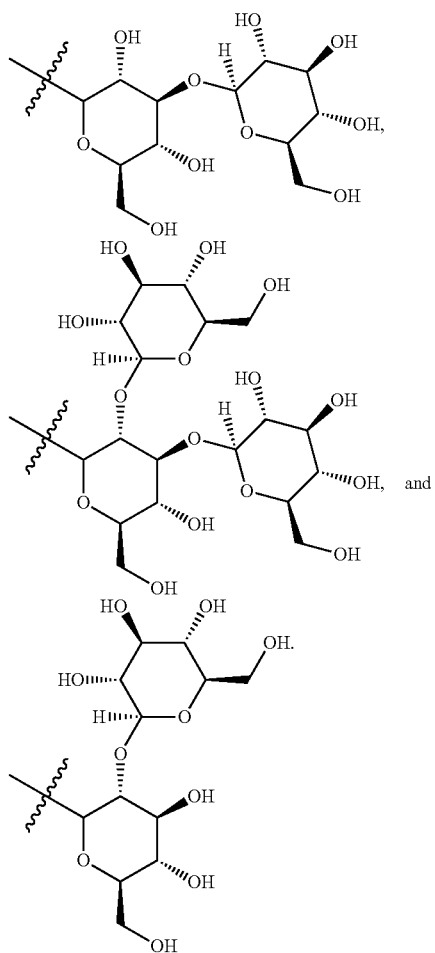

In some embodiments, L$^1$ in Formula I forms a 5- to 7-membered heterocyclic ring with A$^1$ when A$^1$ is NR$^{10}$. For example, in some embodiments, A$^1$-L$^1$-G$^1$ can be

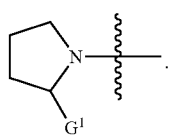

In some embodiments, G$^1$ in Formula I can be OH.
In some embodiments, G$^1$ in Formula I can be CH$_2$OH.
In some embodiments, G$^1$ in Formula I can be COOH.
In some embodiments, G$^1$ in Formula I can be COOR$^{15}$.
In some embodiments, R$^{15}$ is a $C_{1-6}$ alkyl, for example, methyl, ethyl, n-propyl, isopropyl, n-butyl, sec-butyl, isobutyl, tert-butyl, n-pentyl, n-hexyl, etc. In some embodiment, $R^{15}$ is methyl or ethyl.

In some embodiments, $G^1$ in Formula I can be $R^{11}$. In some embodiments, $R^{11}$ can be a hydrogen. In some embodiments, $R^{11}$ can be an alkyl, such as an unsubstituted $C_{1-6}$ alkyl, for example, methyl, ethyl, n-propyl, isopropyl, n-butyl, sec-butyl, iso-butyl, tert-butyl, n-pentyl, n-hexyl, etc. For example, in some embodiments, when $R^{11}$ is an alkyl, $A^1$-$L^1$-$G^1$ can be an alkoxyl group, which therefore forms an ester group with the attached carbonyl group. Other suitable $R^{11}$ groups are described herein.

In some embodiments, $G^1$ in Formula I can be $OR^{12}$. Suitable $R^{12}$ are described herein.

In some embodiments, $G^1$ in Formula I can be $CONR^{13}R^{14}$. In some embodiments, one of $R^{13}$ and $R^{14}$ is hydrogen, and the other of $R^{13}$ and $R^{14}$ is an alkyl group optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$. In some embodiments, one of $R^{13}$ and $R^{14}$ can be an amino acid residue selected from the group consisting of glycine, alanine, arginine, asparagine, aspartic acid, cysteine, glutamic acid, glutamine, histidine, isoleucine, leucine, lysine, methionine, phenylalanine, serine, threonine, tryptophan, tyrosine, and valine. In some embodiments, the amino acid residue can be from either a D-amino acid or an L-amino acid.

In some embodiments, one of $R^{13}$ and $R^{14}$ is hydrogen, and the other of $R^{13}$ and $R^{14}$ is a heterocycle group optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$. In some embodiments, the heterocycle is thietane. In some embodiments, the thietane is unsubstituted. In some embodiments, the theitane is substituted by 1-4 methyl groups.

In some embodiments, $G^1$ in Formula I can be a tetrahydropyran ring or a tetrahydrofuran ring. For example, in some embodiments, $L^1$ is $CH_2$, and $G^1$ is a tetrahydropyran ring having a structure of Formula P2:

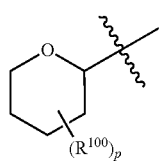

Formula P2 wherein p can be an integer up to 8, for example, up to 4, and $R^{100}$ at each occurrence can be independently selected from the group consisting of OH, $CH_2OH$, Cl, COOH, $CH_2Cl$, Me, and $OR^{30}$, wherein $R^{30}$ is a pyranosyl or a tetrahydrofuran ring. In some embodiments, p is preferably 2, 3, or 4. In some embodiments, two of $R^{100}$ can be attached to the same carbon on the tetrahydropyran ring. In some embodiments, the tetrahydropyran ring is a monosaccharide pyranosyl structure. In some embodiments, the tetrahydropyran ring is a disaccharide. For example, the tetrahydropyran ring can be

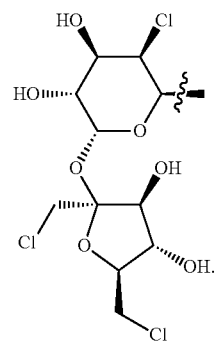

In some embodiments, $G^1$ in Formula I can be

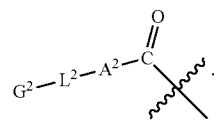

In some embodiments, $A^2$ in Formula I is O.

In other embodiments, $A^2$ in Formula I is $NR^{20}$. In some embodiments, $R^{20}$ is H. In some embodiments, $R^{20}$ is a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, $NHN(=N)NH_2$, SH, SMe, OMe, OH and $Me_3N^+$. In some embodiments, $R^{20}$ is a $C_{1-4}$ alkyl optionally substituted with one of a $C_{1-4}$ alkyl, phenyl, and 3'-hydroxy-4'-methoxyphenyl.

In some embodiments, $L^2$ in Formula I is a bond linking $A^2$ and $G^2$. In some embodiments, $L^2$ in Formula I is a $C_{1-6}$ alkylene linker, for example, a $C_{1-6}$ alkylene linker. In some embodiments, the $C_{1-6}$ alkylene linker is not substituted, for example, a $CH_2$ or $CH_2CH_2$ group.

In some embodiment, the $C_{1-6}$ alkylene linker is substituted with one or more optionally substituted alkyl groups. In some embodiments, the one or more optionally substituted alkyl groups are not substituted. For example, the $C_{1-6}$ alkylene linker can be CHMe. In some embodiments, the one or more alkyl groups are independently substituted with one or more groups each independently selected from the group consisting of optionally substituted aryl, optionally substituted heteroaryl, COOH, $CONH_2$, $NH_2$, $NHN(=N)NH_2$, SH, SMe, OMe, OH, and $Me_3N^+$. In some embodiments, the $C_{1-6}$ alkylene linker is $CHR^{201}$, wherein $R^{201}$ is H or an alkyl group, such as a $C_{1-4}$ alkyl group, substituted with an optionally substituted aryl, optionally substituted heteroaryl, COOH, $CONH_2$, $NH_2$, $NHN(=N)NH_2$, SH, SMe, OMe, OH, or $Me_3N^+$. In some embodiments, $R^{201}$ is a $C_{1-4}$ alkyl group substituted with a phenyl, 4-hydroxyphenyl, imidazolyl, COOH, $CONH_2$, $NH_2$, $NHN(=N)NH_2$, SH, SMe, OMe, OH, or $Me_3N^+$. In some embodiments, $R^{201}$ represents a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine. As understood by those skilled in the art, the substituted carbon or carbons of the $C_{1-6}$ alkylene linker can be chiral center(s). Each of the chiral center(s) can have either an R or an S configuration for the embodiments described herein. For example, the amino acid side chain can be from either a D-amino acid or an L-amino acid. Other suitable $C_{1-6}$ alkylene linkers are described herein.

In some embodiments, $G^2$ in Formula I can be COOH.

In some embodiments, $G^2$ in Formula I can be $COOR^{25}$. In some embodiment $R^{25}$ is a $C_{1-6}$ alkyl, for example, methyl, ethyl, n-propyl, isopropyl, n-butyl, sec-butyl, isobutyl, tert-butyl, n-pentyl, n-hexyl, etc. In some embodiment, $R^{15}$ is methyl or ethyl.

In some embodiments, $G^2$ in Formula I can be $CONR^{23}R^{24}$. In some embodiments, one of $R^{23}$ and $R^{24}$ is hydrogen, and the other of $R^{23}$ and $R^{24}$ is an alkyl group optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$. For example, one of $R^{23}$ and $R^{24}$ can be an amino acid residue selected from the group consisting of glycine, alanine, arginine, asparagine, aspartic acid, cysteine, glutamic acid, glutamine, histidine, isoleucine, leucine, lysine, methionine, phenylalanine, serine, threonine, tryptophan, tyrosine, and valine. In some embodiments, the amino acid residue can be from either a D-amino acid or an L-amino acid.

In some embodiments, one of $R^{23}$ and $R^{24}$ is hydrogen, and the other of $R^{23}$ and $R^{24}$ is a heterocycle group optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$. In some embodiments, the heterocycle is thietane. In some embodiments, the thietane is unsubstituted. In some embodiments, the theitane is substituted by 1-4 methyl groups.

Other suitable variations of $A^1$, $L^1$, $G^1$, $A^2$, $L^2$, and $G^2$ are described herein. The embodiments described herein include all chemically possible combinations of different variations of $A^1$, $L^1$, $G^1$, $A^2$, $L^2$, and $G^2$ described herein.

In any of the embodiments described herein, the compound having a structure according to Formula I can have an enantiomeric purity of at least 80% ee, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. In any of the embodiments described herein, the compound having a structure according to Formula I can have an diastereomeric purity of at least 80% de or more, e.g., about 80% de, about 85% de, about 90% de, about 91% de, about 92% de, about 93% de, about 94% de, about 95% de, about 96% de, about 97% de, about 98% de, about 99% de, about 99.5% de or more. In some embodiments, the compound can have an enantiomeric purity of from about 80% ee to about 100% ee, for example, about 85% ee, about 90% ee, about 95% ee, about 99% ee, about 99.5% ee, or any ranges between the specified values. In some embodiments, the compound can have a diastereomeric purity of from about 80% de to about 100% de, for example, about 85% de, about 90% de, about 95% de, about 99% de, about 99.5% de, or any ranges between the specified values.

Reb B Glycosides

Certain embodiments are directed to rebaudioside B analogs with a sugar such as a pyranosyl group attached to the carboxylic acid terminal of steviol. In some embodiments, the rebaudioside B analogs have a structure according to Formula S:

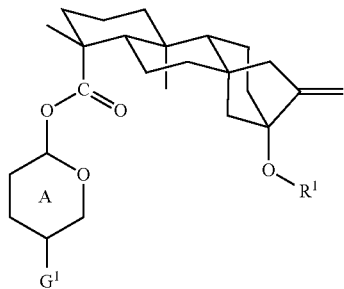

Formula S wherein $R^1$ is 2,3-bis(1-β-D-glucopyranosyl)-1-β-D-glucopyranosyl.

In some embodiments, ring A is optionally further substituted with up to four $R^{100}$, each independently selected from the group consisting of OH, $CH_2OH$, Cl, COOH, $CH_2Cl$, Me, and $OR^{30}$, wherein $R^{30}$ is a pyranosyl or a tetrahydrofuran ring. In some embodiments, $G^1$ is OH. Other suitable $G^1$ groups are described elsewhere herein.

In some embodiments, ring A is further substituted with up to 4 $R^{100}$ groups, for example, 1, 2, 3, or 4 $R^{100}$ groups. In some embodiments, $R^{100}$ at each occurrence is independently selected from the group consisting of OH, $CH_2OH$, and Me. In some embodiments, 1 or 2 $R^{100}$ groups can be independently an $OR^{30}$, wherein $R^{30}$ is a pyranosyl or a tetrahydrofuran ring. For example, ring A with G1 can form a structure selected from the group consisting of

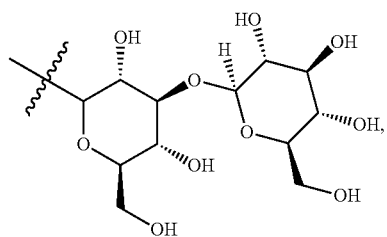

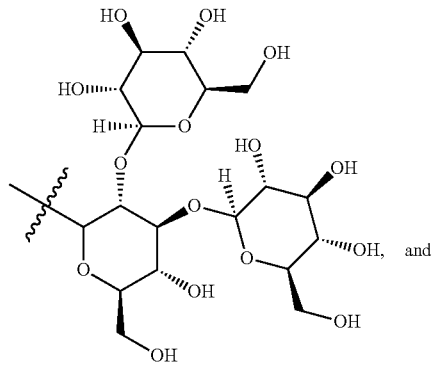

and

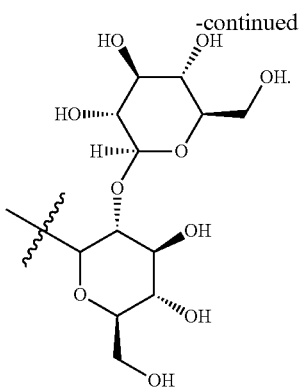

In some embodiments, the rebaudioside B analog is selected from the group consisting of

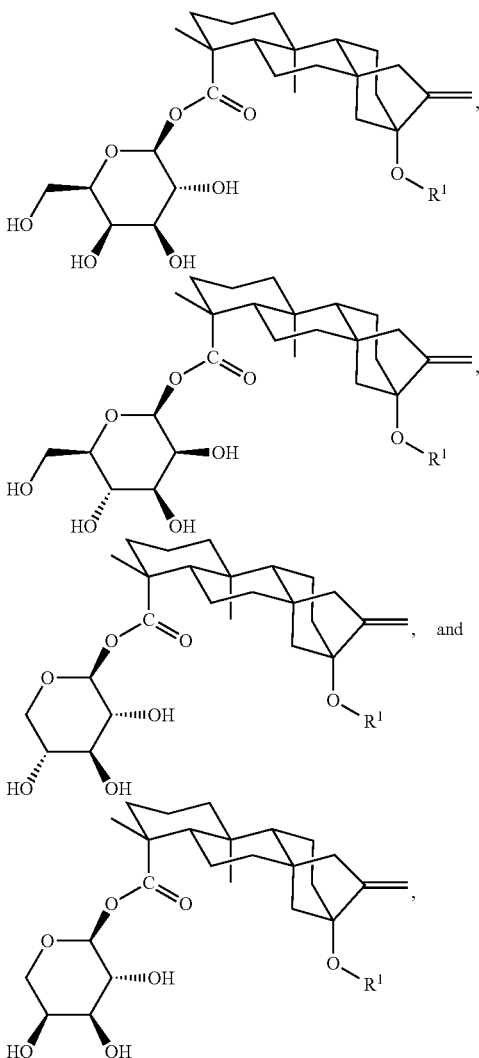

wherein $R^1$ is 2,3-bis(1-β-D-glucopyranosyl)-1-β-D-glucopyranosyl.

Reb B Amino Acid Analogs

Certain embodiments are directed to rebaudioside B analogs with an amino acid/ester residue attached to the carboxylic acid terminal of steviol. In some embodiments, the amino acid/ester residue is an alpha-amino acid residue. In some embodiments, the amino acid/ester residue is a beta- or gamma-amino acid/ester residue. In some embodiments, a dipeptide or a tripeptide is attached to the carboxylic acid terminal of steviol.

In some embodiments, the rebaudioside B analogs have a structure according to Formula A:

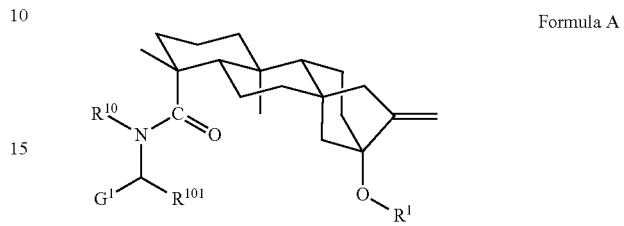

Formula A wherein $R^1$ is 2,3-bis(1-β-D-glucopyranosyl)-1-β-D-glucopyranosyl. Suitable $R^{10}$, $R^{101}$, and $G^1$ are described herein.

In some embodiments, $R^{10}$ in Formula A is H. In some embodiments, $R^{10}$ in Formula A is a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, NHN(=N)$NH_2$, SH, SMe, OMe, OH and $Me_3N^+$. In some embodiments, $R^{10}$ in Formula A is a $C_{1-4}$ alkyl optionally substituted with one of a $C_{1-4}$ alkyl, phenyl, and 3'-hydroxy-4'-methoxyphenyl.

In some embodiments, $R^{101}$ in Formula A is hydrogen. In some embodiments, $R^{101}$ in Formula A is an alkyl group, such as a $C_{1-4}$ alkyl group, substituted with an optionally substituted aryl, optionally substituted heteroaryl, COOH, $CONH_2$, $NH_2$, NHN(=N)$NH_2$, SH, SMe, OMe, OH, or $Me_3N^+$. In some embodiments, $R^{101}$ is a $C_{1-4}$ alkyl group substituted with a phenyl, 4-hydroxyphenyl, imidazolyl, COOH, $CONH_2$, $NH_2$, NHN(=N)$NH_2$, SH, SMe, OMe, OH, or $Me_3N^+$. In some embodiments, $R^{101}$ is a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine. In some embodiments, $R^{101}$ is H or a side chain of an amino acid selected from the group consisting of alanine, phenylalanine, and valine. As understood by those skilled in the art, the $R^{101}$ substituted carbon in Formula A can be a chiral center, which can have either an R or an S configuration for the embodiments described herein. For example, the amino acid side chain can be from either a D-amino acid or an L-amino acid.

In some embodiments, $G^1$ in formula A is COOH, $COOR^{15}$, or $CONR^{13}R^{14}$. Suitable $R^{13}$, $R^{14}$, and $R^{15}$ are described herein. Other suitable $G^1$ groups are described elsewhere herein.

In some embodiments, $G^1$ in Formula A is COOH.

In some embodiments, $G^1$ in Formula A is $COOR^{15}$, wherein $R^{15}$ is a $C_{1-6}$ alkyl, for example, methyl, ethyl, n-propyl, isopropyl, n-butyl, sec-butyl, iso-butyl, tert-butyl, n-pentyl, n-hexyl, etc. In some embodiment, $R^{15}$ is methyl or ethyl.

In some embodiments, the rebaudioside B analog includes a side chain of glutamic acid. For example, the rebaudioside B analog can have a structure of Formula A2 wherein suitable $G^1$ groups are described elsewhere herein:

Formula A2

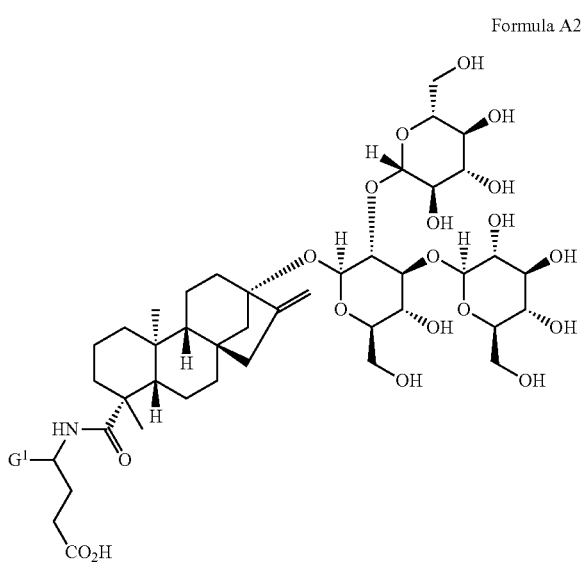

In some embodiments, $G^1$ in Formula A2 is COOH.

In some embodiments, $G^1$ in Formula A2 is $COOR^{15}$, wherein $R^{15}$ is a $C_{1-6}$ alkyl, for example, methyl, ethyl, n-propyl, isopropyl, n-butyl, sec-butyl, iso-butyl, tert-butyl, n-pentyl, n-hexyl, etc. In some embodiment, $R^{15}$ is methyl or ethyl.

In some embodiments, $G^1$ in Formula A2 is selected from the group consisting of:

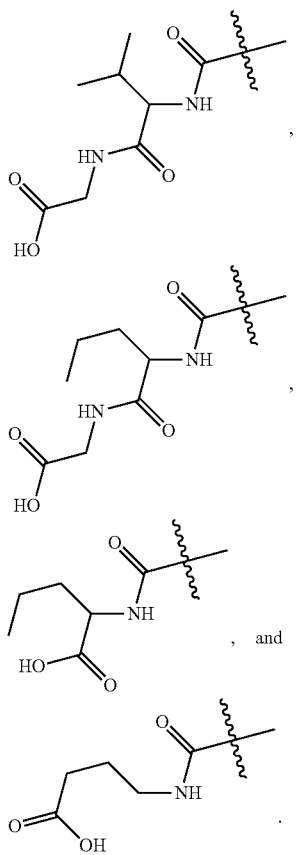

, and

In some embodiments, $G^1$ in Formula A2 is $CONR^{13}R^{14}$. Suitable $R^{13}$ and $R^{14}$ are described herein.

In some embodiments, the rebaudioside B analog includes a proline structural unit. For example, the rebaudioside B analog can have a structure of Formula A3:

Formula A3

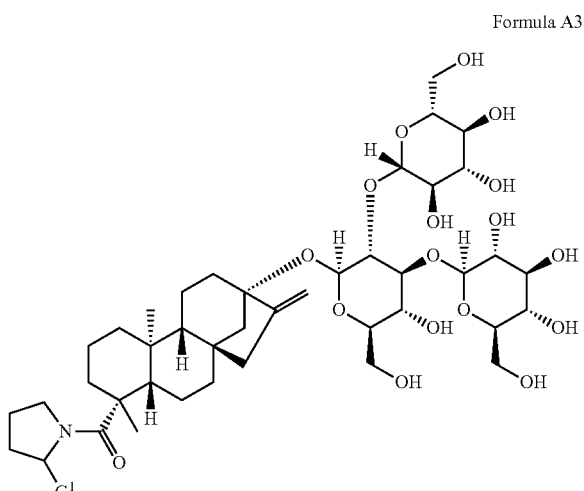

Suitable $G^1$ groups are described elsewhere herein.

In some embodiments, $G^1$ in Formula A3 is COOH.

In some embodiments, $G^1$ in Formula A3 is $COOR^{15}$, wherein $R^{15}$ is a $C_{1-6}$ alkyl, for example, methyl, ethyl, n-propyl, isopropyl, n-butyl, sec-butyl, iso-butyl, tert-butyl, n-pentyl, n-hexyl, etc. In some embodiment, $R^{15}$ is methyl or ethyl.

In some embodiments, $G^1$ in Formula A3 is $CONR^{13}R^{14}$. Suitable $R^{13}$ and $R^{14}$ are described herein.

In some embodiments, the rebaudioside B analog includes a dipeptide structural unit. For example, the rebaudioside B analog can have a structure according to Formula A4:

Formula A4

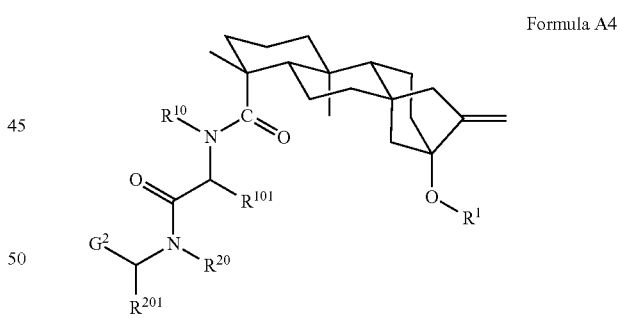

wherein $R^1$ is 2,3-bis(1-β-D-glucopyranosyl)-1-β-D-glucopyranosyl. Suitable $R^{10}$, $R^{20}$, $R^{101}$, $R^{201}$, and $G^2$ are described herein.

In some embodiments, $R^{101}$ in Formula A4 is H or a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine. As understood by those skilled in the art, the $R^{101}$ substituted carbon in Formula A4 can be a chiral center, which can have either an R or an S configuration for the embodiments described herein. For example, the amino acid side chain can be from either a D-amino acid or an L-amino acid.

In some embodiments, $R^{201}$ in Formula A4 is H or a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine. As understood by those skilled in the art, the $R^{201}$ substituted carbon in Formula A4 can be a chiral center, which can have either an R or an S configuration for the embodiments described herein. For example, the amino acid side chain can be from either a D-amino acid or an L-amino acid.

In some embodiments, $R^{10}$ in Formula A4 is H or a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, $NHN(=N)NH_2$, SH, SMe, OMe, OH and $Me_3N^+$. In some embodiments, $R^{10}$ in Formula A4 is H. In some embodiments, $R^{10}$ in Formula A4 is a $C_{1-4}$ alkyl optionally substituted with one of a $C_{1-4}$ alkyl, phenyl, and 3'-hydroxy-4'-methoxyphenyl.

In some embodiments, $R^{20}$ in Formula A4 is H or a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, $NHN(=N)NH_2$, SH, SMe, OMe, OH and $Me_3N^+$. In some embodiments, $R^{20}$ Formula A4 is H. In some embodiments, $R^{20}$ in Formula A4 is a $C_{1-4}$ alkyl optionally substituted with one of a $C_{1-4}$ alkyl, phenyl, and 3'-hydroxy-4'-methoxyphenyl.

In some embodiments, $G^2$ in Formula A4 is COOH, $COOR^{25}$, or $CONR^{23}R^{24}$.

In some embodiments, $G^2$ in Formula A4 is COOH.

In some embodiments, $G^2$ in Formula A4 is $COOR^{25}$. In some embodiments, $R^{25}$ is a $C_{1-6}$ alkyl, for example, methyl, ethyl, n-propyl, isopropyl, n-butyl, sec-butyl, iso-butyl, tert-butyl, n-pentyl, n-hexyl, etc. In some embodiment, $R^{25}$ is methyl or ethyl.

In some embodiments, $G^2$ in Formula A4 is $CONR^{23}R^{24}$. For example, in some embodiments, one of $R^{23}$ and $R^{24}$ is H, and the other of $R^{23}$ and $R^{24}$ is a heterocycle, wherein the heterocycle is optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$. In some embodiments, the heterocycle is not substituted. In some embodiments, the heterocycle is thietane. In some embodiments, the thietane is substituted with 1-4 methyl groups. In some embodiments, one of $R^{23}$ and $R^{24}$ is hydrogen, and the other of $R^{23}$ and $R^{24}$ is an alkyl group optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$. In some embodiments, one of $R^{23}$ and $R^{24}$ can be an amino acid residue selected from the group consisting of glycine, alanine, arginine, asparagine, aspartic acid, cysteine, glutamic acid, glutamine, histidine, isoleucine, leucine, lysine, methionine, phenylalanine, serine, threonine, tryptophan, tyrosine, and valine. In some embodiments, the amino acid residue can be from either a D-amino acid or an L-amino acid. Other suitable $R^{23}$ and $R^{24}$ groups are described herein.

In some embodiments, the rebaudioside B analog can be selected from the group consisting of:

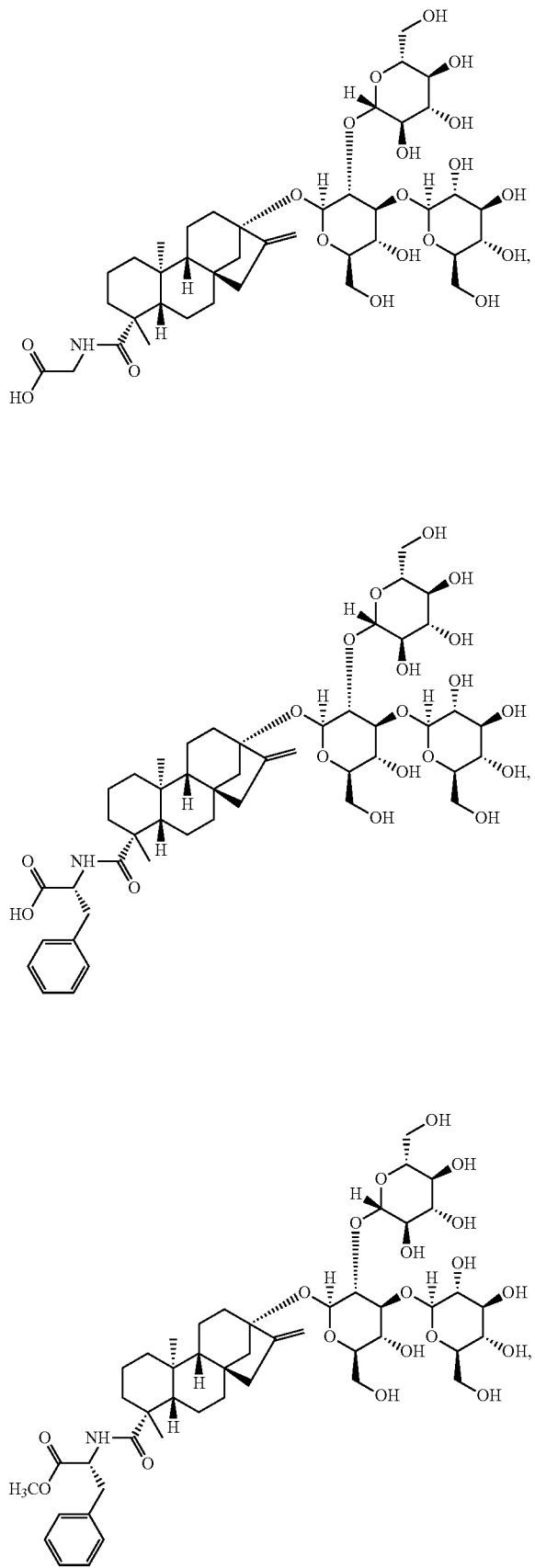

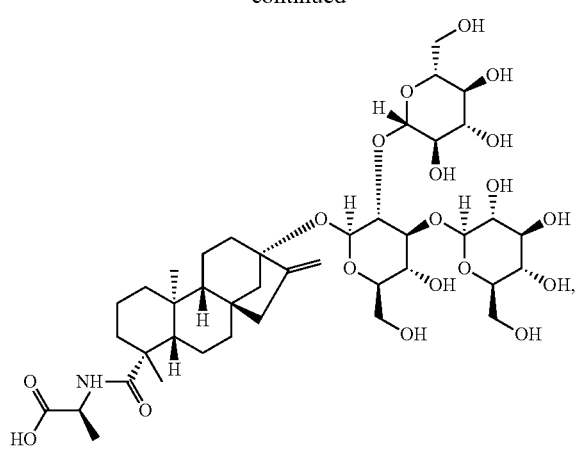
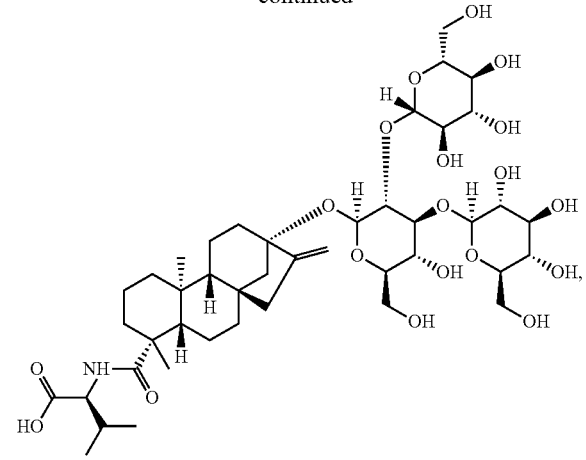
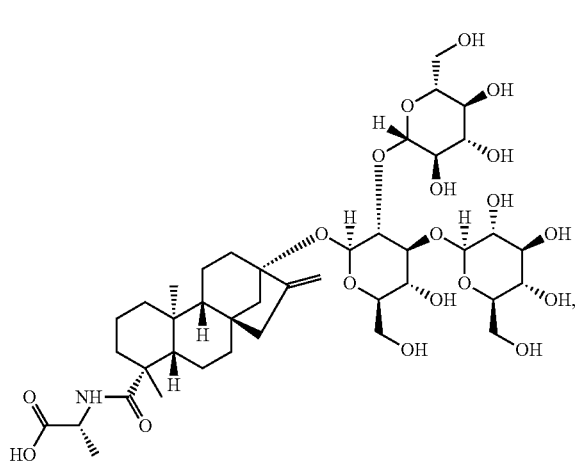
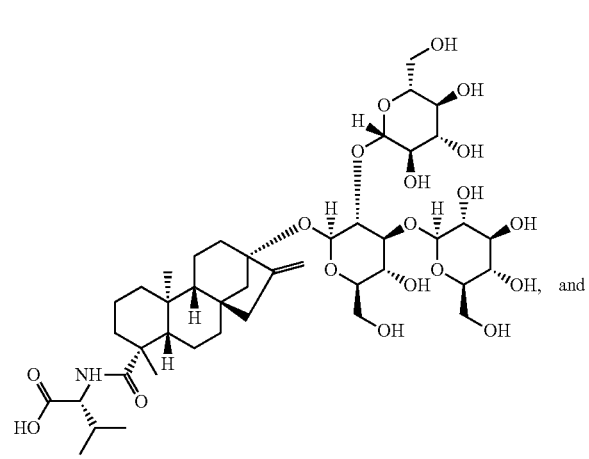
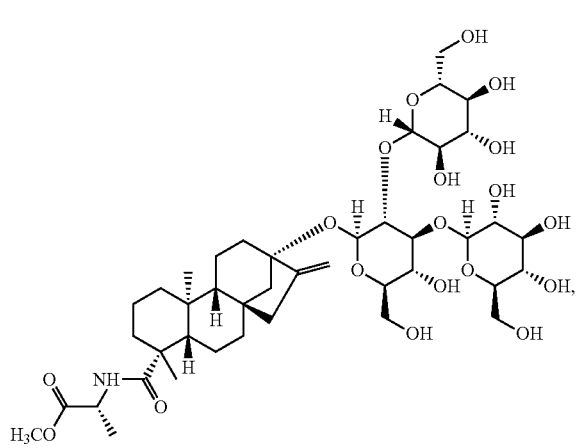
In some embodiments, the rebaudioside B analog can be selected from the group consisting of:

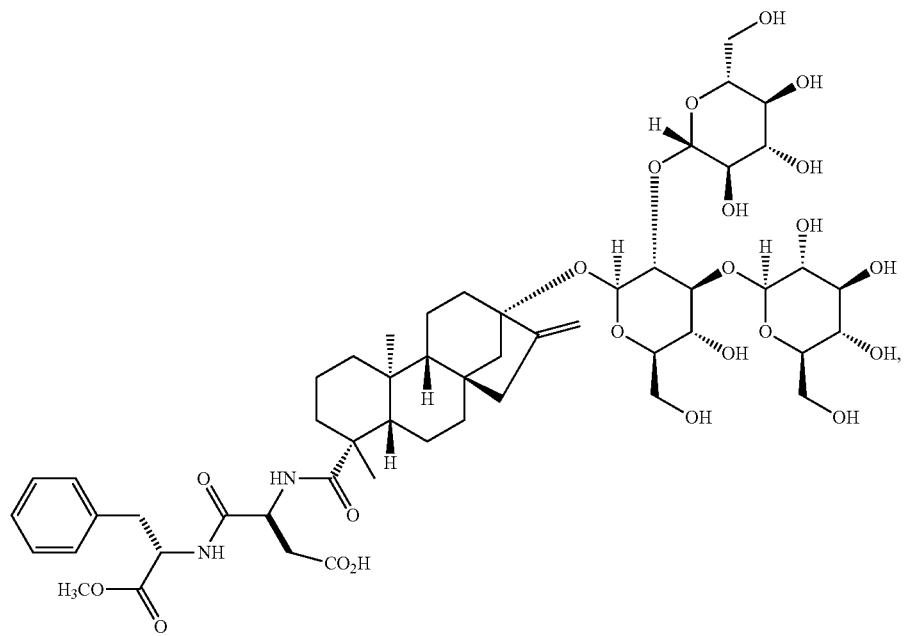
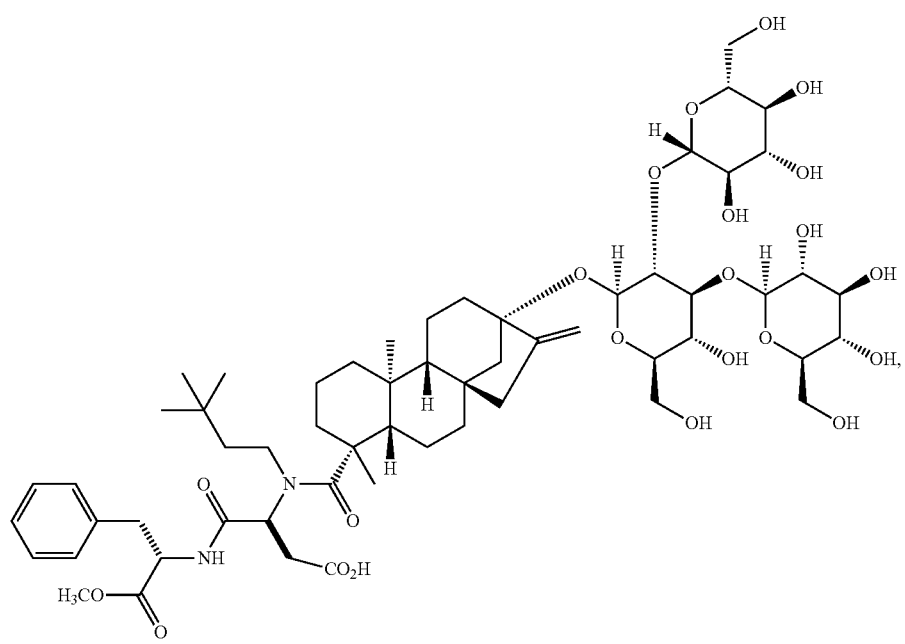

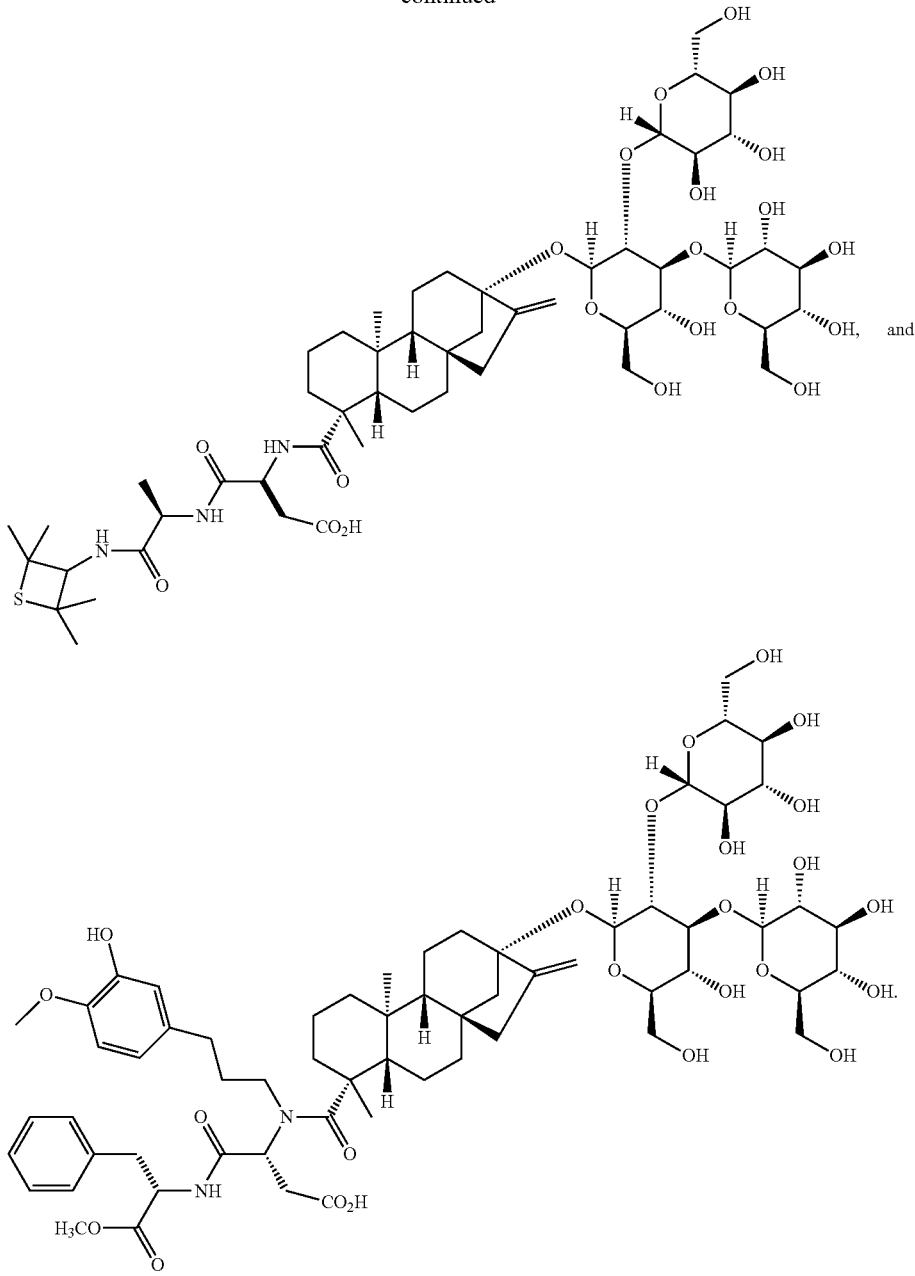

Reb B Esters

Certain embodiments are directed to rebaudioside B esters. In some embodiments, the rebaudioside B analogs have a structure according to Formula E:

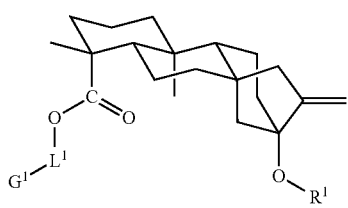

Formula E wherein $R^1$ is 2,3-bis(1-β-D-glucopyranosyl)-1-β-D-glucopyranosyl. Suitable $L^1$ and $G^1$ are described herein.

In some embodiments, $L^1$ is a bond linking the oxygen atom and $G^1$. In some embodiments, $G^1$ is $R^{11}$. In some embodiments, $R^{11}$ is a $C_{1-4}$ alkyl group, such as methyl, ethyl, n-propyl, isopropyl, n-butyl, sec-butyl, iso-butyl, or tert-butyl. Other suitable $G^1$ and $R^{11}$ groups are described herein.

In some embodiments, $L^1$ is an optionally substituted $C_{1-6}$ alkylene linker, and $G^1$ is COOH or $COOR^{15}$, wherein $R^{15}$ is a $C_{1-4}$ alkyl. In some embodiments, $L^1$ is CHMe, and $G^1$ is COOH or $COOR^{15}$, wherein $R^{15}$ is a $C_{1-4}$ alkyl.

In some embodiments, the rebaudioside B analog is selected from the group consisting of:

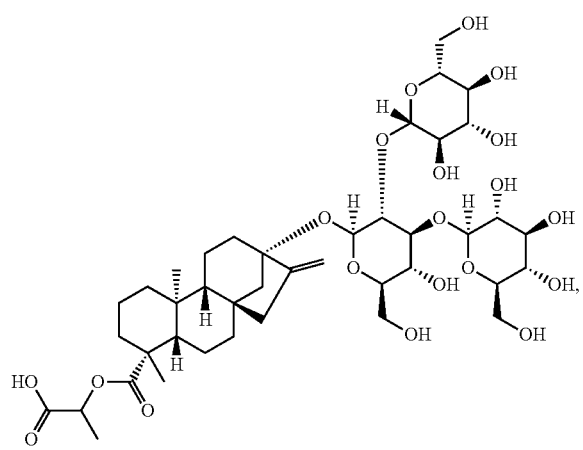

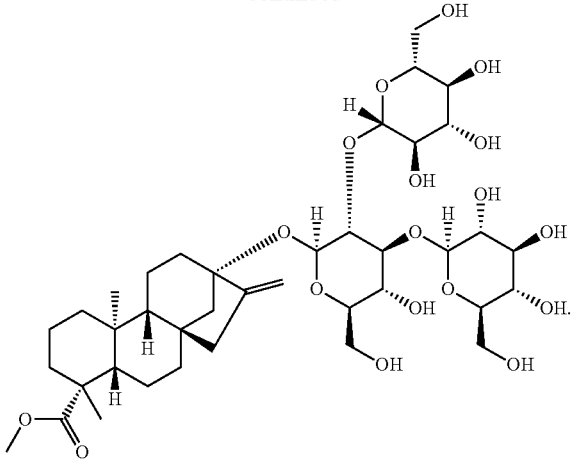

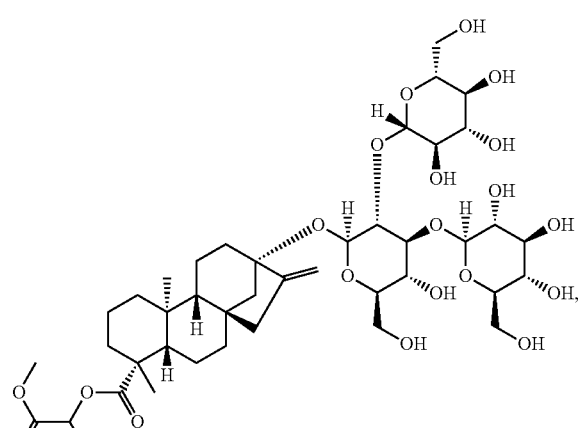

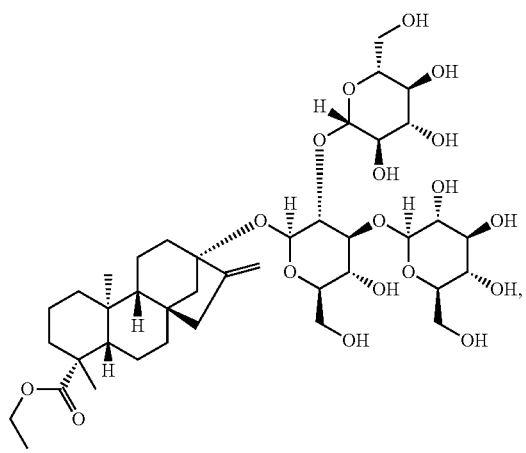 and

Reb B Sugar Alcohols Analogs

Certain embodiments are directed to rebaudioside B sugar alcohol analogs. In some embodiments, the rebaudioside B analogs have a structure according to Formula SA:

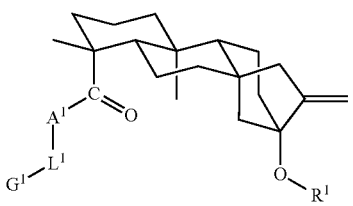

Formula SA wherein $R^1$ is 2,3-bis(1-β-D-glucopyranosyl)-1-β-D-glucopyranosyl, and $A^1$-$L^1$-$G^1$ represents a sugar alcohol residue. Sugar alcohols are known in the art and can be used in embodiments described herein. The sugar alcohols can be in either a D-configuration or an L-configuration. In some embodiments, the sugar alcohol is in a D-configuration.

In some embodiments, $A^1$-$L^1$-$G^1$ in Formula SA represents an acyclic sugar alcohol residue. In some embodiments, the acyclic sugar alcohol is selected from the group consisting of glycerol, erythritol, threitol, arabitol, xylitol, ribitol, mannitol, sorbitol, galactitol, fucitol, and iditol. In some embodiments, $A^1$-$L^1$-$G^1$ in Formula SA represents a sugar alcohol residue selected from the group consisting of glycerol, erythritol, xylitol, sorbitol, and mannitol.

In some embodiments, the rebaudioside B analog is selected from the group consisting of:

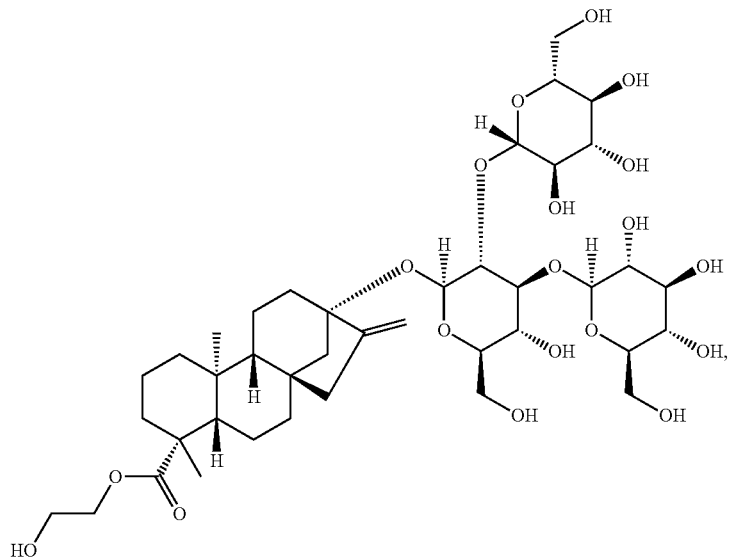
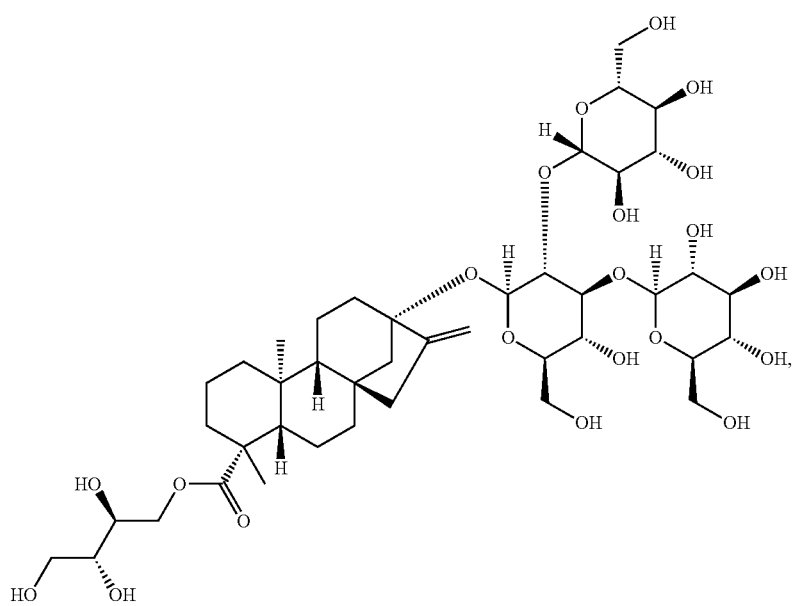

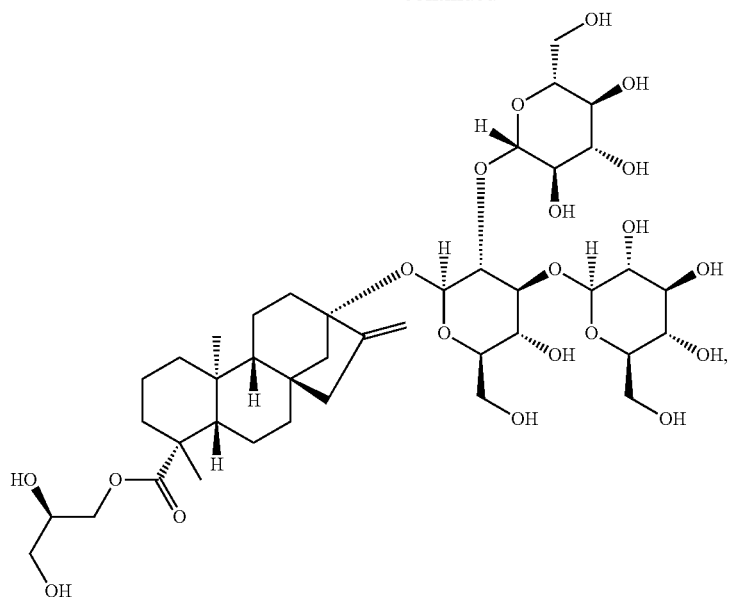
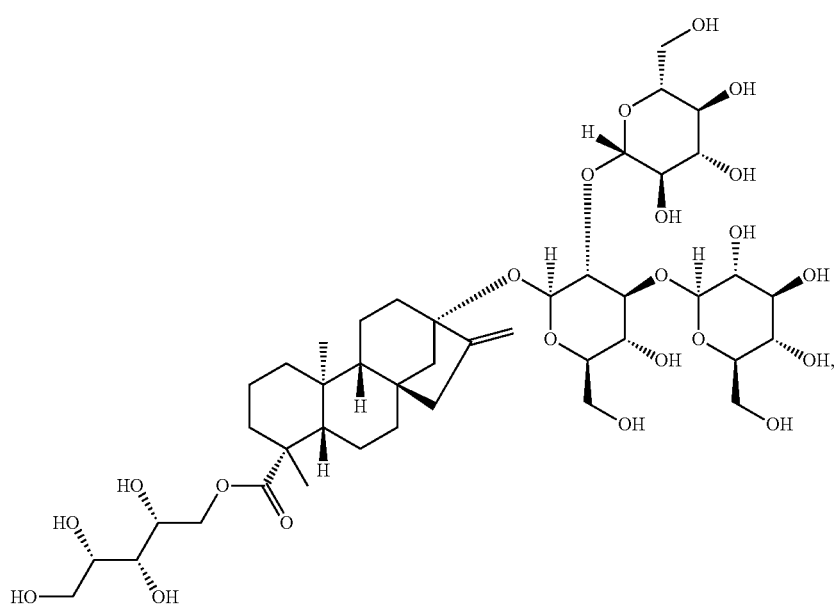

-continued
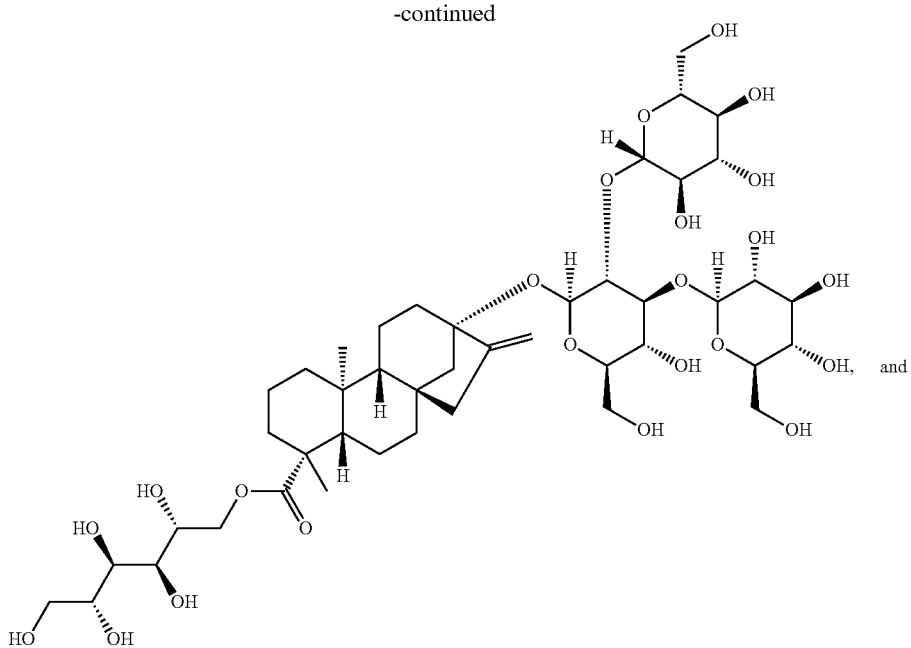
and
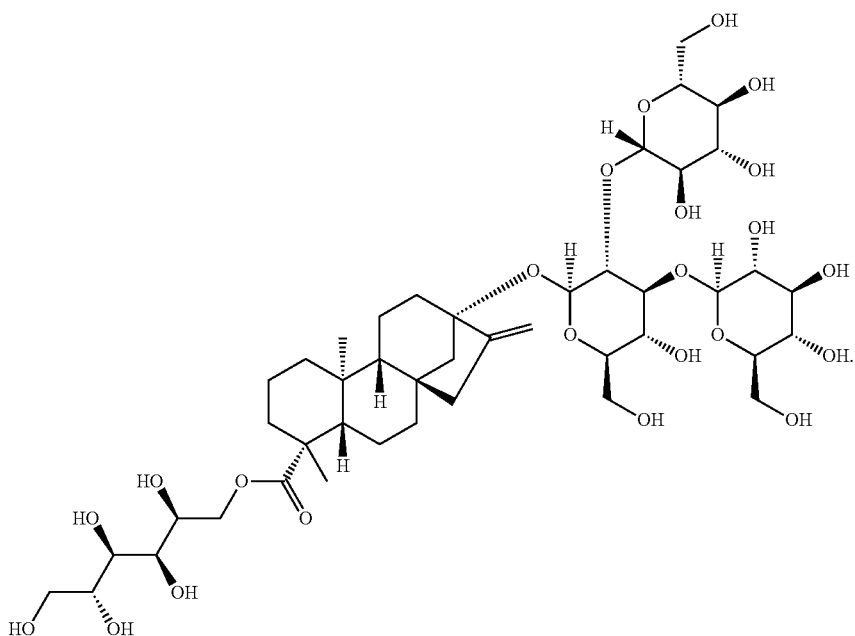
Other Reb B Analogs
Certain embodiments are directed to rebaudioside B analogs containing a disaccharide unit attached to the carboxylic acid terminal of steviol. For example, in some embodiments, the rebaudioside B analog has a structure:

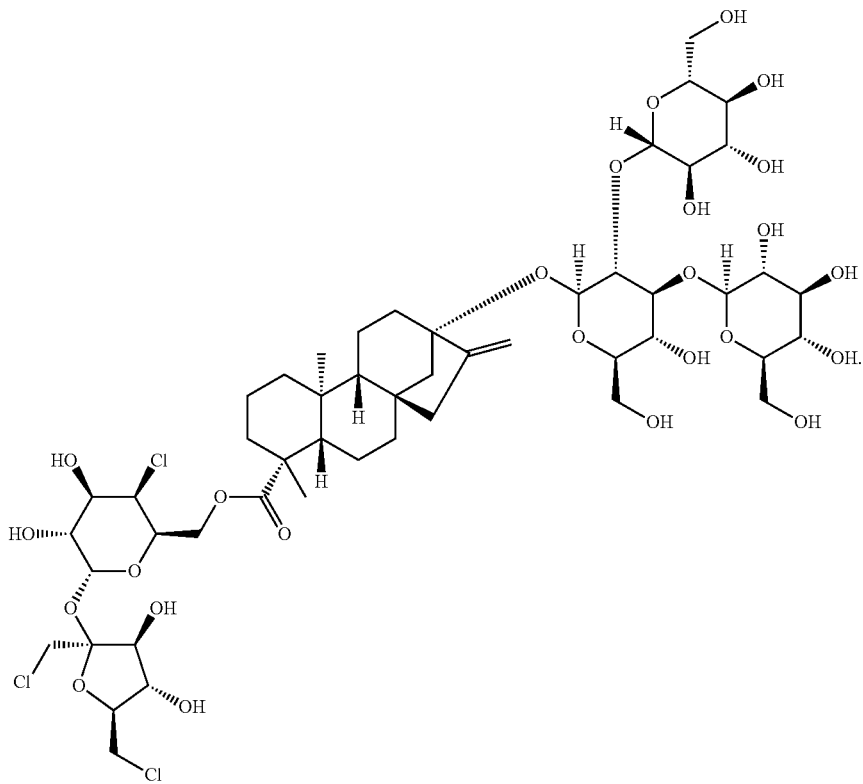

Synthesis of Reb Analogs

Rebaudioside analogs described herein can be chemically synthesized using methods known to those skilled in the art in view of this disclosure, or by the illustrative methods shown in Method 1 below. Suitable protecting can be employed in the synthesis, if needed. See Wuts, P. G. M.; Greene, T. W., "Greene's Protective Groups in Organic Synthesis", 4th Ed., J. Wiley & Sons, NY, 2007.

Method 1

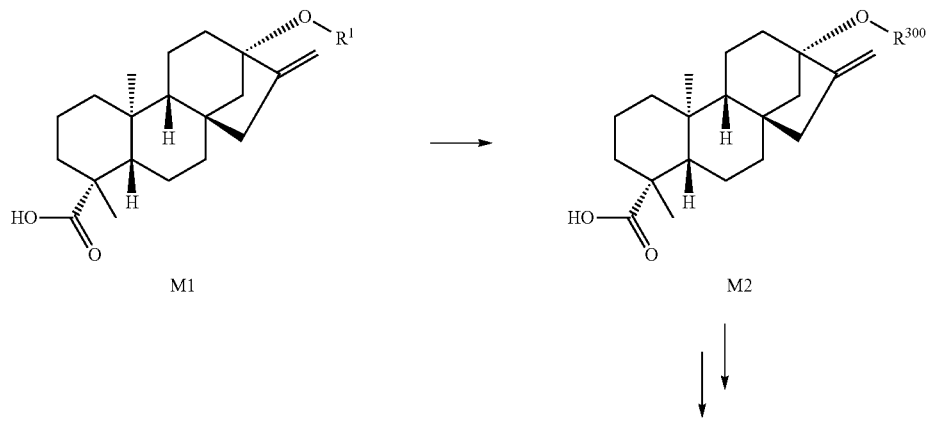

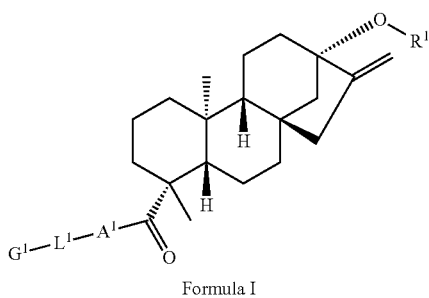

Formula I

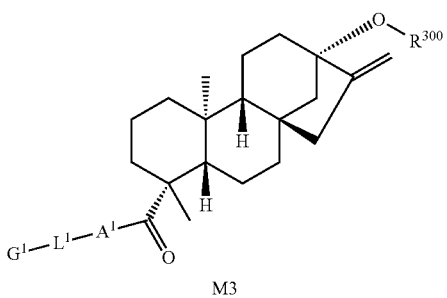

M3

$R^1$, $R^{300}$, $A^1$, $L^1$, and $G^1$ shown in Method 1 are as defined herein.

In general, the sugar unit $R^1$ in a rebaudioside carboxylic acid M1 (e.g., rebaudioside B) is first protected with a suitable protecting group such as an acyl group to provide a protected rebaudioside carboxylic acid M2, wherein $R^{300}$ is a protected sugar unit. For example, in some embodiments, when $R^1$ is 2,3-bis(1-β-D-glucopyranosyl)-1-β-D-glucopyranosyl, $R^{300}$ can be

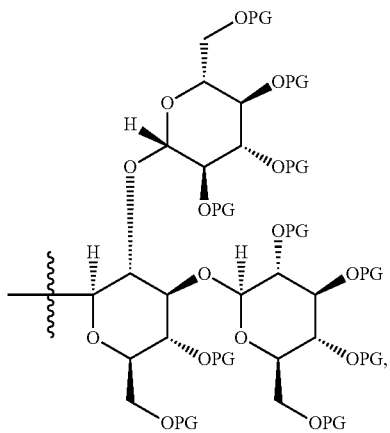

wherein each PG refers to a protecting group, which can be the same or different at each occurrence. Suitable PG for protecting sugars include any of those known in the art.

In some embodiments of $R^{300}$, the sugar unit $R^1$ is peracetylated, i.e.:

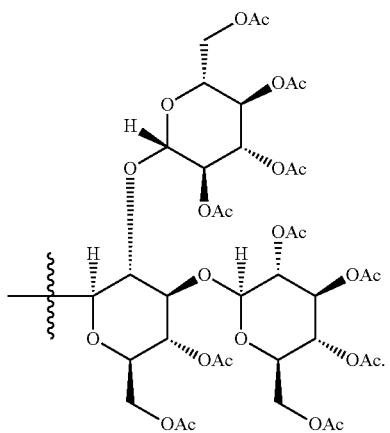 [SMILES: *[C@@H]1O[C@H](COC(C)=O)[C@@H](OC(C)=O)[C@H](O[C@@H]2O[C@H](COC(C)=O)[C@@H](OC(C)=O)[C@H](OC(C)=O)[C@H]2OC(C)=O)[C@H]1O[C@@H]1O[C@H](COC(C)=O)[C@@H](OC(C)=O)[C@H](OC(C)=O)[C@H]1OC(C)=O]

The protected rebaudioside M2 can then undergo a glycosylation reaction, for example, with an activated sugar, to form a glycoside, or a coupling reaction with an amine or an alcohol to form an amide or ester bond, respectively. Methods for forming such glycoside, amide or ester bond are known in the art. Exemplary procedures are described in the Examples section herein. Depending on the definition of $A^1$, $L^1$, and $G^1$, two or more consecutive glycosylation or coupling reactions can be used to transform M2 into M3. For example, when $A^1$-$L^1$-$G^1$ includes a dipeptide unit, one way to synthesize such compounds is to introduce two amino acids consecutively in two coupling reaction steps. For example, M2 can be first reacted with a first optionally protected amino acid to form a mono-amino acid intermediate, which can then followed by a coupling reaction with a second optionally protected amino acid to form M3. In some embodiments, the synthetic route to M3 can include optional deprotection steps after the coupling of the first optionally protected amino acid and/or the second optionally protected amino acid. Those skilled in the art can adjust the synthetic procedure for specific $A^1$, $L^1$, and $G^1$ in view of the disclosure herein.

To synthesize a compound of Formula I, rebaudioside M3 can be deprotected through known deprotection methods for the protecting groups used.

Sweetener Composition Comprising Rebaudioside Analogs as Sweeteners

In some embodiments, the compound described herein can be characterized as a high potency sweetener. In some embodiments, the compound can be characterized as a high potency sweetener with a good sweetness profile. For example, as shown in the Examples section, various rebaudioside B analogs, such as rebaudioside B sugar derivatives or amino acid derivatives, are sweeteners. Thus, in some embodiments, the compound described herein can be used as a sweetener directly or can be used in a sweetener composition. In some embodiments, the compound described herein can be used as a sweetener at concentrations above its sweetness recognition threshold.

In some embodiments, the present disclosure provides a sweetener composition comprising a compound described herein, for example, a compound of Formula I, in a concentration above its sweetness recognition threshold. In some embodiments, the compound described herein is the only sweetener present in the sweetener composition. In some embodiments, the sweetener composition comprises a compound selected from the group consisting of compounds according to Formula S, Formula A, for example, Formulae A2-A4, Formula SA, and combinations thereof. In some embodiments, the sweetener composition comprises a compound selected from the group consisting of compounds 5, 7A-7G, 5A1-5E1, 5A2-5E2, as specified in the Examples section, and combinations thereof. In some embodiments, the sweetener composition comprises a compound selected from the group consisting of compounds 5, 7A-7D, 5A2-5E2, and combinations thereof. In some embodiments, the sweetener composition comprises a compound selected from the group consisting of compounds 5, 7A-7D, and combinations thereof. In some embodiments, the sweetener composition comprises a compound selected from the group consisting of compounds 7A-7D and combinations thereof. In some embodiments, the sweetener composition comprises a compound selected from the group consisting of compounds 5A2-5E2 and combinations thereof. In some embodiments, the sweetener composition comprises compound 7D.

In some embodiments, the sweetener composition further comprises a second sweetener. The second sweetener can be a nutritive or non-nutritive, natural or synthetic sweetener, or a combination of such sweeteners, so long as the second sweetener or combination of sweeteners provides a taste which is perceived as sweet by the sense of taste. The perception of flavoring agents and sweetening agents can depend to some extent on the interrelation of elements. Flavor and sweetness can also be perceived separately, i.e., flavor and sweetness perception can be both dependent upon each other and independent of each other. For example, when a large amount of a flavoring agent is used, a small amount of a sweetening agent can be readily perceptible and vice versa. Thus, the oral and olfactory interaction between a flavoring agent and a sweetening agent can involve the interrelationship of elements. In some embodiments, the second sweetener is a nutritive sweetener. In some embodiments, the second sweetener is a non-nutritive sweetener. In some embodiments, the second sweetener is a natural sweetener. In some embodiments, the second sweetener is an artificial sweetener.

When used to sweeten, the second sweetener is present in an amount above the sweeteners' sweetness recognition threshold concentration.

In certain embodiments, the second sweetener can include one or more nutritive sweeteners in an amount of from about 1% to about 20% by weight of the sweetener composition, such as from about 3% to about 16% by weight, or from about 5% to about 12% by weight, depending upon the desired level of sweetness in the sweetener composition.

In certain embodiments, the second sweetener can include non-nutritive sweeteners in an amount ranging from about 1 ppm to about 600 ppm in the sweetener composition, depending upon the particular non-nutritive sweetener(s) being used and the desired level of sweetness in the sweetener composition.

Exemplary natural nutritive sweeteners suitable for use as a second sweetener include crystalline or liquid sucrose, fructose, glucose, dextrose, maltose, trehalose, fructo-oligosaccharides, glucose-fructose syrup from natural sources such as apple, chicory, and honey; high fructose corn syrup, invert sugar, maple syrup, maple sugar, honey, brown sugar molasses, cane molasses, such as first molasses, second molasses, blackstrap molasses, and sugar beet molasses; sorghum syrup, and mixtures thereof.

Other sweeteners suitable for use as a second sweetener include, but are not limited to, sugar alcohols such as erythritol, sorbitol, mannitol, xylitol, lactitol, isomalt, malitol, tagatose, trehalose, galactose, rhamnose, cyclodextrin, ribulose, threose, arabinose, xylose, lyxose, allose, altrose, mannose, idose, lactose, maltose, isotrehalose, neotrehalose, palatinose or isomaltulose, erythrose, deoxyribose, gulose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, and mixtures thereof.

Other sweeteners suitable for use as a second sweetener include rare sugars such as D-allose, D-psicose (also known as D-allulose), L-ribose, D-tagatose, L-glucose, L-fucose, L-arabinose, D-turanose, D-leucrose, and mixtures thereof.

Exemplary artificial sweeteners suitable for use as a second sweetener herein include, but are not limited to, saccharin, cyclamate, aspartame, neotame, advantame, acesulfame potassium, sucralose, mixtures thereof.

Exemplary natural non-nutritive potent sweeteners suitable for use as a second sweetener include steviol glycosides (e.g., stevioside, steviolbioside, rebaudioside A, rebaudioside B, rebaudioside C, rebaudioside D, rebaudioside E, rebaudioside F, rebaudioside H, rebaudioside I, rebaudioside N, rebaudioside K, rebaudioside J, rebaudioside O, rebaudioside M, dulcoside A, rubusoside, iso-steviol glycosides such as iso-rebaudioside A, and mixtures thereof), Lo Han Guo powder, neohesperidin dihydrochalcone, trilobatin, glycyrrhizin, phyllodulcin, hernandulcin, osladin, polypodoside A, baiyunoside, pterocaryoside, thaumatin, monellin, monatin, mabinlins I and II, and mixtures thereof.

In other embodiments, Lo Han Guo juice concentrate can be used as a nutritive sweetener as a second sweetener.

Other suitable sweeteners that can be used as a second sweetener are known in the art, for example, as described in WO 2016/040577 A1. In certain embodiments, combinations of one or more natural nutritive sweeteners, one or more artificial sweeteners, and/or one or more natural non-nutritive potent sweeteners can be used as a second sweetener.

In some particular embodiments, the second sweetener is selected from the group consisting of a steviol glycoside, Stevia rebaudiana extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and mixtures of any of them. In some embodiments, the second sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

In some embodiments, the sweetener composition can include at least one sweetness enhancer in a concentration sufficient to further enhance the sweetness of the compound and/or the second sweetener but in a concentration below the sweetness enhancer's sweetness recognition threshold concentration. In certain embodiments, the sweetness enhancer can be present at a concentration below its sweetness recognition threshold concentration. For example, and in certain embodiments, the sweetener composition can contain up to about 2 weight percent each of D-psicose, erythritol, or combination thereof. In some embodiments, D-psicose and/or erythritol can be present in an amount ranging from about 0.5 to about 2.0 weight percent. Alternatively, D-psicose can be present in an amount ranging from about 0.5 to about 2.0 weight percent and erythritol can be present in an amount ranging from about 0.5 to about 1 weight percent.

Nonlimiting suitable sweetness enhancers include those known in the art. In some embodiments, the sweetener composition comprises, in addition to a compound described herein, D-psicose, erythritol, rubusoside, rebaudioside B, rebaudioside C, trilobatin, phyllodulcin, brazzein, mogrosides, or a combination of any of the foregoing.

In some embodiments, the sweetness enhancer can be a rare sugar supplemental sweetness enhancer. Exemplary rare sugars include D-psicose (also referred to as D-allulose), D-allose, L-ribose, D-tagatose, L-glucose, L-fucose, L-arabinose, D-turanose, D-leucrose, and mixtures thereof.

In some embodiments, the sweetness enhancer can be a non-nutritive natural enhancer. Suitable non-nutritive natural enhancers include steviol glycosides. Suitable steviol glycosides, include, but are not limited to, stevioside, rebaudioside A, rebaudioside B, rebaudioside C, rebaudioside D, rebaudioside E, rebaudioside F, rebaudioside H, rebaudioside I, rebaudioside N, rebaudioside K, rebaudioside J, rebaudioside O, rebaudioside M, rubusoside, dulcoside A, iso-steviol glycosides such as iso-rebaudioside A, and mixtures thereof. In a particular embodiment, the sweetness enhancer can be rubusoside, rebaudioside C or rebaudioside B. In other embodiments, the non-nutritive natural sweetness enhancer can be a mogrol glycoside. Suitable mogrol glycosides, include, but are not limited to, mogroside V, isomogroside, mogroside IV, siamenoside, and mixtures thereof.

In some embodiments, the sweetness enhancer can be a sugar alcohol sweetness enhancer. Suitable sugar alcohols include erythritol, sorbitol, mannitol, xylitol, lactitol, isomalt, malitol, and mixture thereof.

In some embodiments, the sweetness enhancer can be a FEMA GRAS sweetness enhancers. Suitable FEMA GRAS enhancers include, but are not limited to, FEMA GRAS enhancer 4802, FEMA GRAS enhancer 4469, FEMA GRAS flavor 4701, FEMA GRAS enhancer 4720 (rebaudioside C), FEMA GRAS flavor 4774, FEMA GRAS enhancer 4708, FEMA GRAS enhancer 4728, FEMA GRAS enhancer 4601 (rebaudioside A) and combinations thereof.

In some embodiments, the sweetness enhancer can be a benzoic acid based sweetness enhancer.

Other suitable sweetness enhancers are known in the art, for example, as described in WO 2016/040577 A1, in U.S. Patent Application Publication Nos. 2014/0271996, US 2014/0093630, 2014/0094453, and 2014/0272068, along with U.S. Pat. No. 8,877,922, all of which are incorporated by reference in their entireties.

Sweetener Composition Comprising Reb Analogs as Sweetness Enhancers

In some embodiments, the compound described herein can be used as a sweetness enhancer in combination with a sweetener. For example, as shown in the Examples section, rebaudioside B galactoside 7D at 25 ppm, a concentration below Compound X→s sweetness recognition threshold, enhances the sweetness of several sweeteners, including rebaudioside A, High-Fructose Corn Syrup (HFCS), and sucrose. Thus, in some embodiments, the compound described herein can also be used as a sweetness enhancer at concentrations below its sweetness recognition threshold. In such embodiments, adding the compound described herein reduces the amount of sugar needed in a product, such as a beverage product or a food product, for a given sweetness. In some embodiments, using a compound described herein as a sweetness enhancer in the compositions described herein allows for at least a 25% reduction, by weight, in the amount of sweetener(s) in a given composition required to achieve the same sweetness level in an otherwise identical composition not including the compound.

In some embodiments, the present disclosure provides a sweetener composition comprising a sweetener and a compound described herein, for example, a compound of Formula I, wherein the compound is present in a concentration below the compound's sweetness recognition threshold concentration. In some embodiments, the sweetener composition comprises a compound selected from the group consisting of compounds according to Formula S, Formula A, for example, Formulae A2-A4, Formula SA, and combinations thereof. In some embodiments, the sweetener composition comprises a compound selected from the group consisting of compounds 5, 7A-7G, 5A1-5E1, 5A2-5E2, as specified in the Examples section, and combinations thereof. In some embodiments, the sweetener composition comprises a compound selected from the group consisting of compounds 5, 7A-7D, 5A2-5E2, and combinations thereof. In some embodiments, the sweetener composition comprises a compound selected from the group consisting of compounds 5, 7A-7D, and combinations thereof. In some embodiments, the sweetener composition comprises a compound selected from the group consisting of compounds 7A-7D and combinations thereof. In some embodiments, the sweetener composition comprises a compound selected from the group consisting of compounds 5A2-5E2 and combinations thereof. In some embodiments, the sweetener composition comprises compound 7D.

The sweetener suitable for use in the sweetener composition comprising the compound described herein in a concentration below the compound's sweetness recognition threshold concentration can be a nutritive sweetener or a non-nutritive sweetener. In some embodiments, the sweetener is a nutritive sweetener. In some embodiments, the sweetener is a non-nutritive sweetener. In some embodiments, the sweetener is a natural sweetener. In some embodiments, the sweetener is an artificial sweetener. In some embodiments, the sweetener is selected from the group consisting of a steviol glycoside, *Stevia rebaudiana* extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and mixtures of any of them. In some embodiments, the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

Other suitable sweeteners for use in the sweetener composition comprising the compound described herein in a concentration below the compound's sweetness recognition threshold concentration include any of the suitable second sweeteners described herein. In certain specific embodiments, the sweetener is rebaudioside A, HFCS, sucrose, or a combination thereof. In some particular embodiments, the sweetener is rebaudioside A. In some particular embodiments, the sweetener is HFCS. In some particular embodiments, the sweetener is sucrose.

In certain embodiments, the sweetener composition comprising the compound described herein as a sweetness enhancer can further include a supplemental sweetness enhancer. Nonlimiting suitable supplemental sweetener enhancers include those known in the art. In some embodiments, the supplemental sweetness enhancer is chosen from D-psicose, erythritol, rubusoside, rebaudioside B, rebaudioside C, trilobatin, phyllodulcin, brazzein, mogrosides, or a combination of any of the foregoing.

Other suitable supplemental sweetness enhancers for use include any of the suitable sweetener enhancers described herein.

The sweetener composition comprising the compound described herein can be used in a solid composition or a liquid composition. For example, the compound or the sweetener composition can be used as a solid tabletop sweetener or an aqueous solution. In some embodiments, the sweetener composition described herein can be formulated in an aqueous solution. The aqueous solution can be a liquid tabletop sweetener or a sweetener solution that is then added to other ingredients to form a beverage or beverage syrup (concentrate). In certain embodiments, the aqueous solution can be a syrup. Alternatively, the compound of Formula I can be added directly to food or beverage products already containing a sweetener.

Food or Beverage Products Comprising Rebaudioside Analogs

The compound or the sweetener composition comprising the compound described herein can be included in various products to modify the sweetness, taste, and/or flavor of the products. As discussed herein, the compound of Formula I can act as a sweetness enhancer when used in a concentration below its sweetness recognition threshold. Thus, in such embodiments, adding the compound of Formula I to a product can reduce the amount of sweetener required in the product. In some embodiments, using the compound or the sweetener composition described herein in the product allows for at least a 25% reduction, by weight, in the amount of sweetener(s) in the product required to achieve the same sweetness level in an otherwise identical product not including the compound or the sweetener composition described herein.

In some embodiments, the present disclosure provides a beverage product containing the compound or the sweetener composition described herein. In some embodiments, the beverage product is selected from the group consisting of carbonated beverages, non-carbonated beverages, fountain beverages, frozen carbonated beverages, powdered concentrates, beverage concentrates, fruit juices, fruit juice-flavored drinks, fruit-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and mixtures of any of them.

In certain embodiments, a beverage product in accordance with this disclosure can comprise water, a compound of Formula I, an optional second sweetener, an acidulant, and a flavoring. Exemplary flavorings include, but are not limited to, cola flavoring, citrus flavoring, spice flavorings, and combinations thereof. Carbonation in the form of carbon dioxide can be added for effervescence. In certain embodiments, preservatives can be added if desired or necessary, depending upon factors including the presence of other ingredients, production technique, desired shelf life, etc. In certain embodiments, caffeine can be added to the beverage. Other suitable ingredients are described herein.

Certain exemplary embodiments of the beverage products disclosed here are cola-flavored carbonated beverages, characteristically containing, in addition to the ingredients included in the beverage products disclosed herein, carbonated water, sweetener, kola nut extract and/or other flavorings, caramel coloring, phosphoric acid, and optionally other ingredients. Additional and alternative suitable ingredients will be recognized by those skilled in the art given the benefit of this disclosure.

In some embodiments, the present disclosure provides a food product containing the compound or the sweetener composition described herein. In some embodiments, the food product is selected from the group consisting of oatmeal, cereal, baked goods, cookies, crackers, cakes, brownies, breads, snack foods, potato chips, tortilla chips, popcorn, snack bars, rice cakes, and grain-based food products.

It should be understood that the food or beverage products in accordance with this disclosure can have any of numerous different specific formulations or constitutions. The formulation of a food or beverage product in accordance with this disclosure can vary, depending upon such factors as the product's intended market segment, its desired nutritional characteristics, flavor profile, and the like. For example, further ingredients can be added to the formulation of a particular food or beverage embodiment. Further ingredients include, but are not limited to, one or more additional sweeteners in addition to any sweetener already present, flavorings, electrolytes, vitamins, fruit juices or other fruit products, tastants, masking agents, flavor enhancers, carbonation, or any combination of the foregoing. These can be added to any of the food or beverage compositions to vary the taste, mouthfeel, and/or nutritional characteristics of the food or beverage composition.

Additional Ingredients

In certain embodiments, the food or beverage products disclosed herein can contain a flavor composition, for example, natural, nature identical, and/or synthetic fruit flavors, botanical flavors, other flavors, and mixtures thereof. As used herein, the term "fruit flavor" refers generally to those flavors derived from the edible reproductive part of a seed plant including those plants wherein a sweet pulp is associated with the seed, e.g., tomato, cranberry, and the like, and those having a small, fleshy berry. The term berry includes true berries as well as aggregate fruits, i.e., not "true" berries, but fruit commonly accepted as such. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime grapefruit, tangerine, mandarin orange, tangelo, and pomelo, apple, grape, cherry, and pineapple flavors. In certain embodiments, the food or beverage products comprise a fruit flavor component, e.g., a juice concentrate or juice. As used here, the term "botanical flavor" refers to flavors derived from parts of a plant other than the fruit. As such, botanical flavors can include those flavors derived from essential oils and extracts of nuts, bark, roots, and leaves. Also included within the term "botanical flavor" are synthetically prepared flavors made to simulate botanical flavors derived from natural sources. Examples of such flavors include cola flavors, tea flavors, and mixtures thereof. The flavor component may further comprise a blend of several of the above-mentioned flavors. In certain exemplary embodiments of the food or beverage products, a cola flavor component is used or a tea flavor component. The particular amount of the flavor component useful for imparting flavor characteristics to the food or beverage products of the present disclosure will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Juices suitable for use in certain exemplary embodiments of the food or beverage products disclosed herein include, e.g., fruit, vegetable and berry juices. Juices may be employed in the food or beverage products in the form of a concentrate, puree, single-strength juice, or other suitable forms. The term "juice" as used here includes single-strength fruit, berry, or vegetable juice, as well as concentrates, purees, milks, and other forms. Multiple different fruit, vegetable and/or berry juices can be combined, optionally along with other flavorings, to generate a concentrate or beverage having a desired flavor. Examples of suitable juice sources include plum, prune, date, currant, fig, grape, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, litchi, lemon, orange, lime, tangerine, mandarin, melon, watermelon, and grapefruit. Numerous additional and alternative juices suitable for use in at least certain exemplary embodiments will be apparent to those skilled in the art given the benefit of this disclosure. In the compositions of the present disclosure employing juice, juice can be used, for example, at a level of at least about 0.2 weight percent of the composition. In certain embodiments juice can be employed at a level of from about 0.2 weight percent to about 40 weight percent. In further embodiments, juice can be used, if at all, in an amounts ranging from about 1 weight percent to about 20 weight percent.

Juices that are lighter in color can be included in the formulation of certain exemplary embodiments to adjust the flavor and/or increase the juice content of the beverage without darkening the beverage color. Examples of such juices include apple, pear, pineapple, peach, lemon, lime, orange, apricot, grapefruit, tangerine, rhubarb, cassis, quince, passion fruit, papaya, mango, guava, litchi, kiwi, mandarin, coconut, and banana. Deflavored and decolored juices can be employed if desired.

Other flavorings suitable for use in at least certain exemplary embodiments of the food or beverage products disclosed here include, e.g., spice flavorings, such as cassia, clove, cinnamon, pepper, ginger, vanilla spice flavorings, cardamom, coriander, root beer, sassafras, ginseng, and others. Numerous additional and alternative flavorings suitable for use in at least certain exemplary embodiments will be apparent to those skilled in the art given the benefit of this disclosure. Flavorings may be in the form of an extract, oleoresin, juice concentrate, bottler's base, or other forms known in the art. In at least certain exemplary embodiments, such spice or other flavors complement that of a juice or juice combination.

The one or more flavorings may be used in the form of an emulsion. A flavoring emulsion can be prepared by mixing some or all of the flavorings together, optionally together with other ingredients of the food or beverage, and an emulsifying agent. The emulsifying agent can be added with or after the flavorings mixed together. In certain exemplary embodiments the emulsifying agent is water-soluble. Exemplary suitable emulsifying agents include gum acacia, modified starch, carboxymethylcellulose, gum tragacanth, gum ghatti and other suitable gums. Additional suitable emulsifying agents will be apparent to those skilled in the art of food or beverage formulations, given the benefit of this disclosure. The emulsifier in exemplary embodiments comprises greater than about 3% of the mixture of flavorings and emulsifier. In certain exemplary embodiments the emulsifier is from about 5% to about 30% of the mixture.

Carbon dioxide can be used to provide effervescence to certain exemplary embodiments of the food or beverage products disclosed here. Any of the techniques and carbonating equipment known in the art for carbonating beverages can be employed. Carbon dioxide can enhance beverage taste and appearance and may aid in safeguarding the beverage purity by inhibiting and/or destroying objectionable bacteria. In certain embodiments, for example, the beverage can have a $CO_2$ level up to about 4.0 volumes carbon dioxide. Other embodiments can have, for example, from about 0.5 volume to about 5.0 volumes of carbon dioxide. As used herein, one volume of carbon dioxide refers to the amount of carbon dioxide absorbed by a given quantity of a given liquid, such as water, at 60° F. (16° C.) and one atmospheric pressure. A volume of gas occupies the same space as does the liquid by which it is dissolved. The carbon dioxide content can be selected by those skilled in the art based on the desired level of effervescence and the impact of the carbon dioxide on the taste or mouthfeel of the beverage.

In certain embodiments, caffeine can be added to any of the food or beverage products described herein. For example, the amount of caffeine added can be determined by the desired properties of a given beverage or syrup, and any applicable regulatory provisions of the country where the beverage or syrup is marketed. In certain embodiments caffeine can be included in an amount sufficient to provide a final beverage product having less than about 0.02 weight percent caffeine. The caffeine must be of purity acceptable for use in beverage food or beverage. The caffeine may be natural or synthetic in origin.

The food or beverage products disclosed here can contain additional ingredients, including, generally, any of those typically found in food or beverage formulations. Examples of such additional ingredients include, but are not limited to, caramel and other coloring agents or dyes, foaming or antifoaming agents, gums, emulsifiers, tea solids, cloud components, and mineral and non-mineral nutritional supplements. Examples of non-mineral nutritional supplement ingredients are known to those of ordinary skill in the art and include, for example, antioxidants and vitamins, including Vitamins A, D, E (tocopherol), C (ascorbic acid), B (thiamine), B2 (riboflavin), B6, B12, K, niacin, folic acid, biotin, and combinations thereof. The optional non-mineral nutritional supplements are typically present in amounts generally accepted under good manufacturing practices. Exemplary amounts can be between about 1% and about 100% Recommended Daily Value (RDV), where such RDVs are established. In certain exemplary embodiments the non-mineral nutritional supplement ingredient(s) can be present in an amount of from about 5% to about 20% RDV, where established.

Preservatives may be used in at least certain embodiments of the food or beverage products disclosed here. That is, at least certain exemplary embodiments can contain an optional dissolved preservative system. Solutions with a pH below 4 and especially those below 3 typically are "microstable," i.e., they resist growth of microorganisms, and so are suitable for longer term storage prior to consumption without the need for further preservatives. However, an additional preservative system can be used if desired. If a preservative system is used, it can be added to the product at any suitable time during production, e.g., in some cases prior to the addition of sweeteners. As used here, the terms "preservation system" or "preservatives" include all suitable preservatives approved for use in food or beverage compositions, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives may be used in amounts not exceeding mandated maximum levels under applicable laws and regulations.

In the case of beverages in particular, the level of preservative used can be adjusted according to the planned final product pH and/or the microbiological spoilage potential of the particular beverage formulation. The maximum level employed typically is about 0.05 weight percent of the beverage. It will be within the ability of those skilled in the art, given the benefit of this disclosure, to select a suitable preservative or combination of preservatives for beverage products according to this disclosure.

Other methods of preservation suitable for at least certain exemplary embodiments of the products disclosed here include, e.g., aseptic packaging and/or heat treatment or thermal processing steps, such as hot filling and tunnel pasteurization. Such steps can be used to reduce yeast, mold and microbial growth in the food or beverage products. For example, U.S. Pat. No. 4,830,862 discloses the use of pasteurization in the production of fruit juice beverages as well as the use of suitable preservatives in carbonated beverages. U.S. Pat. No. 4,925,686 discloses a heat-pasteurized freezable fruit juice composition which contains sodium benzoate and potassium sorbate. Both of these patents are incorporated by reference in their entireties. In general, heat treatment includes hot fill methods typically using high temperatures for a short time, e.g., about 190° F. for 10 seconds, tunnel pasteurization methods typically using lower temperatures for a longer time, e.g., about 160° F. for 10-15 minutes, and retort methods typically using, e.g., about 250° F. for 3-5 minutes at elevated pressure, i.e., at pressure above 1 atmosphere.

Suitable antioxidants may be selected from the group consisting of rutin, quercetin, flavonones, flavones, dihydroflavonols, flavonols, flavandiols, leucoanthocyanidins, flavonol glycosides, flavonone glycosides, isoflavonoids, and neoflavonoids. In particular, the flavonoids may be, but not limited to, quercetin, eriocitrin, neoeriocitrin, narirutin, naringin, hesperidin, hesperetin, neohesperidin, neoponcirin, poncirin, rutin, isorhoifolin, rhoifolin, diosmin, neodiosmin, sinensetin, nobiletin, tangeritin, catechin, catechin gallate, epigallocatechin, epigallocatechin gallate, oolong tea polymerized polyphenol, anthocyanin, heptamethoxyflavone, daidzin, daidzein, biochaminn A, prunetin, genistin, glycitein, glycitin, genistein, 6,7,4' trihydroxy isoflavone, morin, apigenin, vitexin, balcalein, apiin, cupressuflavone, datiscetin, diosmetin, fisetin, galangin, gossypetin, geraldol, hinokiflavone, primuletin, pratol, luteolin, myricetin, orientin, robinetin, quercetagetin, and hydroxy-4-flavone.

Suitable food grade acids are water soluble organic acids and their salts and include, for example, phosphoric acid, sorbic acid, ascorbic acid, benzoic acid, citric acid, tartaric acid, propionic acid, butyric acid, acetic acid, succinic acid, glutaric acid, maleic acid, malic acid, valeric acid, caproic acid, malonic acid, aconitic acid, potassium sorbate, sodium benzoate, sodium citrate, amino acids, and combinations of any of them. Such acids are suitable for adjusting the pH of the food or beverage.

Suitable food grade bases are sodium hydroxide, potassium hydroxide, and calcium hydroxide. Such bases also are suitable for adjusting the pH of a food or beverage.

EXAMPLES

Example 1. Synthesis for AcRB

Step 1. Conversion of Rebaudioside A to Rebaudioside B

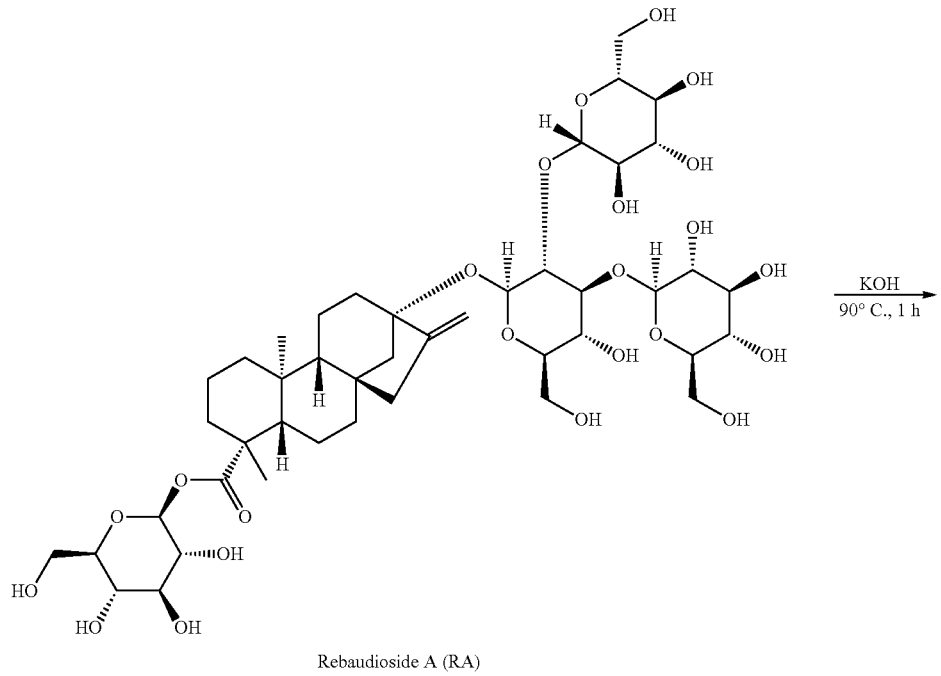

Rebaudioside A (RA)

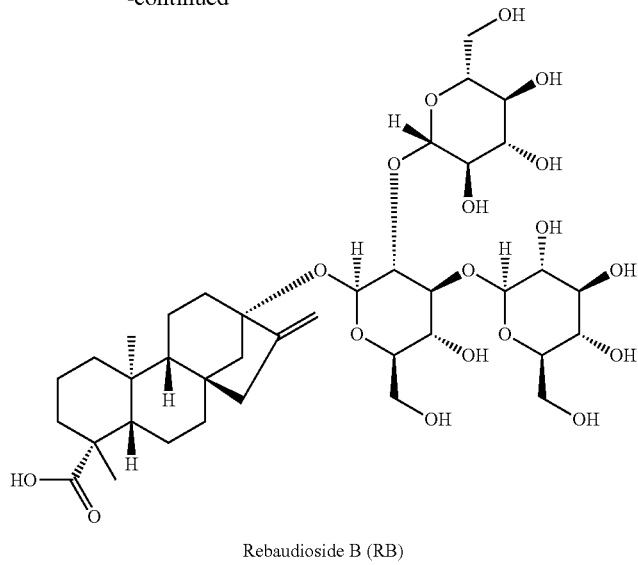

Rebaudioside B (RB)

To a suspension of compound Rebaudioside A (200 g, 1 eq) in H$_2$O (400 mL) was added KOH (23.21 g 2 eq). After addition, the mixture was stirred at 90° C. for 6 h. The reaction mixture was diluted with H$_2$O (400 mL) and adjusted to pH 5 with 12N HCl. The mixture was then filtered and washed with H$_2$O (2000 mL), the organic phase was dried under reduce pressure to give Rebaudioside B (140.0 g, 70% yield) as white solid.

$^1$H NMR (400 MHz, DMSO-d$_6$) δ=5.61 (br d, J=5.1 Hz, 1H), 5.19-5.07 (m, 1H), 5.06-5.06 (m, 1H), 5.07-5.06 (m, 1H), 5.02 (br s, 1H), 4.75 (br s, 1H), 4.65 (br d, J=7.7 Hz, 1H), 4.62-4.56 (m, 1H), 4.53-4.46 (m, 2H), 4.46-4.36 (m, 2H), 4.09 (br s, 2H), 3.73-3.52 (m, 4H), 3.48-3.38 (m, 5H), 3.23-2.98 (m, 11H), 2.98-2.86 (m, 1H), 2.14-1.89 (m, 4H), 1.89-1.64 (m, 5H), 1.55-1.38 (m, 4H), 1.35 (br s, 2H), 1.10 (s, 3H), 1.04-0.97 (m, 1H), 0.92 (br d, J=5.3 Hz, 1H), 0.87 (s, 3H), 0.85-0.71 (m, 1H).

Step 2: Preparation of AcRB

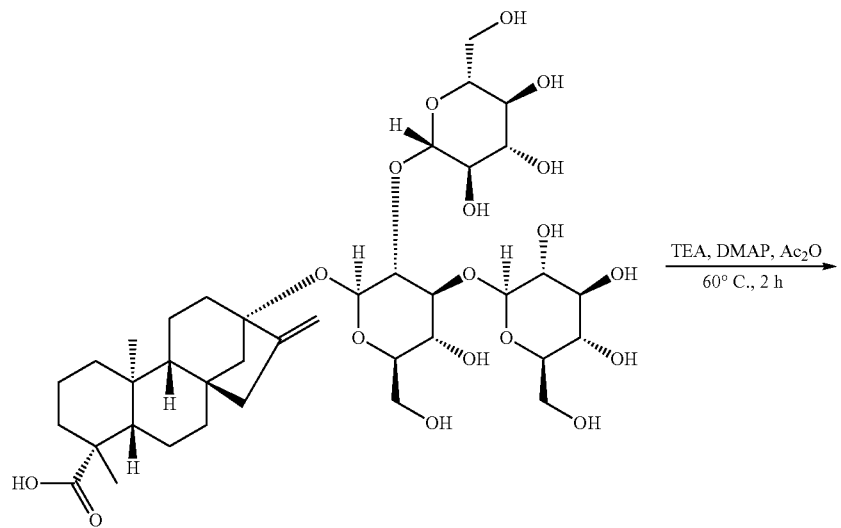

Rebaudioside B (RB)

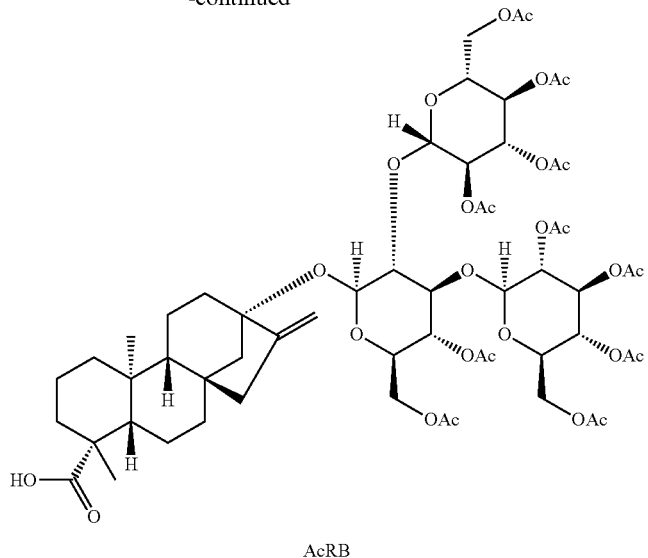

AcRB

To a stirred mixture of Rebaudioside B (38.0 g, 1 eq) in acetic anhydride (88.4 ml, 20 eq) was added sodium acetate (9.3 g, 2.4 eq). The resulting mixture was heated at 140° C. for 2.5 h and then cooled to room temperature. The reaction mixture was then partitioned between water (150 mL) and $CH_2Cl_2$ (200 mL). The organic layer was washed twice with $H_2O$ (150 mL) and once with brine (180 mL), dried over anhydrous $Na_2SO_4$, filtered and concentrated. AcRB was purified from the resulting residue by silica gel chromatography (petroleum ether/ethyl acetate; 33-50%) to give AcRB as white solid (44.0 g, 76% yield).

$^1$H NMR (400 MHz, $CDCl_3$) δ=5.24-5.14 (m, 3H), 5.13-5.04 (m, 2H), 5.01 (s, 2H), 4.92 (d, J=9.3 Hz, 2H), 4.87-4.79 (m, 2H), 4.50 (d, J=7.1 Hz, 1H), 4.43 (dd, J=4.4, 12.3 Hz, 1H), 4.21-3.98 (m, 6H), 3.87 (td, J=9.2, 18.2 Hz, 2H), 3.75-3.62 (m, 2H), 3.56-3.49 (m, 1H), 2.38-1.99 (m, 30H), 1.98-1.72 (m, 6H), 1.69-1.53 (m, 4H), 1.51-1.33 (m, 3H), 1.31-1.21 (m, 4H), 1.14 (dd, J=4.6, 9.5 Hz, 1H), 1.04 (s, 3H), 0.99-0.76 (m, 4H).

Example 2. Synthesis of Rebaudioside B Glycosides

The general Route to Rebaudioside B glycosides is described below.

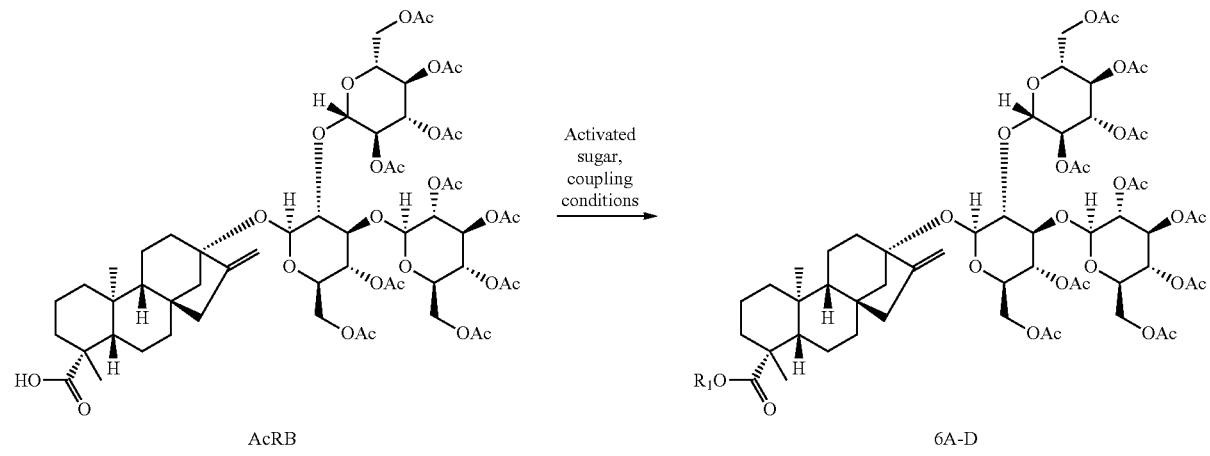

MeONa, MeOH

-continued
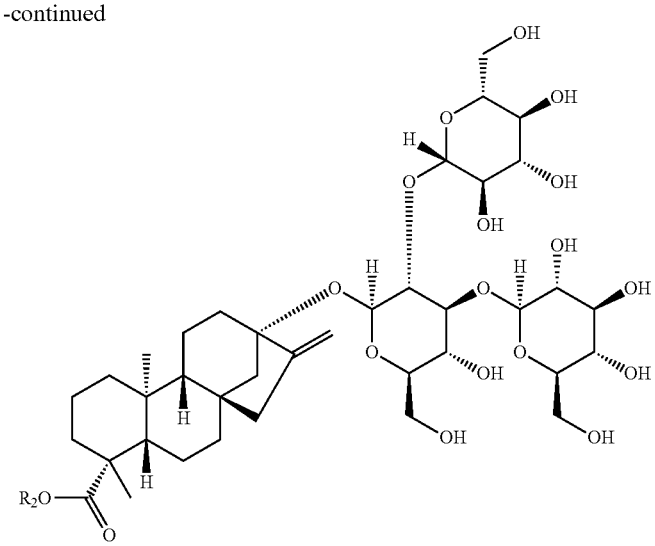
7A-D
Activated Sugars
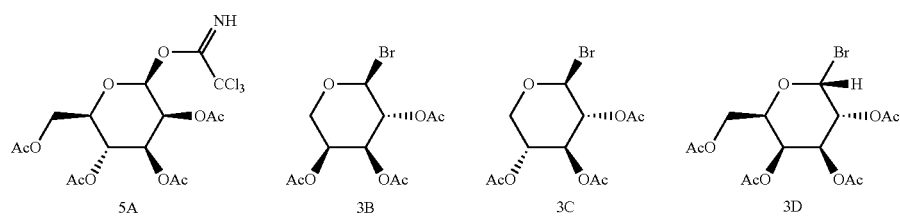
Example 2A. Synthesis of Reb B Mannoside (7A)
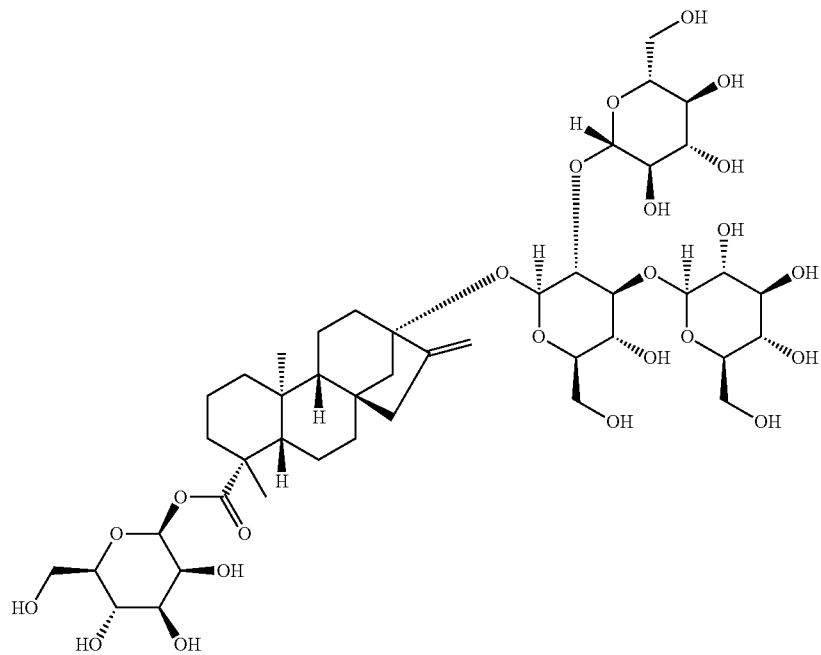

The activated mannose precursor was prepared according to the following synthetic scheme:

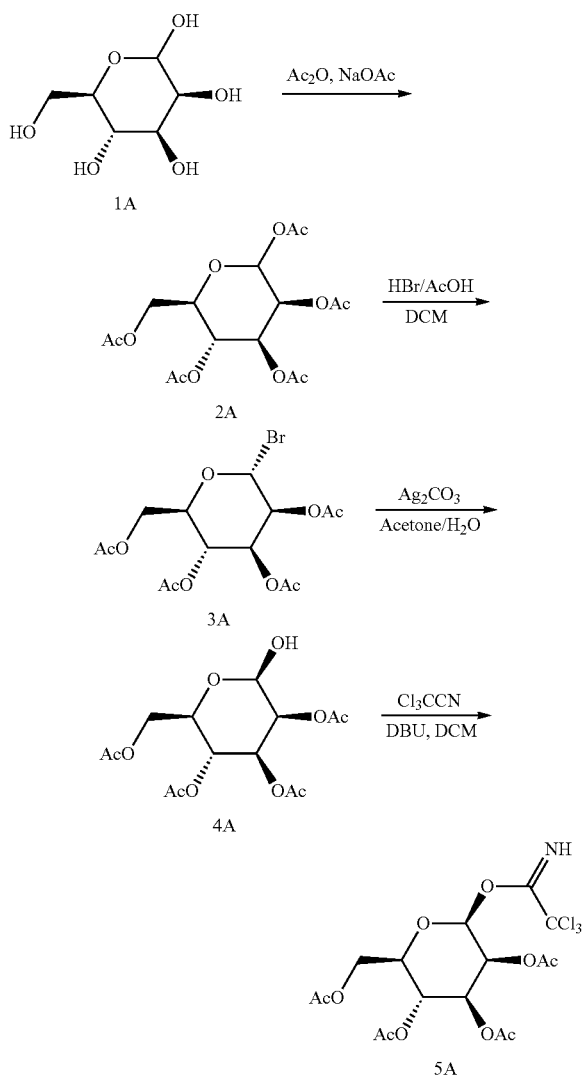

A suspension of D-mannose and sodium acetate (5.46 g, 2.4 eq) in acetic anhydride (56.7 g, 20.0 eq) was stirred under nitrogen at 140° C. for 2.5 h. The reaction mixture was then cooled to rt and poured into a mixture of ice-water (80 mL) and CH$_2$Cl$_2$ (100 mL). The organic layer was separated and washed three times with water (100 mL) and brine (100 mL) and dried over anhydrous Na$_2$SO$_4$. After filtration, the filtrate was concentrated under reduced pressure to give 2A, pentaacetyl-D-mannose (9.5 g, 90% TLC purity, 79% yield) as yellow oil.

HBr (17.9 g, 73.0 mmol, 3.0 eq) was added dropwisely to a solution of 2A (9.5 g, 24.3 mmol, 1.0 eq) in CH$_2$Cl$_2$ (50 mL) over a period of 30 min and the reaction mixture was then stirred at 20° C. for 3 h. The reaction mixture was poured into a mixture of ice-water (100 mL) and CH$_2$Cl$_2$ (120 mL). The organic layer was washed with twice with water (80 mL), aqueous NaHCO$_3$ (150 mL) and brine (150 mL). The organic phase was then dried over anhydrous Na$_2$SO$_4$. Filtration followed by concentration under reduced pressure gave 3A (9.50 g, 85% yield, 90% TLC purity) as yellow oil.

To the solution of 3A (9.5 g, 1.0 eq) in acetone (100 mL) and H$_2$O (5 mL) at rt was added Ag$_2$CO$_3$ (13.2 g, 1.3 eq) portion-wise and the reaction mixture was stirred for 3 h. The mixture was then filtered through a bed of Celite and the filtrate was concentrated under reduced pressure to afford 4A (8.30 g, 93% yield) as yellow oil.

DBU (653 mg, 0.20 eq) was added to the solution of Cl$_3$CCN (31.6 g, 10 eq) and 4A (8.3 g, 1 eq) in DCM (100 mL). The reaction mixture was stirred at 20° C. for 3 h. TLC showed the reaction was completed. TLC information: R$_{f(TM)}$=0.60, PE:EA=2:1. The reaction mixture was filtered off and the solvent of the filtrate were evaporated under reduced pressure to afford residue. The residue was purified by column 33-50% ethyl acetate in petroleum ether to give 5A (6.0 g, $^1$H NMR purity 90%, 56.8% yield) as colorless oil.

$^1$H NMR (400 MHz, CDCl$_3$) δ=8.79 (s, 1H), 6.29 (d, J=1.8 Hz, 1H), 5.50-5.46 (m, 1H), 5.42 (d, J=1.3 Hz, 2H), 4.27 (d, J=4.6 Hz, 1H), 4.19 (s, 1H), 4.17-4.09 (m, 1H), 2.21 (s, 3H), 2.09 (d, J=6.8 Hz, 6H), 2.02 (s, 3H).

Trichloroacetimidate 5A (4.0 g, 1.0 eq) and AcRB (1.77 g, 1.10 eq) were dissolved in DCM (100.00 mL) in the presence of 4A molecular sieves (1.60 g). The reaction mixture was stirred at 20° C. for 30 min. The mixture was then cooled to −40° C. and TMSOTf (217.37 mg, 0.30 eq) was added and the reaction mixture was stirred at −40° C. for 20 min. The reaction mixture was then quenched by added triethylamine dropwise. The mixture was filtered, and the filtrate was evaporated under reduced pressure to afford an oil from which peracetylated Reb B mannoside was purified by column (50% ethyl acetate in petroleum ether) as white solid (3.50 g, 41% yield).

$^1$H NMR (400 MHz, CDCl$_3$) δ=6.10 (s, 1H), 5.30 (s, 4H), 5.23-5.14 (m, 3H), 5.10 (br s, 3H), 4.99 (br s, 2H), 4.97-4.88 (m, 2H), 4.84 (br d, J=14.6 Hz, 2H), 4.60-4.47 (m, 1H), 4.46-4.38 (m, 1H), 4.29-4.21 (m, 1H), 4.09 (br s, 7H), 3.98-3.92 (m, 1H), 3.91-3.77 (m, 2H), 3.75-3.43 (m, 3H), 2.36-1.97 (m, 42H), 1.94-1.73 (m, 8H), 1.70-1.40 (m, 5H), 1.30-1.22 (m, 3H), 1.19-0.94 (m, 5H), 0.90 (s, 2H).

To the solution of peracetylated Reb B mannoside (1.7 g, 1.0 eq) in CH$_3$OH (15 mL) was added NaOCH$_3$ (53 mg, 1 eq) and stirred at 20° C. for 3 h. The reaction mixture was adjusted to pH 5 by dropwise addition of aqueous HCl solution and a precipitate resulted. The mixture was filtered, washed by three times with CH$_3$OH and dried under reduced pressure to afford a white solid. The solid was suspended in EtOH (6 mL) and filtered, the solid was then lyophilized from EtOH/H$_2$O (1 mL/6 mL) twice to give desired product Rebaudioside B Mannoside as white solid (420 mg, 43% yield).

$^1$H NMR (400 MHz, DMSO-d$_6$) δ=5.67-5.54 (m, 1H), 5.30-5.19 (m, 1H), 5.15-5.07 (m, 2H), 5.06-4.94 (m, 4H), 4.89 (br s, 1H), 4.77-4.53 (m, 7H), 4.52-4.38 (m, 3H), 4.09 (br t, J=5.6 Hz, 1H), 3.68 (br s, 3H), 3.64-3.58 (m, 1H), 3.56-3.48 (m, 3H), 3.42 (br dd, J=5.4, 11.8 Hz, 7H), 3.23-3.11 (m, 5H), 3.10-2.93 (m, 5H), 2.14-1.98 (m, 4H), 1.96-1.62 (m, 6H), 1.54-1.40 (m, 4H), 1.36 (br d, J=10.4 Hz, 2H), 1.13 (s, 3H), 1.08-0.90 (m, 3H), 0.90-0.84 (m, 3H), 0.78 (br s, 1H). LCMS (Method E, see Table 1 below, ES-API, Negative Scan, m/z), 965.7, 803.6, and 401.2. HPLC retention time, 2.459 minutes, purity by HPLC area, 97.96%.

TABLE 1

LC MS Method E

| | |
|---|---|
| Method name: | Method E |
| Instrument: | Agilent 1200 & 6110A |
| Column: | Xbridge Shield RP18 2.1*50 mm, 5 um |
| Column temperature: | 40° C. |
| Mobile phase A(MPA) | H2O + 10 mM NH4HCO3 |
| Mobile phase B(MPB) | Acetonitrile |
| Flow rate: | 0.8 mL/min |

TABLE 1-continued

LC MS Method E

| Gradient Ratio: | Time (min) | | | | | |
|---|---|---|---|---|---|---|
| | | 0.00 | 0.40 | 3.40 | 3.85 | 3.86 | 4.50 |
| | MPA (%) | 95 | 95 | 10 | 0 | 95 | 95 |
| | MPB (%) | 5 | 5 | 90 | 100 | 5 | 5 |
| Detection: | 220 nm | | | | | |
| MS Mode: | Negative | | | | | |
| MS Range: | 100-1000 | | | | | |

Example 2B. Synthesis of Rebaudioside B Arabinoside (7B)

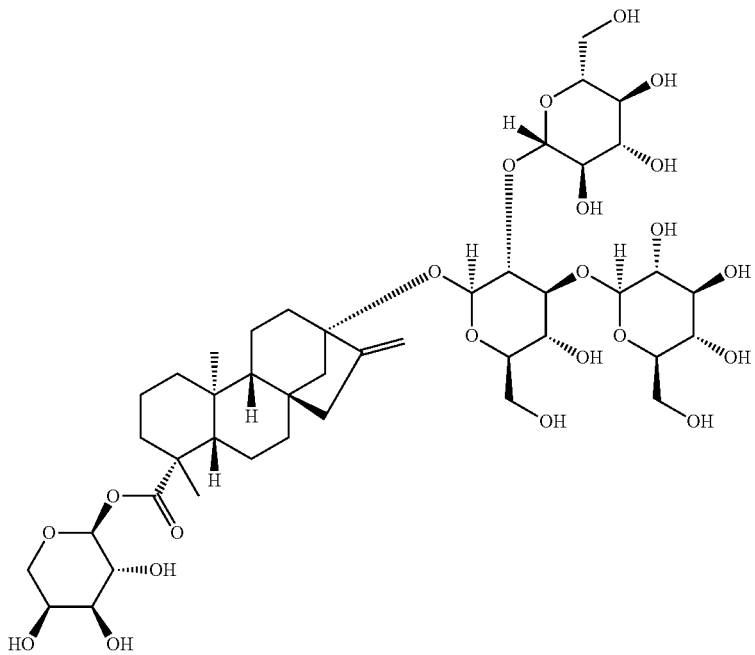

Step 1: Preparation of Compound 6B

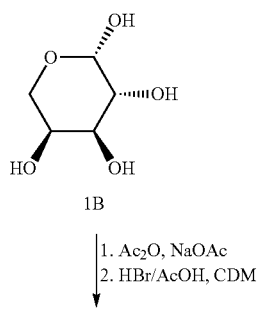

1B

1. Ac$_2$O, NaOAc
2. HBr/AcOH, CDM

-continued

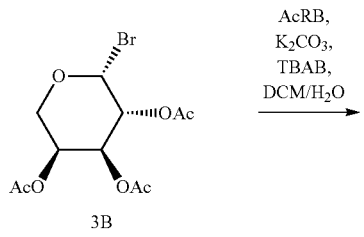 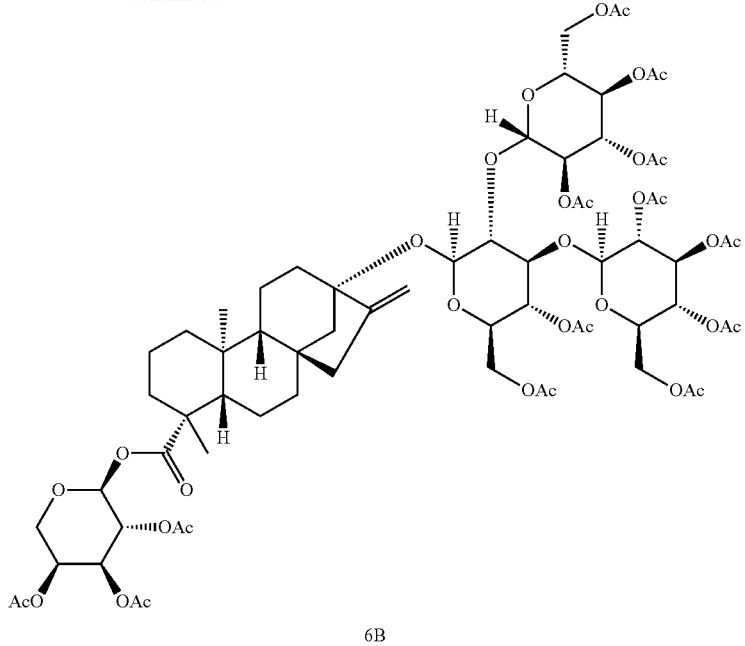

3B was prepared according to procedures described for preparation of 3A.

$^1$H NMR (400 MHz, CDCl$_3$) δ=6.74-6.66 (m, 1H), 5.39 (s, 1H), 5.11-5.05 (m, 1H), 4.21 (d, J=13.6 Hz, 1H), 3.93 (dd, J=1.3, 13.3 Hz, 1H), 2.15 (s, 3H), 2.11 (s, 3H), 2.03 (s, 3H).

The compound AcRB (1.00 g, 1.00 eq) and 3B (332.16 mg, 1.20 eq) were dissolved in the mixture of DCM (20.00 mL) and Water (20.00 mL). Then K$_2$CO$_3$ (169.20 mg, 1.50 eq) and TBAB (263.11 mg, 1.00 eq) were added. The reaction mixture was heated to reflux (60° C. oil bath) and stirred under N$_2$ protected for 2.5 h. TLC showed the reaction was completed. TLC information: R$_{f(TM)}$=0.15, PE:EA=1:1. The reaction mixture was poured into a mixture of ice-water (30 mL) and DCM (50 mL). The organic layer was washed with water (50 mL*3) and brine (60 mL) subsequently, dried over anhydrous Na$_2$SO$_4$. After filtration, the filtrate was concentrated under vacuum to afford residue. The residue was purified by column (PE/EA=1/1) to give 6B (800.00 mg, 59.47% yield, 90% purity) as white solid.

$^1$H NMR (400 MHz, CDCl$_3$) β=5.72-5.67 (m, 1H), 5.31 (s, 2H), 5.25-5.15 (m, 4H), 5.13-5.04 (m, 3H), 5.03-4.88 (m, 4H), 4.88-4.80 (m, 2H), 4.55 (d, J=7.5 Hz, 1H), 4.46-4.38 (m, 1H), 4.28-4.21 (m, 1H), 4.16-3.99 (m, 6H), 3.97-3.73 (m, 3H), 3.71-3.63 (m, 2H), 3.62-3.55 (m, 1H), 2.24-2.16 (m, 3H), 2.15-1.99 (m, 39H), 1.93-1.75 (m, 5H), 1.71-1.60 (m, 1H), 1.58-1.46 (m, 4H), 1.26 (t, J=7.2 Hz, 3H), 1.20 (s, 2H), 1.10-0.94 (m, 3H), 0.89 (s, 3H), 0.87-0.78 (m, 1H).

Rebaudioside B Arabinoside was prepared from compound 6B according to procedures described for preparation of compound 7A $^1$H NMR (400 MHz, DMSO-d$_6$) δ=5.66 (d, J=5.0 Hz, 1H), 5.37-5.31 (m, 1H), 5.19 (br s, 1H), 5.10 (br s, 2H), 5.03 (br dd, J=4.9, 11.4 Hz, 3H), 4.89 (br d, J=4.8 Hz, 1H), 4.74 (br s, 1H), 4.69 (br d, J=3.8 Hz, 1H), 4.64 (br d, J=7.5 Hz, 2H), 4.59 (br s, 1H), 4.52-4.45 (m, 2H), 4.42 (br d, J=7.8 Hz, 1H), 4.11-4.05 (m, 1H), 3.69 (br s, 1H), 3.66-3.58 (m, 2H), 3.52 (br s, 3H), 3.50-3.36 (m, 6H), 3.33 (s, 4H), 3.23-3.12 (m, 5H), 3.10-3.01 (m, 4H), 3.00-2.91 (m, 1H), 2.13-1.98 (m, 3H), 1.97-1.65 (m, 7H), 1.53-1.42 (m, 4H), 1.40-1.30 (m, 2H), 1.14 (s, 3H), 1.08-1.02 (m, 1H), 0.99-0.89 (m, 2H), 0.85 (s, 3H), 0.81-0.71 (m, 1H). LCMS (Method E, see Table 1, ES-API, Negative Scan, m/z), 935.7, 803.6, and 401.3. HPLC retention time, 2.527 minutes, purity by HPLC area, 100%.

Example 2C. Synthesis of Rebaudioside B Xyloside (7C)

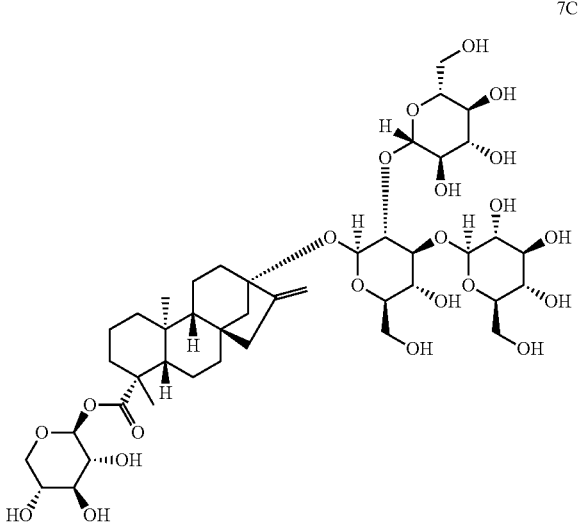

Prepared according to procedures described for preparation of 7B

Compound 6C: $^1$H NMR (400 MHz, CDCl$_3$) δ=5.75 (d, J=6.4 Hz, 1H), 5.24-5.15 (m, 3H), 5.12-5.08 (m, 2H), 5.08-5.04 (m, 2H), 4.99 (s, 2H), 4.98-4.91 (m, 3H), 4.88-4.84 (m, 1H), 4.82-4.79 (m, 1H), 4.60-4.55 (m, 1H), 4.45-

4.39 (m, 1H), 4.26 (dd, J=4.6, 12.3 Hz, 1H), 4.18-4.11 (m, 2H), 4.10 (d, J=3.7 Hz, 2H), 4.07-4.00 (m, 1H), 3.95-3.89 (m, 1H), 3.85-3.79 (m, 1H), 3.71-3.60 (m, 3H), 3.58-3.52 (m, 1H), 2.21-2.15 (m, 3H), 2.14-1.99 (m, 39H), 1.97-1.72 (m, 6H), 1.71-1.59 (m, 2H), 1.58-1.37 (m, 5H), 1.26 (s, 1H), 1.19 (s, 2H), 1.10-1.02 (m, 2H), 1.00-0.95 (m, 1H), 0.86 (s, 3H), 0.84-0.77 (m, 1H).

Compound 7C: $^1$H NMR (400 MHz, DMSO-d$_6$) δ=5.63-5.59 (m, 1H), 5.25 (s, 2H), 5.15-5.10 (m, 1H), 5.08 (br d, J=5.1 Hz, 2H), 5.03-4.99 (m, 3H), 4.96 (d, J=4.4 Hz, 1H), 4.88-4.85 (m, 1H), 4.74 (s, 1H), 4.66-4.62 (m, 2H), 4.58 (s, 1H), 4.51-4.39 (m, 3H), 4.08 (s, 1H), 3.76-3.59 (m, 4H), 3.57-3.47 (m, 2H), 3.46-3.36 (m, 4H), 3.24-3.13 (m, 7H), 3.12-3.02 (m, 5H), 3.01-2.93 (m, 1H), 2.14-1.98 (m, 4H), 1.97-1.83 (m, 2H), 1.80-1.62 (m, 4H), 1.46 (br s, 4H), 1.40-1.28 (m, 2H), 1.12 (s, 3H), 1.08-1.02 (m, 1H), 0.99-0.89 (m, 2H), 0.85 (s, 3H), 0.82-0.71 (m, 1H). LCMS (Method E, see Table 1, ES-API, Negative Scan, m/z), 935.7, 803.6, and 401.3. HPLC retention time, 2.608 minutes, purity by HPLC area, 98.6%.

Example 2D. Synthesis of Rebaudioside B Galactoside (7D)

The title compound 7D was prepared according to procedures described for preparation of 7B.

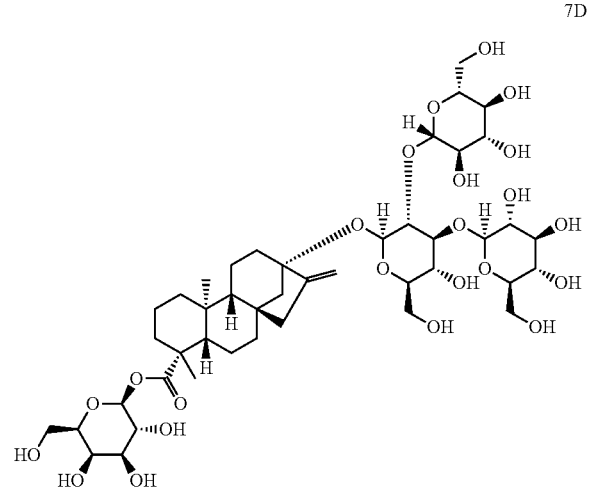

7D

Analytical data for the intermediates and final compounds are shown below.

Compound 3D: $^1$H NMR (400 MHz, CDCl$_3$) δ=6.70 (br d, J=3.5 Hz, 1H), 5.52 (br s, 1H), 5.41 (br dd, J=2.8, 10.5 Hz, 1H), 5.12-5.01 (m, 1H), 4.54-4.42 (m, 1H), 4.25-4.04 (m, 2H), 2.14 (br d, J=14.8 Hz, 6H), 2.07 (s, 3H), 2.02 (s, 3H).

Compound 6D: $^1$H NMR (400 MHz, CDCl$_3$) δ=5.71 (d, J=8.4 Hz, 1H), 5.44 (br s, 1H), 5.37-5.32 (m, 1H), 5.22-5.14 (m, 2H), 5.13-5.04 (m, 4H), 4.99 (s, 4H), 4.87-4.79 (m, 2H), 4.59-4.53 (m, 1H), 4.45-4.37 (m, 1H), 4.29-4.21 (m, 1H), 4.19-4.05 (m, 7H), 4.04-3.98 (m, 1H), 3.96-3.89 (m, 1H), 3.83 (br d, J=7.3 Hz, 1H), 3.71-3.57 (m, 3H), 2.19 (br d, J=2.4 Hz, 3H), 2.14-1.97 (m, 42H), 1.92-1.76 (m, 5H), 1.70-1.59 (m, 1H), 1.57-1.37 (m, 4H), 1.26 (d, J=2.6 Hz, 3H), 1.16 (s, 2H), 1.08-0.94 (m, 3H), 0.84 (s, 3H), 0.83-0.75 (m, 1H).

Compound 7D: $^1$H NMR (400 MHz, DMSO-d$_6$) δ=5.67-5.54 (m, 1H), 5.30-5.19 (m, 1H), 5.15-5.07 (m, 2H), 5.06-4.94 (m, 4H), 4.89 (br s, 1H), 4.77-4.53 (m, 7H), 4.52-4.38 (m, 3H), 4.09 (br t, J=5.6 Hz, 1H), 3.68 (br s, 3H), 3.64-3.58 (m, 1H), 3.56-3.48 (m, 3H), 3.42 (br dd, J=5.4, 11.8 Hz, 6H), 3.23-3.11 (m, 5H), 3.10-2.93 (m, 5H), 2.14-1.98 (m, 4H), 1.96-1.62 (m, 6H), 1.54-1.40 (m, 4H), 1.36 (br d, J=10.4 Hz, 2H), 1.13 (s, 3H), 1.08-0.90 (m, 3H), 0.90-0.84 (m, 3H), 0.78 (br s, 1H). LCMS (Method D, see Table 2, ES-API, Negative Scan, m/z), 965.7, 803.6, and 482.3. HPLC retention time, 2.446 minutes, purity by HPLC area, 98.4%.

TABLE 2

| LC MS Method D | |
|---|---|
| Method name: | Method D |
| Instrument: | Agilent 1200 & 6110A |
| Column: | Xbridge Shield RP18 2.1*50 mm, 5 μm |
| Column temperature: | 40° C. |
| Mobile Phase A (MPA) | H$_2$O + 10 mM NH$_4$HCO$_3$ |
| Mobile Phase B (MPB) | Acetonitrile |
| Flow Rate | 0.8 mL/min |

| Gradient Ratio | | Time (min) | | | | |
|---|---|---|---|---|---|---|
| | 0 | 0.40 | 3.40 | 3.85 | 3.86 | 4.50 |
| MPA % | 95 | 95 | 10 | 0 | 95 | 95 |
| MPB % | 5 | 5 | 90 | 100 | 5 | 5 |

| Detection | 220 nm |
|---|---|
| MS Mode | Negative |
| MS Range | 100-1500 |

Example 2E. Synthesis of Rebaudioside C Xyloside (7E)

The title compound 7E was prepared according to procedures described for preparation of 7B.

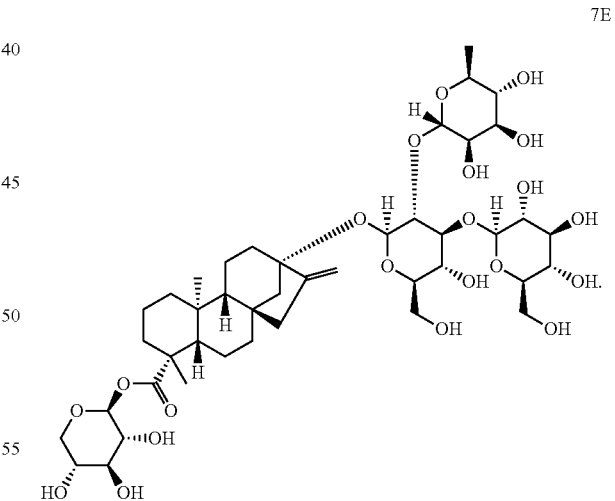

7E

Compound 7E: $^1$H NMR (400 MHz, DMSO-d$_6$) δ: 4.99-5.29 (m, 9H), 4.60-4.74 (m, 5H), 4.43-4.52 (m, 1H), 4.27-4.40 (m, 2H), 3.89-4.07 (m, 2H), 3.52-3.72 (m, 5H), 3.35-3.40 (m, 4H), 3.02-3.20 (m, 10H), 1.77-2.02 (m, 5H), 1.66-1.74 (m, 5H), 1.44-1.47 (m, 3H), 1.32-1.35 (m, 2H), 1.01-1.10 (m, 6H), 0.83-0.90 (m, 5H). LCMS, Method D, see Table 2 (ES-API, Negative Scan, m/z) 920.2, 787.2, 393.1. HPLC retention time, 2.663 minutes, purity by HPLC area, 95.5%.

Example 2F. Synthesis of Rebaudioside C Galactoside (7F)

The title compound 7F was prepared according to procedures described for preparation of 7B

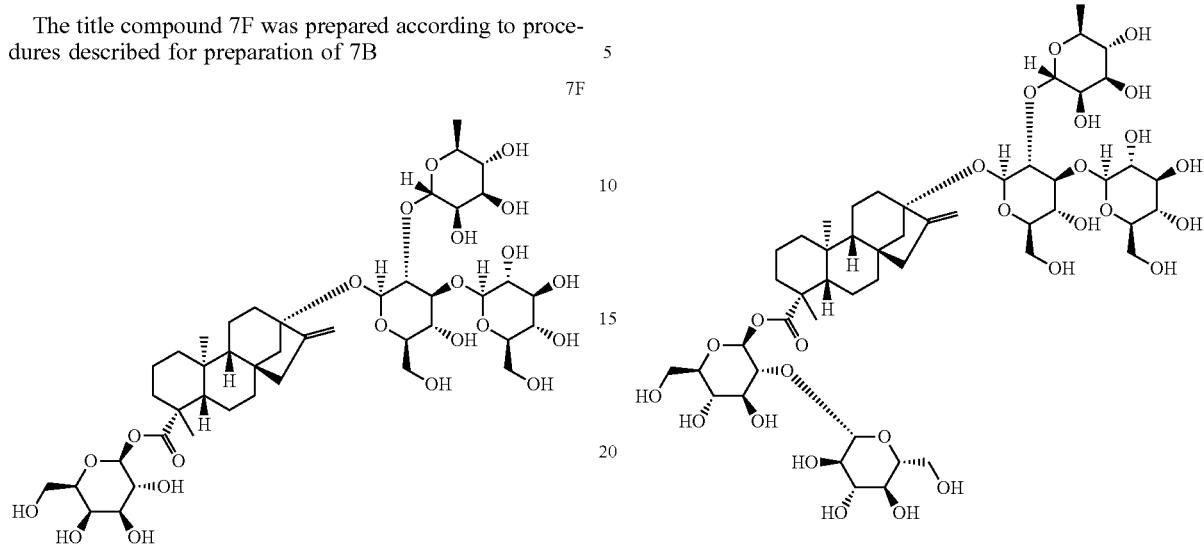

Compound 7F: $^1$H NMR (400 MHz, DMSO-d$_6$) δ: 5.23 (s, 1H), 5.14-5.16 (m, 1H), 4.98 (br s, 1H), 4.73 (br s, 3H), 4.42 (br d, J=7.9 Hz, 1H), 4.29 (br d, J=7.7 Hz, 1H), 3.85-3.96 (m, 1H), 3.40-3.74 (m, 4H), 3.37-3.38 (m, 3H), 3.33-3.35 (m, 10H), 3.01-3.19 (m, 9H), 1.96-2.00 (m, 6H), 1.72-1.75 (m, 4H), 1.64-1.67 (m, 2H), 1.56 (br d, J=11.2 Hz, 1H), 1.37-1.52 (m, 4H), 1.32 (m, 2H), 1.04-1.10 (m, 3H), 0.98-1.03 (m, 6H), 0.83-0.88 (m, 5H). LCMS (Method D, see Table 2) (ES-API, Negative Scan, m/z). 949.3, 787.3. HPLC retention time, 2.513 minutes, purity by HPLC area, 99.86%.

Example 2G. Synthesis of Rebaudioside K (7G)

The title compound 7G was prepared according to procedures described for preparation of 7B.

Compound 7G: $^1$H NMR (400 MHz, DMSO-d$_6$) δ=5.42-5.53 (m, 2H), 5.31 (br. s., 2H), 5.05-5.17 (m, 3H), 4.83-5.04 (m, 4H), 4.74 (d, J=5.48 Hz, 2H), 4.62 (t, J=4.89 Hz, 1H), 4.40-4.58 (m, 5H), 4.18-4.36 (m, 3H), 3.94-4.12 (m, 2H), 3.33-3.77 (m, 16H), 2.81-3.28 (m, 14H), 2.33 (br. s., 2H), 1.93-2.16 (m, 3H), 1.55-1.86 (m, 6H), 1.27-1.54 (m, 5H), 1.17 (s, 3H), 1.08 (d, J=5.87 Hz, 3H), 0.89-1.03 (m, 2H), 0.82 (br. s., 3H). LCMS (Method D, see Table 2) ES-API, Negative Scan, m/z) 1111.2, 5555.1. HPLC retention time, 2.350 minutes, purity by HPLC area, 100%.

Example 3. Synthesis of Reb B Amino Acid Analogs

Reb B Amino Acid Analogs were synthesized according to the general scheme shown below.

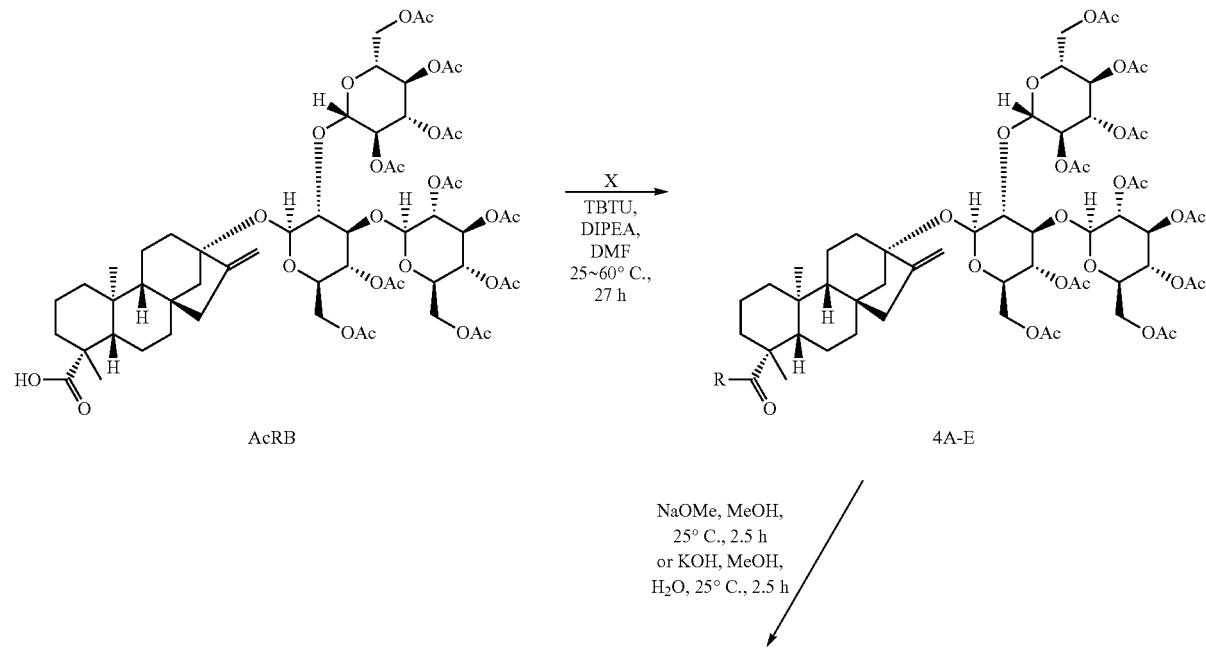

-continued
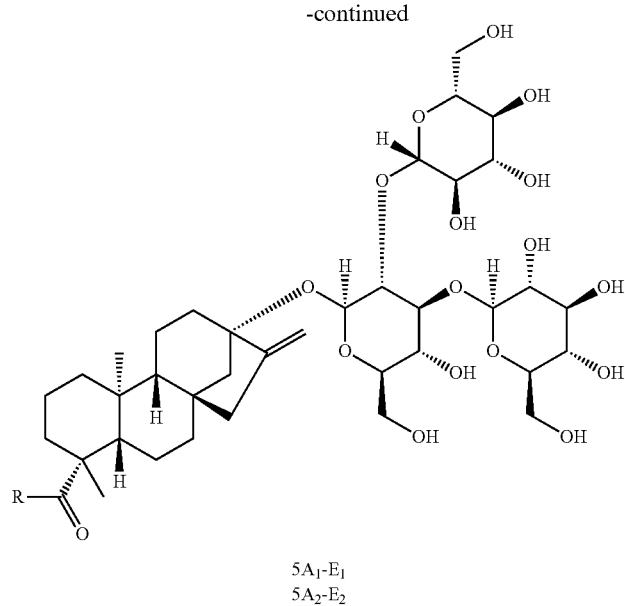
5A₁-E₁
5A₂-E₂
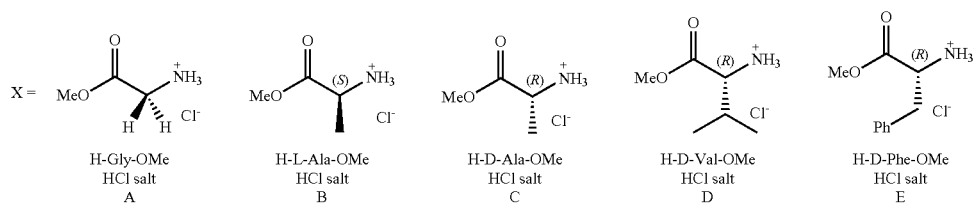
Example Compounds
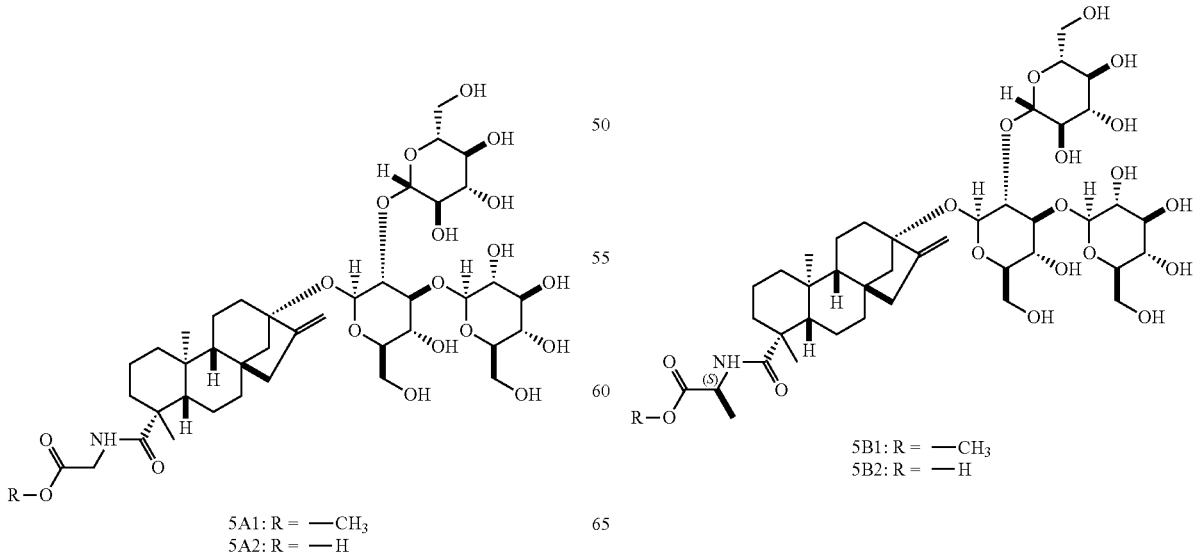

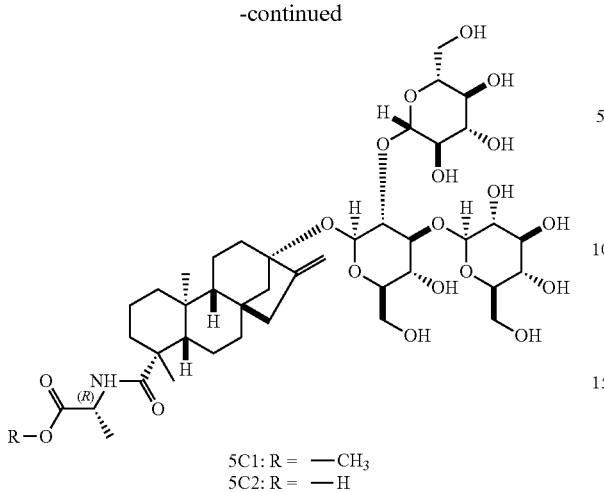

5C1: R = —CH₃
5C2: R = —H

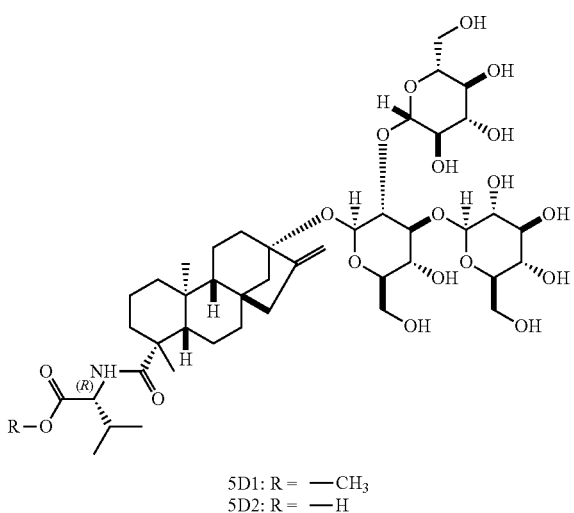

5D1: R = —CH₃
5D2: R = —H

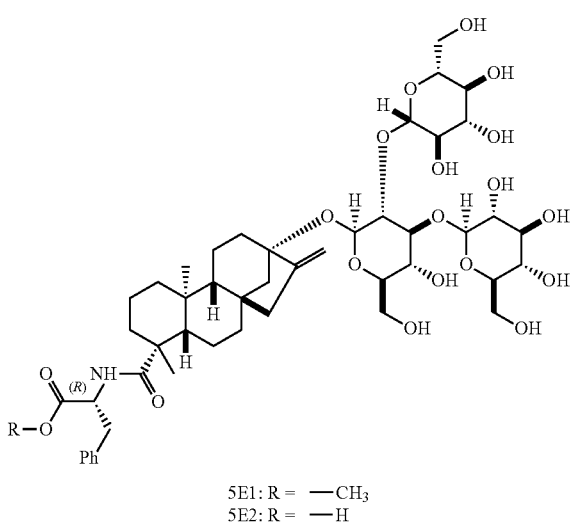

5E1: R = —CH₃
5E2: R = —H

Example 3A. Synthesis of Rebaudioside B—Glycine Methyl ester (5A1)

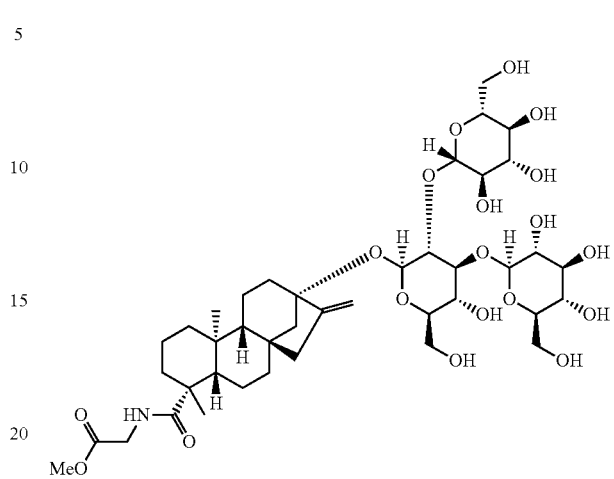

To a suspension of compound AcRB (7.0 g, 1 eq) and glycine methyl ester hydrochloride (4.3 g, 6 eq) in DMF (20 mL) was added DIPEA (5.90 g, 8 eq) and TBTU (2.02 g, 1.1 eq). The reaction mixture was stirred at 25° C. for 4 h and then heated to 60° C. and stirred for 23 h. The reaction was cooled to 25° C. and poured into 100 mL H₂O. The resulting solid was collected by filtration and purified by column chromatography (33-50% ethyl acetate in petroleum ether) to give 4A1 as a yellow solid (700 mg, 9.3% yield).

¹H NMR (400 MHz, CDCl₃) δ=6.24 (d, J=7.0 Hz, 1H), 5.18 (s, 2H), 5.07 (q, J=10.0 Hz, 3H), 5.01-4.95 (m, 2H), 4.92 (d, J=12.5 Hz, 1H), 4.86-4.78 (m, 2H), 4.61-4.50 (m, 2H), 4.45-4.37 (m, 1H), 4.25 (br. s., 1H), 4.21-3.98 (m, 5H), 3.93 (t, J=9.3 Hz, 1H), 3.81 (d, J=7.5 Hz, 1H), 3.79-3.73 (m, 3H), 3.72-3.60 (m, 2H), 3.56-3.48 (m, 1H), 2.26-1.97 (m, 30H), 1.92 (d, J=10.5 Hz, 5H), 1.73-1.42 (m, 7H), 1.41-1.35 (m, 3H), 1.26 (t, J=7.0 Hz, 2H), 1.18 (s, 3H), 1.16-0.94 (m, 3H), 0.94-0.88 (m, 3H), 0.86 (br. s., 1H).

To a stirred solution of compound 4A1 (500 mg, 1 eq) in CH₃OH (4 mL) was added NaOMe (12.50 mg, 0.6 eq) at 25° C. for 2.5 h. CH₃OH was evaporated and the residue was added 2 mL pure H₂O. The reaction mixture was adjusted pH to 2 with 6 N aqueous HCl solution and precipitation generated. The solid was collected by filtration and washed with pure H₂O twice. The solid, 5A1, was lyophilized to afford desire product as a white solid (300 mg, 89% yield). LCMS (Method B, Table 3, ES-API, Positive Scan, m/z), 899.4 and 390.3. HPLC retention time, 2.475 minutes, purity by HPLC area, 97.98%.

TABLE 3

| LC MS Method B | |
|---|---|
| Method name: | Method B |
| Instrument: | Agilent 1200 & 6110A |
| Column: | Luna-C18(2) 2.0*50 mm, 5 μm |
| Column temperature: | 40° C. |
| Mobile Phase A (MPA) | H₂O + 0.037% (v/v) TFA |
| Mobile Phase B (MPB) | Acetonitrile + .018% (v/v) TFA |
| Flow Rate | 0.8 mL/min |

TABLE 3-continued

| LC MS Method B | | | | | | |
|---|---|---|---|---|---|---|
| Gradient Ratio | Time (min) | | | | | |
| | 0 | 0.40 | 3.40 | 3.85 | 3.86 | 4.50 |
| MPA % | 90 | 90 | 0 | 0 | 90 | 90 |
| MPB % | 10 | 10 | 100 | 100 | 10 | 10 |

TABLE 3-continued

| LC MS Method B | |
|---|---|
| Detection | 220 nm |
| MS Mode | Positive |
| MS Range | 100-1000 |

Example 3B. Synthesis of Rebaudioside B—Amino Acid Ester Analogs

Table 4 lists the compounds that were prepared according to procedures described for preparation of 5A1:

TABLE 4

Summary of LCMS Data

| Compound | Structure | LCMS | HPLC Purity (area)/retention time (minutes) |
|---|---|---|---|
| Rebaudioside B-L-Alanine Methyl ester (5B$_1$) | 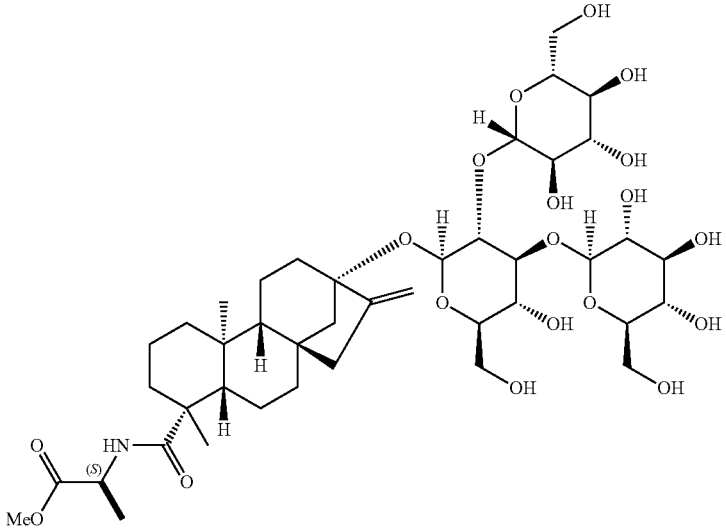 | 912.4 and 404.3 (Method B) | 95.5%/2.555 |
| Rebaudioside B-D-Alanine Methyl ester (5C$_1$) | 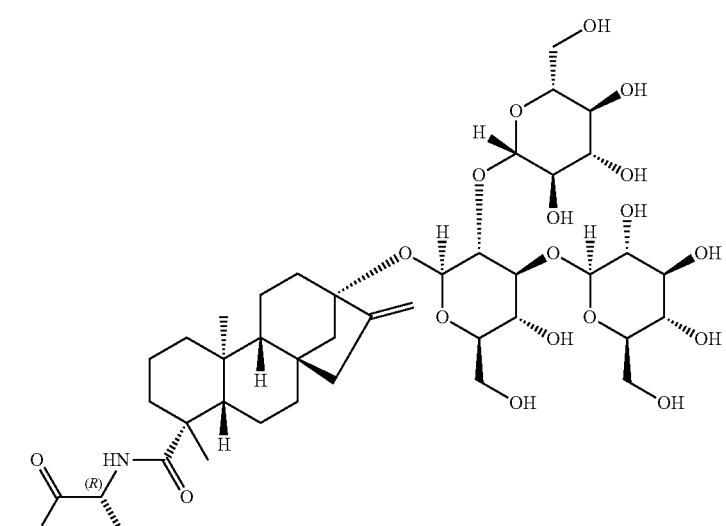 | 912.5 and 404.3 (Method B) | 97.7%/2.547 |

TABLE 4-continued
Summary of LCMS Data
| Compound | Structure | LCMS | HPLC Purity (area)/retention time (minutes) |
|---|---|---|---|
| Rebaudioside B-D-Valine Methyl ester (5D$_1$) | 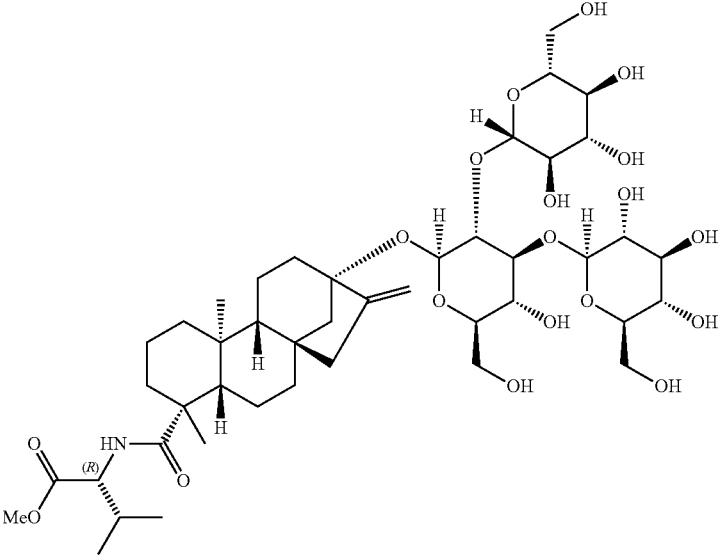 | 940.5 and 432.3 (Method B) | 100%/2.710 |
| Rebaudioside B-D-Phenylalanine Methyl ester (5E$_1$) | 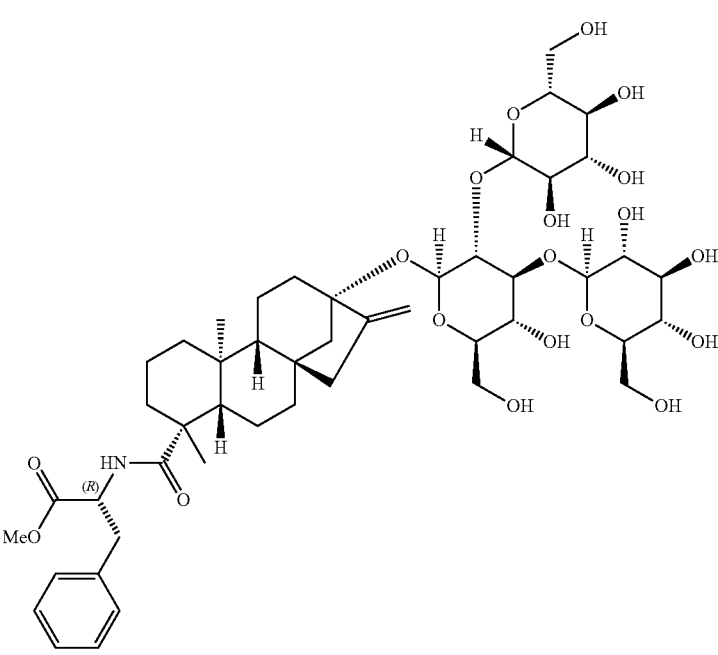 | 480.2 (Method C, Table 5) | 100%/2.649 |

TABLE 5

LC MS Method C

| Method name: | Method D |
|---|---|
| Instrument: | Agilent 1200 & 6110A |
| Column: | Luna-C18(2) 2.0*50 mm, 5 µm |
| Column temperature: | 40° C. |
| Mobile Phase A (MPA) | $H_2O$ + 0.037% (v/v) TFA |
| Mobile Phase B (MPB) | Acetonitrile + .018% (v/v) TFA |
| Flow Rate | 0.8 mL/min |

| Gradient Ratio | | Time (min) | | | | |
|---|---|---|---|---|---|---|
| | 0 | 0.40 | 3.40 | 3.85 | 3.86 | 4.50 |
| MPA % | 90 | 90 | 0 | 0 | 90 | 90 |
| MPB % | 10 | 10 | 100 | 100 | 10 | 10 |

| Detection | 220 nm |
|---|---|
| MS Mode | Positive |
| MS Range | 100-1500 |

Example 3C. Synthesis of Rebaudioside B—Rebaudioside B-Glycine (5A2)

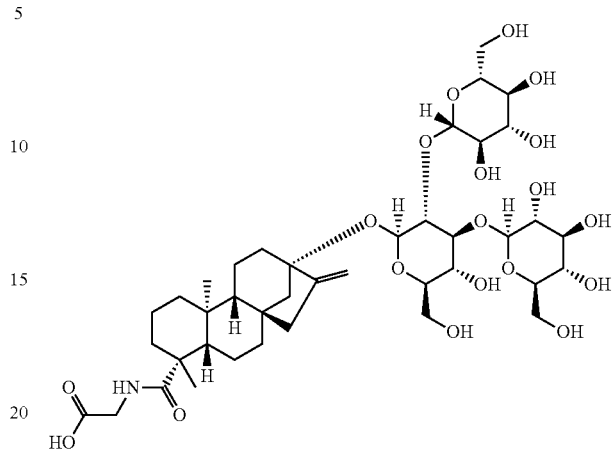

To a stirred solution of compound 4A1 (1.20 g, 1 eq) in $CH_3OH$ (5 mL) and $H_2O$ (5 mL) was added KOH (0.62 g, 12 eq) at 25° C. for 2.5 h. $CH_3OH$ was evaporated and the residue was suspended in $H_2O$ (3 mL). The pH was adjusted to 2 with 6N aq HCl solution and the resulting precipitate was collected by filtration and washed twice with water. The solid was lyophilized to afford desire product as a white solid (316 mg, 40% yield). LCMS (Method C, ES-API, Positive Scan, m/z), 885.2 and 376.3. HPLC retention time, 2.427 minutes, purity by HPLC area, 95.49%. See $^1$H NMR data in Table 7.

Example 3D. Synthesis of Rebaudioside B—Amino Acid Analogs

Table 6 lists the compounds that were prepared according to procedures described for preparation of 5A2:

TABLE 6

Summary of LCMS Data

| Compound | Structure | LCMS | HPLC Purity (area)/retention time (minutes) |
|---|---|---|---|
| Rebaudioside B-L-Alanine (5B$_2$) | 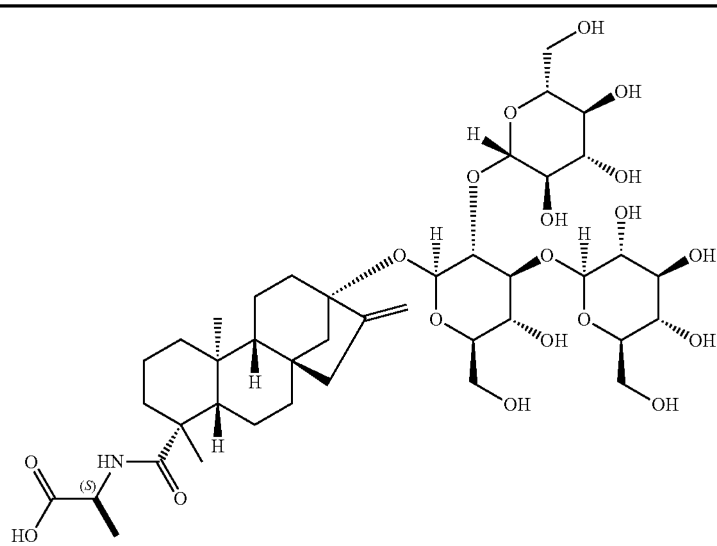 | 898.3 and 390.2 (Method B) | 97.68/2.477 |

TABLE 6-continued

Summary of LCMS Data

| Compound | Structure | LCMS | HPLC Purity (area)/retention time (minutes) |
|---|---|---|---|
| Rebaudioside B-D-Alanine Methyl ester (5C$_2$) | 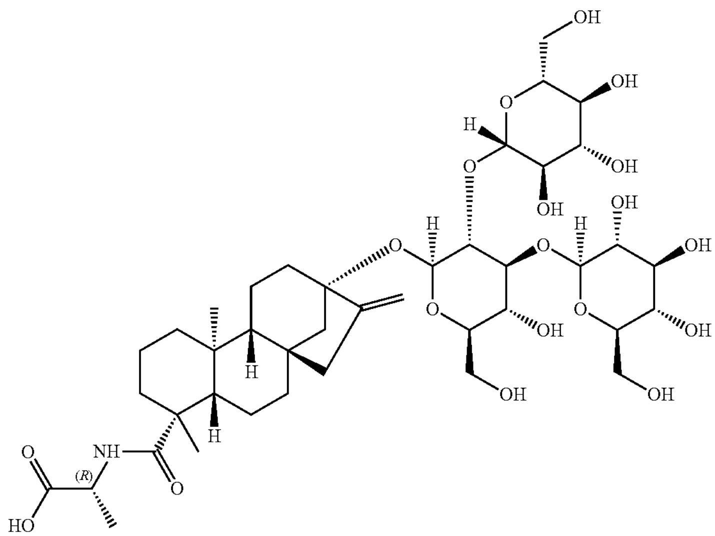 | 898.4 and 390.3 (Method B) | 100%/2.487 |
| Rebaudioside B-D-Valine Methyl ester (5D$_2$) | 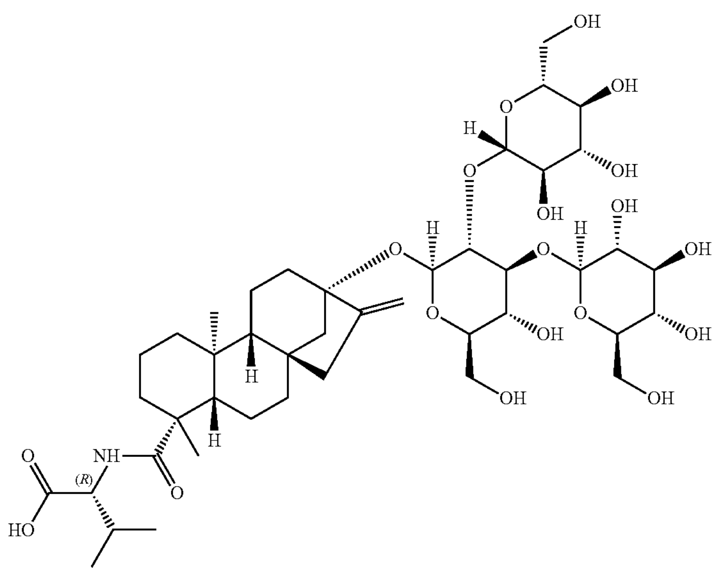 | 902.4 and 450.7 (Method B) | 100%/2.455 |

TABLE 6-continued

Summary of LCMS Data

| Compound | Structure | LCMS | HPLC Purity (area)/retention time (minutes) |
|---|---|---|---|
| Rebaudioside B-D-Phenylalanine Methyl ester (5E$_2$) | 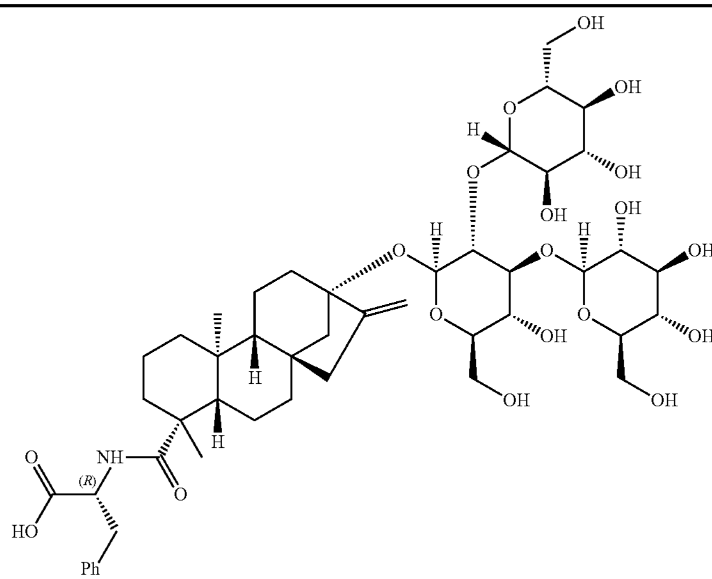 | 950.5 and 474.9 (Method C) | 100%/2.590 |

The $^1$H NMR for compounds 5A1 to 5E1 and 5A2 to 5E2 are shown in Table 7 below.

TABLE 7

Summary of $^1$H NMR

| | |
|---|---|
| Reb-Gly-OCH3 5A1 | $^1$H NMR (METHANOL-d$_4$, 400 MHz): δ = 7.55 (t, J = 5.5 Hz, 1H), 5.27 (br. s., 1H), 4.88 (br. s., 2H), 4.64 (dd, J = 16.3, 7.5 Hz, 2H), 3.80-4.01 (m, 5H), 3.72 (s, 3H), 3.53-3.70 (m, 5H), 3.33-3.45 (m, 4H), 3.03-3.29 (m, 6H), 2.25 (d, J = 11.0 Hz, 1H), 2.02-2.20 (m, 3H), 1.93 (br. s., 5H), 1.76-1.86 (m, 1H), 1.66 (dd, J = 14.1, 7.1 Hz, 1H), 1.50-1.60 (m, 3H), 1.47 (d, J = 11.9 Hz, 2H), 1.19 (s, 3H), 0.98-1.17 (m, 3H), 0.96 (s, 3H), 0.82-0.94 ppm (m, 1H) |
| Reb-L-Ala-OCH$_3$ 5B1 | $^1$H NMR (METHANOL-d$_4$, 400 MHz): δ = 7.29 (d, J = 7.0 Hz, 1H), 5.27 (br. s., 1H), 4.66 (d, J = 7.5 Hz, 2H), 4.39-4.49 (m, 1H), 3.78-3.93 (m, 3H), 3.72 (s, 3H), 3.49-3.70 (m, 5H), 3.33-3.44 (m, 4H), 3.02-3.25 (m, 4H), 2.13 (br. s., 5H), 1.94 (br. s., 7H), 1.54 (d, J = 9.5 Hz, 5H), 1.43-1.51 (m, 2H), 1.40 (d, J = 7.0 Hz, 3H), 1.18 (s, 4H), 0.98-1.14 (m, 3H), 0.95 (br. s., 3H), 0.89 ppm (br. s., 1H) |
| Reb-D-Ala-OCH$_3$ 5C1 | $^1$H NMR (METHANOL-d$_4$, 400 MHz): δ = 5.25 (br. s., 1H), 4.61-4.69 (m, 2H), 4.42 (d, J = 7.5 Hz, 1H), 3.79-3.95 (m, 3H), 3.72 (s, 3H), 3.51-3.70 (m, 4H), 3.33-3.46 (m, 4H), 3.31 (br. s., 6H), 3.06-3.28 (m, 4H), 2.13 (br. s., 4H), 1.76-2.00 (m, 6H), 1.43-1.75 (m, 6H), 1.40 (d, J = 7.5 Hz, 3H), 1.17 (s, 4H), 1.06-1.13 (m, 1H), 1.01 (d, J = 7.5 Hz, 1H), 0.94 (s, 3H), 0.81-0.90 ppm (m, 1H) |
| Reb-D-Val-OCH$_3$ 5D1 | $^1$H NMR (METHANOL-d$_4$, 400 MHz): δ = 6.84 (d, J = 7.5 Hz, 1H), 5.27 (br. s., 1H), 4.91 (br. s., 4H), 4.63-4.73 (m, 2H), 4.33 (t, J = 6.8 Hz, 1H), 3.82-3.98 (m, 3H), 3.77 (s, 3H), 3.56-3.75 (m, 4H), 3.38 (br. s., 3H), 3.30-3.37 (m, 5H), 3.20 (q, J = 9.5 Hz, 3H), 2.06-2.33 (m, 5H), 1.78-2.05 (m, 5H), 1.41-1.77 (m, 6H), 1.13-1.38 (m, 5H), 0.98-1.11 (m, 7H), 0.97 ppm (br. s., 3H) |
| Reb-D-Phe-OCH$_3$ 5E1 | $^1$H NMR (METHANOL-d$_4$, 400 MHz): δ = 7.22-7.37 (m, 5H), 7.06 (d, J = 7.5 Hz, 1H), 5.26 (br. s., 1H), 4.56-4.74 (m, 3H), 3.80-3.96 (m, 3H), 3.76 (s, 3H), 3.56-3.75 (m, 5H), 3.36-3.49 (m, 3H), 3.33 (br. s., 6H), 3.12-3.28 (m, 4H), 3.05 (dd, J = 13.8, 10.3 Hz, 1H), 1.99-2.24 (m, 4H), 1.57-1.97 (m, 6H), 1.23-1.56 (m, 6H), 1.11 (s, 4H), 0.72-1.07 (m, 3H), 0.60 ppm (s, 3H) |
| Reb-Gly 5A2 | $^1$H NMR (METHANOL-d$_4$, 400 MHz): δ = 7.41 (t, J = 5.3 Hz, 1H), 5.29 (br. s., 1H), 4.59-4.69 (m, 2H), 3.94-4.03 (m, 1H), 3.79-3.92 (m, 4H), 3.51-3.76 (m, 5H), 3.33-3.45 (m, 4H), 3.07-3.28 (m, 4H), 2.20-2.30 (m, 1H), 2.13 (br. s., 3H), 1.85-2.05 (m, 6H), 1.80 (br. s., 1H), 1.36-1.74 (m, 7H), 1.19 (s, 6H), 0.78-1.05 ppm (m, 6H) |

TABLE 7-continued

Summary of $^1$H NMR

| | |
|---|---|
| Reb-L-Ala 5B2 | $^1$H NMR (METHANOL-$d_4$, 400 MHz) δ = 7.21-7.12 (m, 1H), 5.27 (br. s., 1H), 4.64 (dd, J = 7.5, 15.6 Hz, 2H), 4.44-4.34 (m, 1H), 3.89 (d, J = 10.5 Hz, 1H), 3.83 (dd, J = 6.5, 10.0 Hz, 2H), 3.72 (s, 1H), 3.64 (d, J = 6.0 Hz, 4H), 3.44-3.39 (m, 1H), 3.39-3.33 (m, 3H), 3.29-3.08 (m, 6H), 2.28-2.01 (m, 5H), 1.93 (br. s., 5H), 1.86-1.75 (m, 1H), 1.73-1.60 (m, 1H), 1.60-1.44 (m, 5H), 1.41 (d, J = 7.5 Hz, 3H), 1.18 (s, 4H), 1.14-0.98 (m, 3H), 0.95 (s, 3H), 0.92-0.82 (m, 1H) |
| Reb-D-Ala 5C2 | $^1$H NMR (METHANOL-$d_4$, 400 MHz) δ = 7.12 (d, J = 7.5 Hz, 1H), 5.34 (br. s., 1H), 4.73-4.61 (m, 2H), 4.55-4.43 (m, 1H), 3.85 (s, 3H), 3.80-3.54 (m, 6H), 3.48-3.37 (m, 6H), 3.19 (d, J = 9.0 Hz, 1H), 2.18 (br. s., 3H), 2.14-2.04 (m, 2H), 2.04-1.91 (m, 5H), 1.89-1.77 (m, 1H), 1.76-1.64 (m, 2H), 1.63-1.46 (m, 6H), 1.43 (d, J = 7.0 Hz, 3H), 1.22 (s, 3H), 1.20-1.01 (m, 4H), 0.97 (s, 3H), 0.93 (br. s., 1H) |
| Reb-D-Val 5D2 | $^1$H NMR (METHANOL-$d_4$, 400 MHz) δ = 5.36-5.29 (m, 1H), 4.92 (br. s., 2H), 4.67 (d, J = 7.5 Hz, 1H), 4.58 (d, J = 7.5 Hz, 1H), 4.42 (br. s., 1H), 3.81 (br. s., 3H), 3.76-3.46 (m, 7H), 3.45-3.34 (m, 4H), 3.27-3.10 (m, 4H), 2.19 (d, J = 11.0 Hz, 4H), 2.12-1.77 (m, 7H), 1.73-1.39 (m, 6H), 1.21 (s, 4H), 1.07-0.99 (m, 2H), 0.98-0.83 (m, 11H) |
| Reb-D-Phe 5E2 | $^1$H NMR (METHANOL-$d_4$, 400 MHz) δ = 7.32-7.19 (m, 5H), 6.74 (d, J = 7.9 Hz, 1H), 5.33-5.26 (m, 1H), 4.67 (d, J = 7.5 Hz, 1H), 4.56 (d, J = 7.9 Hz, 1H), 3.94-3.78 (m, 3H), 3.75-3.50 (m, 5H), 3.46-3.32 (m, 6H), 3.30-3.17 (m, 6H), 3.10-3.00 (m, 2H), 2.19-2.02 (m, 4H), 2.01-1.57 (m, 7H), 1.56-1.47 (m, 3H), 1.46-1.25 (m, 2H), 1.07 (s, 4H), 1.04-0.72 (m, 4H), 0.70 (s, 3H) |

Example 4. Synthesis of Rebaudioside B—Aspartame

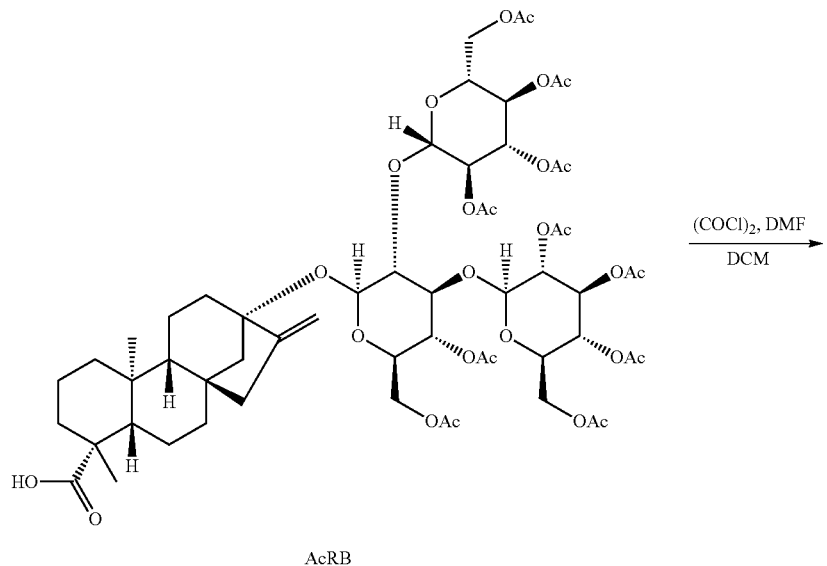

AcRB

-continued
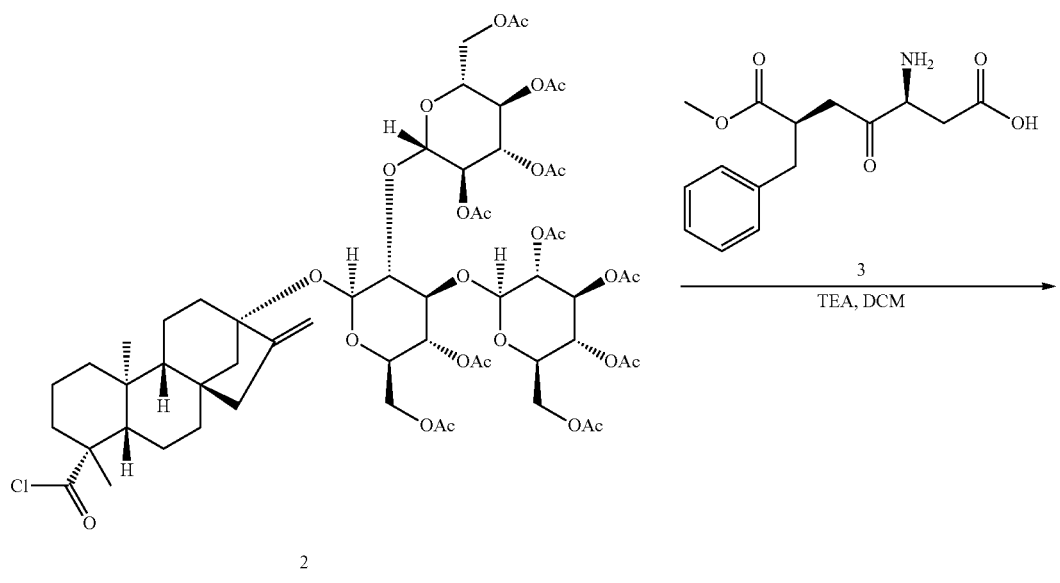
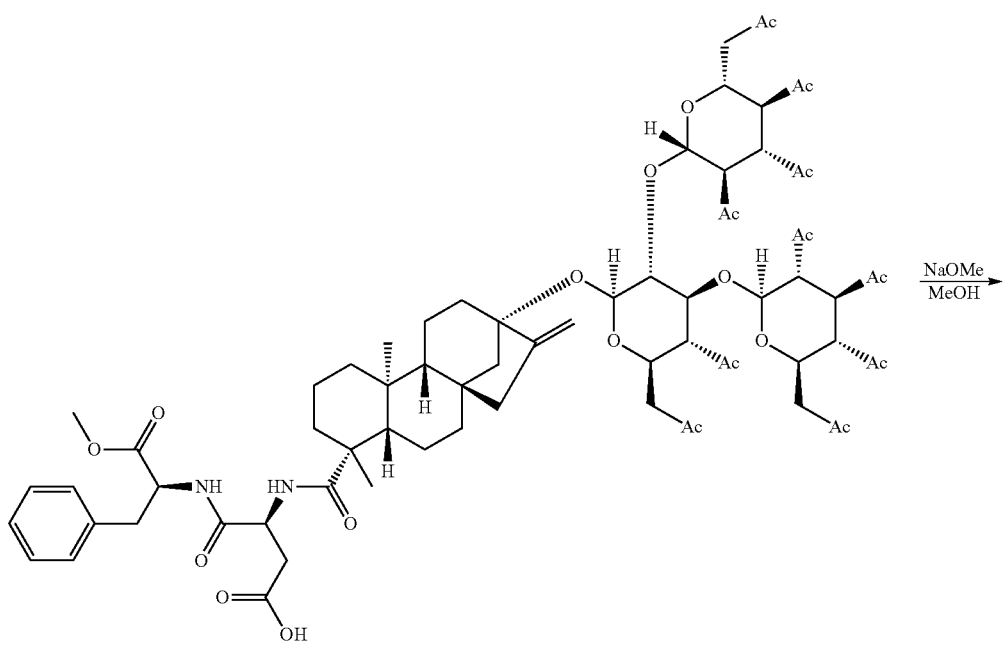

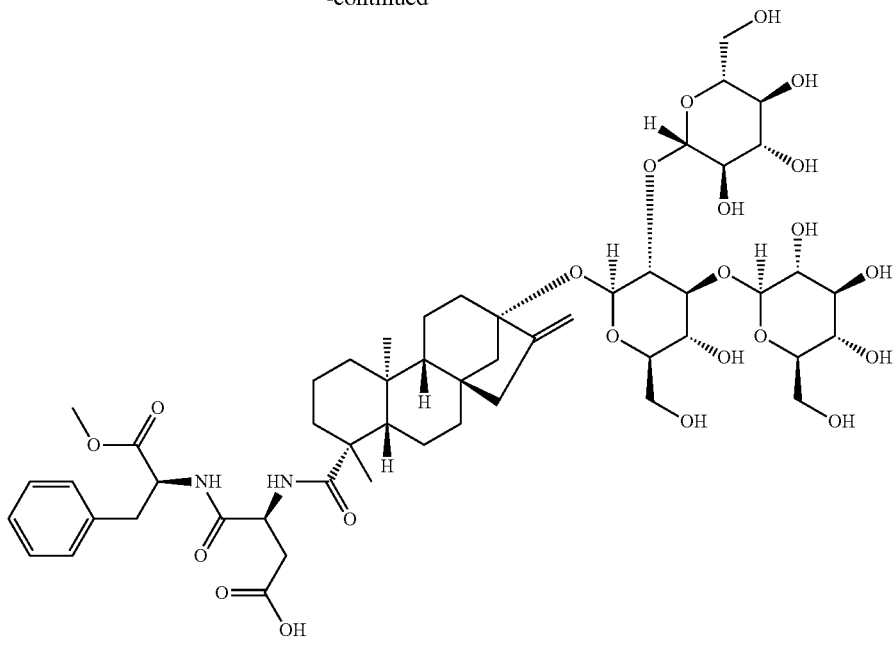

5: Reb B-Aspartame

To a solution of compound AcRB (2.00 g, 1.00 eq) in CH$_2$Cl$_2$ (40.00 mL) at 0° C. was added DMF (11.92 mg, 0.10 eq) and oxalyl chloride (0.31 g, 1.50 eq). The mixture was stirred at 25° C. for 1 h. The solvents were removed under reduced pressure at to give the acid chloride 2 (2.00 g, crude) as white solid which was used directly without further purification.

To a stirred mixture of compound 2 (3.00 g, 1.00 eq) and triethylamine (0.24 g, 1.00 eq) in CH$_2$Cl$_2$ (120 mL) was added 3 (2.13 g, 3.00 eq). The mixture was stirred at 25° C. for 14 h and then filtered and concentrated. The residue was purified by column chromatography (CH$_2$Cl$_2$: MeOH=20/1) and further purified by prep-HPLC to give product 4 (2.00 g, 55.14% yield, 95.72% purity) as white solid.

A suspension of 4 (1.00 g, 1.00 eq) and NaOMe (143.91 mg, 4.00 eq) in MeOH (10.00 mL) was stirred at 25° C. for 19 h. The solvent was then concentrated to about 4 mL and the pH was adjusted to 5 with aqueous 1M HCl. Water (10 mL) was added and a stream of nitrogen gas was passed through the mixture for 10 min. The mixture was then freeze-dried. The resulting crude material was purified by prep-HPLC. The resulting off-white solid was then passed through ion-exchange resin and lyophilized twice to give 5 (250 mg, 34.7% yield) as white solid.

$^1$H NMR (400 MHz, MeOH-d$_4$) δ=7.28 (s, 5H), 5.23-5.19 (m, 1H), 4.85-4.85 (m, 1H), 4.87 (s, 2H), 4.73-4.62 (m, 4H), 3.93-3.88 (m, 1H), 3.87-3.81 (m, 2H), 3.77 (br s, 1H), 3.73-3.72 (m, 1H), 3.71 (s, 1H), 3.69 (s, 3H), 3.68-3.62 (m, 3H), 3.61-3.55 (m, 1H), 3.44-3.35 (m, 4H), 3.35-3.33 (m, 1H), 3.29 (s, 2H), 3.23-3.10 (m, 3H), 3.09-3.01 (m, 1H), 2.88-2.67 (m, 2H), 2.25-1.97 (m, 5H), 1.96-1.73 (m, 6H), 1.72-1.50 (m, 4H), 1.48-1.38 (m, 2H), 1.09 (s, 5H), 1.02-0.95 (m, 1H), 0.86 (s, 4H). LCMS (Method D, see Table 2) (ES-API, Positive Scan, m/z), 595.4 and 180.2. HPLC retention time, 2.895 minutes, purity by HPLC area, 95.69%.

Example 5. Sensory Evaluation of Rebaudioside Analogs

General Procedures for Testing Sweet/Flavor Modifying Ingredients

Sweetener

Figure 8:
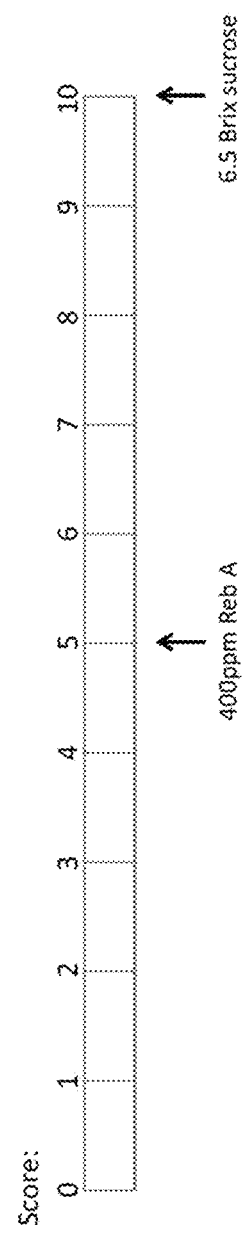
FIG. 8 depicts a graph showing a scale for measuring sweetness.

Sample preparation protocol for testing material as a sweetener: Tasters wore noseclips and were blinded to the identity of the test material. Tasters sampled 400 ppm Rebaudioside A and 6.5 Brix sucrose prior to the test material. Reb A 400 ppm was assigned a 5 on the scale of 1 to 10 as shown in FIG. 8 and sucrose (6.5%) was assigned a 10 on the same scale. Tasters were asked to rinse their mouths 5 times with water between tasting each sample. Tasters were then given the test article and asked to rank the test article for sweetness on the noted scale. Tasters were also asked to provide comments about bitterness, linger, flavors, and any other perceptions.

Numerical scores from all tasters were averaged and, taken together with comments regarding sweet quality, bitterness and off-tastes, converted into the symbols "−," "+," "++," and "+++" to indicate whether a given characteristic was not observed or only minimally observed (−) or highly observed (+++). For example, a sample having a "−" in both sweet intensity and bitterness should be understood as a sample having minimal or no sweetness and minimal or no bitter flavor. By contrast, a sample having a "+++" in both sweet intensity and bitterness should be understood as a sample having highly observed sweet intensity and bitterness. This data is summarized in Table 8.

Preparation of Reb A in this experiment: Prepare 400 ppm Reb A in water (pH=7): 40 mg of Rebaudioside A was dissolved with stirring in 100 ml of water at room temperature.

Preparation of Sucrose in this experiment: Prepare 6.5% Sucrose in water (pH=7): weight 6.5 gr of Sucrose and dissolve it in 93.5 gr water (total 100 gr)

Sweetness Enhancement

Sample preparation protocol: For testing the material as a sweet/flavor modifying ingredient, two samples were prepared: a 4° Brix high-fructose corn syrup (HFCS) control solution and a 4° Brix HFCS solution with a known concentration of test ingredient.

Sample Preparation: 4° Brix HFCS control solution was prepared by adding 50.89 grams of 78.60° Brix HFCS to 1000 g phosphoric acid base which was prepared by adding phosphoric acid dropwise into 1 L of Aquafina Water until pH 3.1 was obtained. pH was measured using a METTLER TOLEDO pH meter.

In the case of a different Brix of HFCS starting syrup, the following formula can be used for the amount of HFCS required to make HFCS control solution.

$$4° \text{ Brix}/100 * 1000 \text{ mL}/(78.5° \text{ Brix}/100) = 50.96$$

If any cloudiness persisted, the sample solution was passed through a paper filter. For some low soluble compounds, Branson 2800 Ultra Sonic Bath was used to dissolve the material. If any cloudiness persisted, the sample solution was passed through a paper filter. Solubility was confirmed by shining a laser pointer through the solution. If no diffraction was observed then it was assumed that the material was soluble Forced Choice Test:

12-16 tasters were presented with these two(2) numbered samples: one contained a sweetener such as 4Brix sucrose, 4 Brix high-fructose corn syrup or 200 ppm Rebaudioside A in phosphate buffer. The other sample contained the same plus the test compound at a level, when tested in water, was below 1.5% SEV. Tasters were then asked to taste each sample sequentially with water rinsing before each sample and choose which sample was sweeter.

Sensory Testing for Sweet Enhancement Tasters were asked to not to eat at least 1 hour before tasting and rinse with Aquafina water at least 5 times between tasting all samples. Tasters were given the Forced Choice test as described above. In addition, tasters were asked to note the sweet quality differences between the two samples. Tasters were also asked to comment on sweetness onset, sweetness linger, overall sugarlike sweetness and other qualities such as bitter taste, metallic note, astringency, cooling sensation, any offnotes and any associated flavors. Tasters were also asked to assess sample odor differences and provide any descriptions.

TABLE 8

Summary of Sensory Results

| Compound | Sweet Intensity | Bitterness | Sweet Quality | Enhancement |
|---|---|---|---|---|
| Reb-Gly-OCH$_3$ (5A1) | − | +++ | − | |
| Reb-L-Ala-OCH$_3$ (5B1) | + | +++ | − | |
| Reb-D-Ala-OCH$_3$ (5C1) | ++ | ++ | − | |
| Reb-D-Val-OCH$_3$ (5D1) | − | +++ | − | |
| Reb-D-Phe-OCH$_3$ (5E1) | − | +++ | − | |
| Reb-Gly-OH (5A2) | +++ | + | ++ | +++ |
| Reb-L-Ala-OH (5B2) | ++ | + | + | |
| Reb-D-Ala-OH (5C2) | ++ | + | + | |
| Reb-D-Val-OH (5D2) | +++ | − | + | |
| Reb-D-Phe-OH (5E2) | ++ | − | + | |
| Reb B mannoside (7A) | +++ | + | ++ | |

TABLE 8-continued

Summary of Sensory Results

| Compound | Sweet Intensity | Bitterness | Sweet Quality | Enhancement |
|---|---|---|---|---|
| Reb B arabinoside (7B) | ++ | ++ | + | |
| Reb B xyloside (7C) | +++ | ++ | + | |
| Reb B galactoside (7D) | +++ | − | ++ | ++ |
| Reb C xyloside (7E) | − | − | − | ++ |
| Reb C galactoside (7F) | − | − | − | + |
| Rebaudioside K (7G) | − | − | − | − |
| Sucrose | + | − | +++ | |
| Rebaudioside A | +++ | + | + | |

Sweet quality was based upon a temporal profile (sweet onset, linger) and attributes such as syrupy, round, clean.

Rebaudioside B Galactoside Sweet Enhancement:

Trained Sensory panelists (n=25, 3 evaluations each) evaluated Reb B Galactoside in aqueous phosphoric acid (pH 3.1) at room temperature. Rebaudioside B galactoside is not currently approved for use in food or beverages in the United States. Therefore, every person who tasted the samples signed an informed consent form provided by PepsiCo Scientific Affairs before tasting samples. Participation in the tests was completely voluntary. Panelists who chose to participate could choose to stop participation at any time.

Sucrose Equivalence Value:

In order for a test ingredient to be considered an enhancer, it must not be considered a sweetener. A paired comparison with 1.5% sucrose was used to determine that 25 ppm of Rebaudioside B Galactoside was significantly (p<0.0001) less sweet than 1.5% sucrose.

Figure 2:
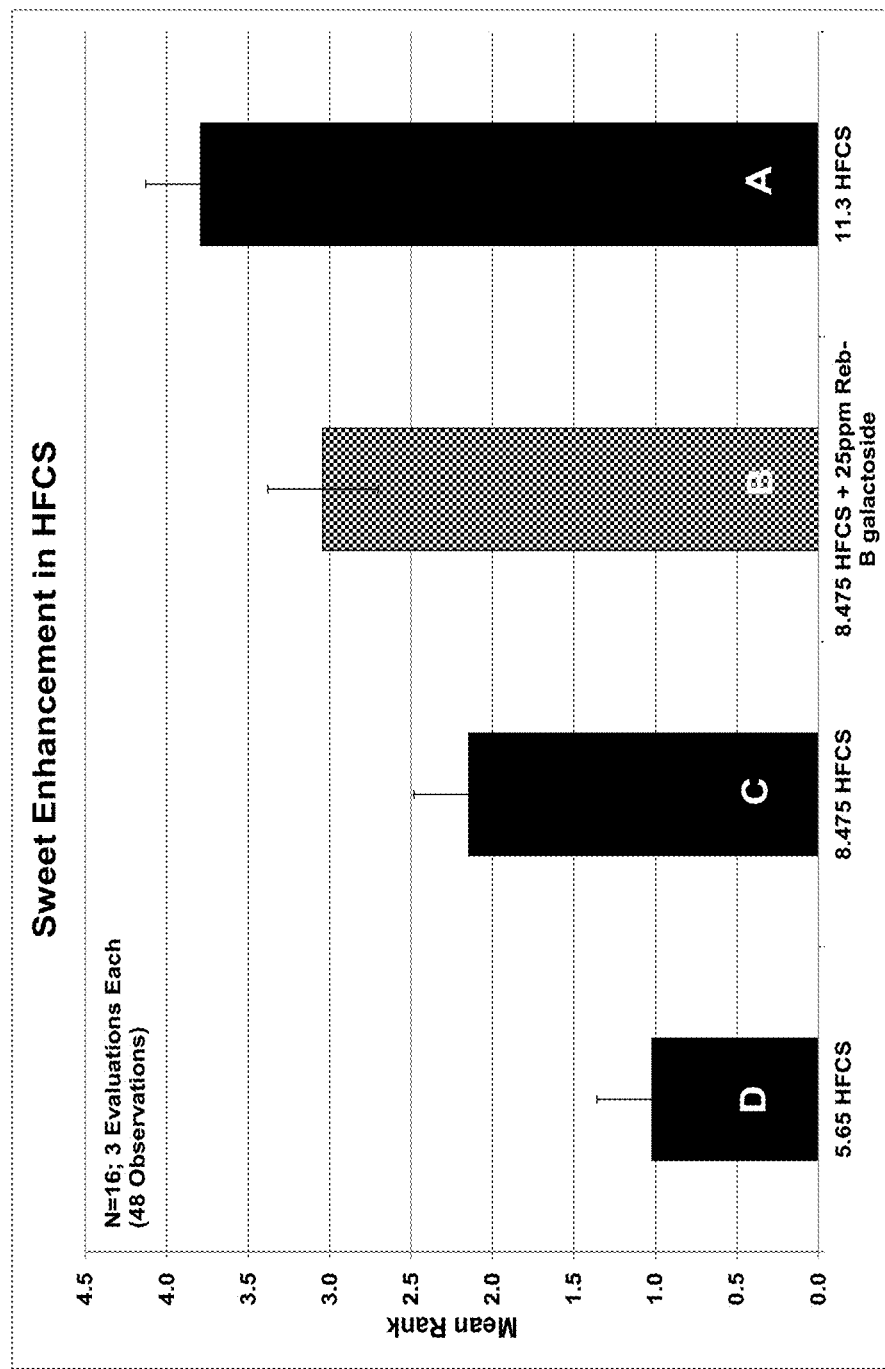
FIG. 2 depicts bar graphs showing that adding 25 ppm of Reb B galactoside to High-Fructose Corn Syrup (HFCS) enhances the sweetness of the HCFS.
Figure 3:
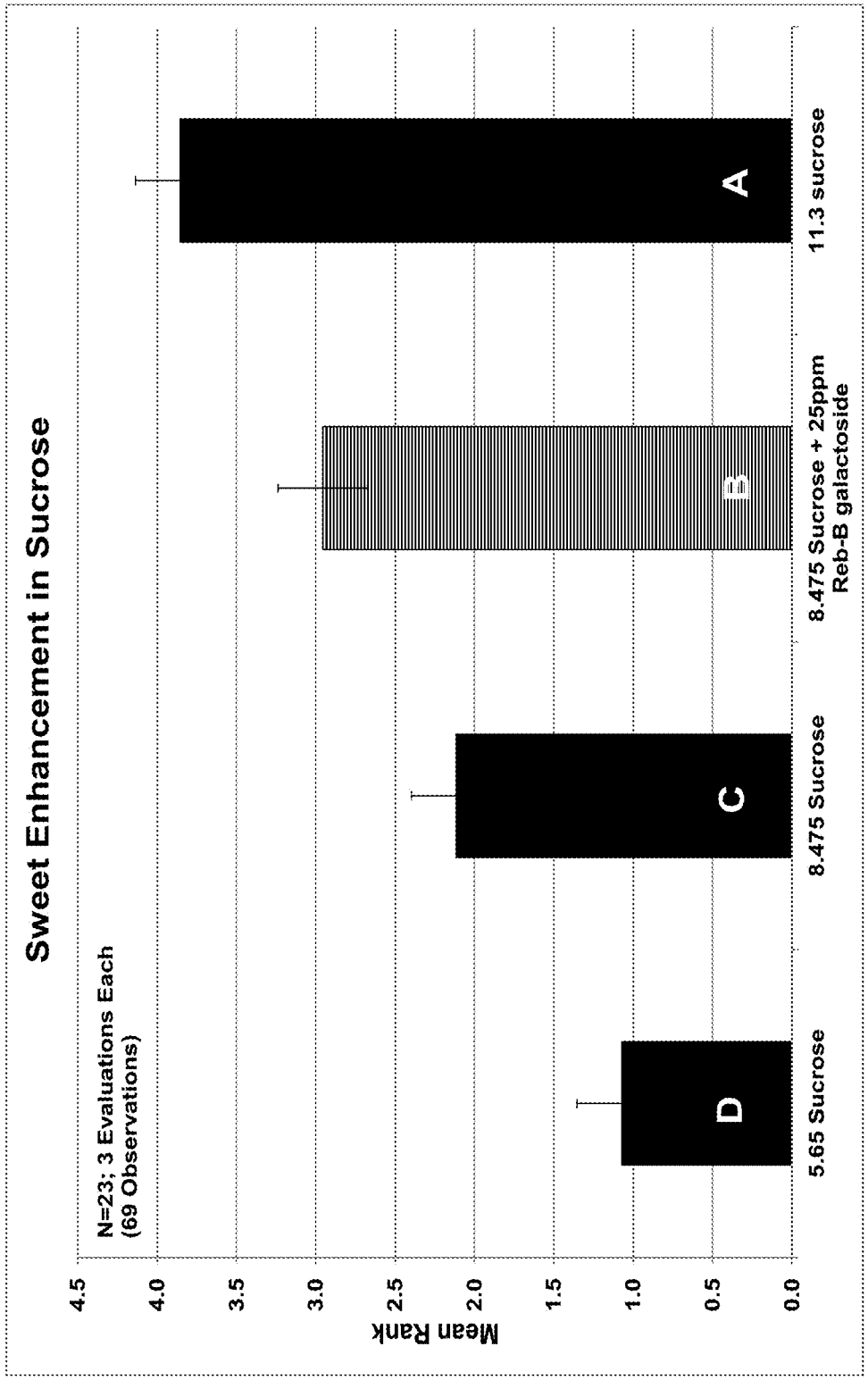
FIG. 3 depicts bar graphs showing that adding 25 ppm of Reb B galactoside to sucrose enhances the sweetness of the sucrose.
Figure 4:
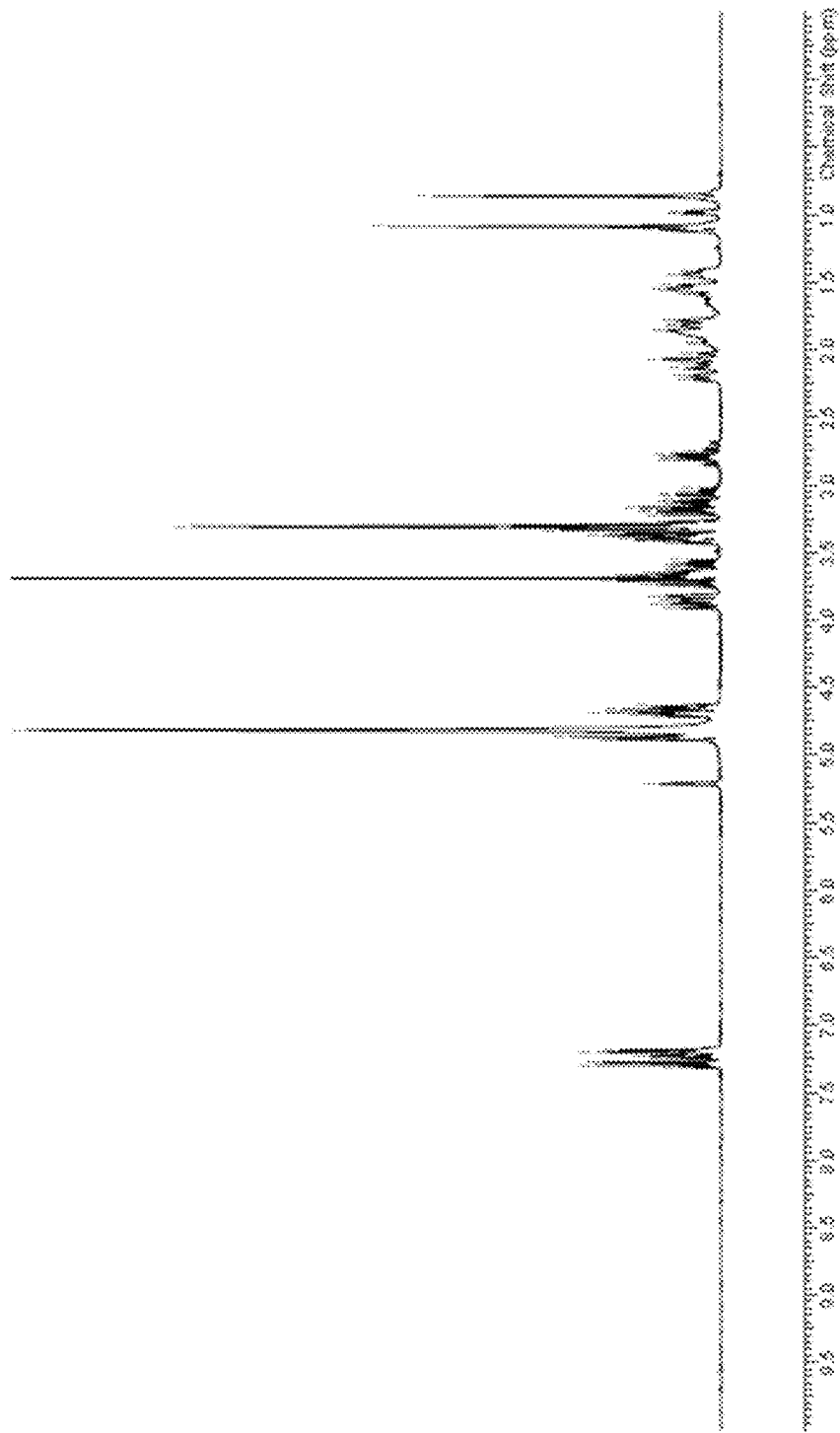
FIG. 4 is $^1$HNMR spectrum of compound 5.
Figure 5A:
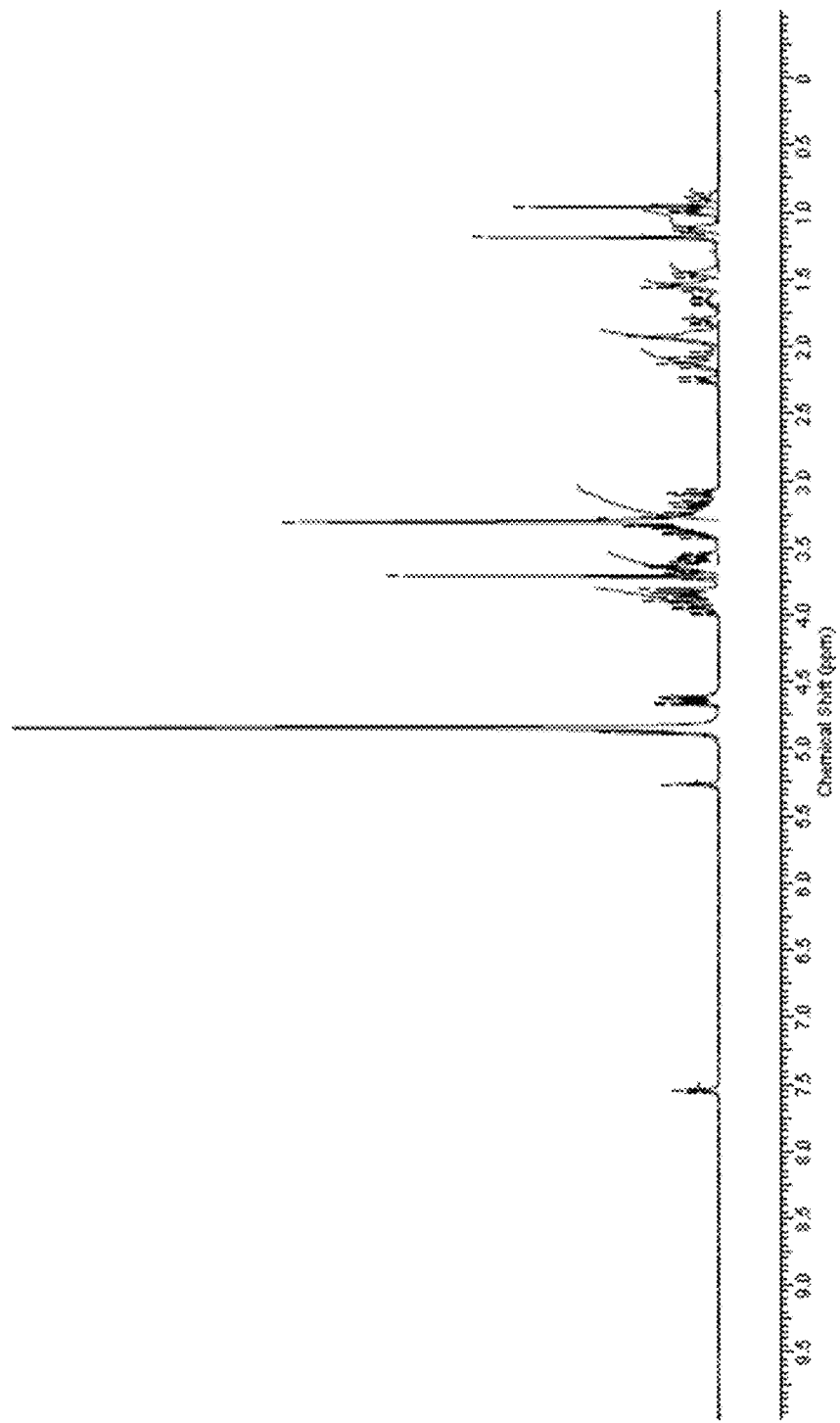
FIGS. 5A-5D are $^1$H NMR spectra of compounds 5A1-5D1, respectively.
Figure 5B:
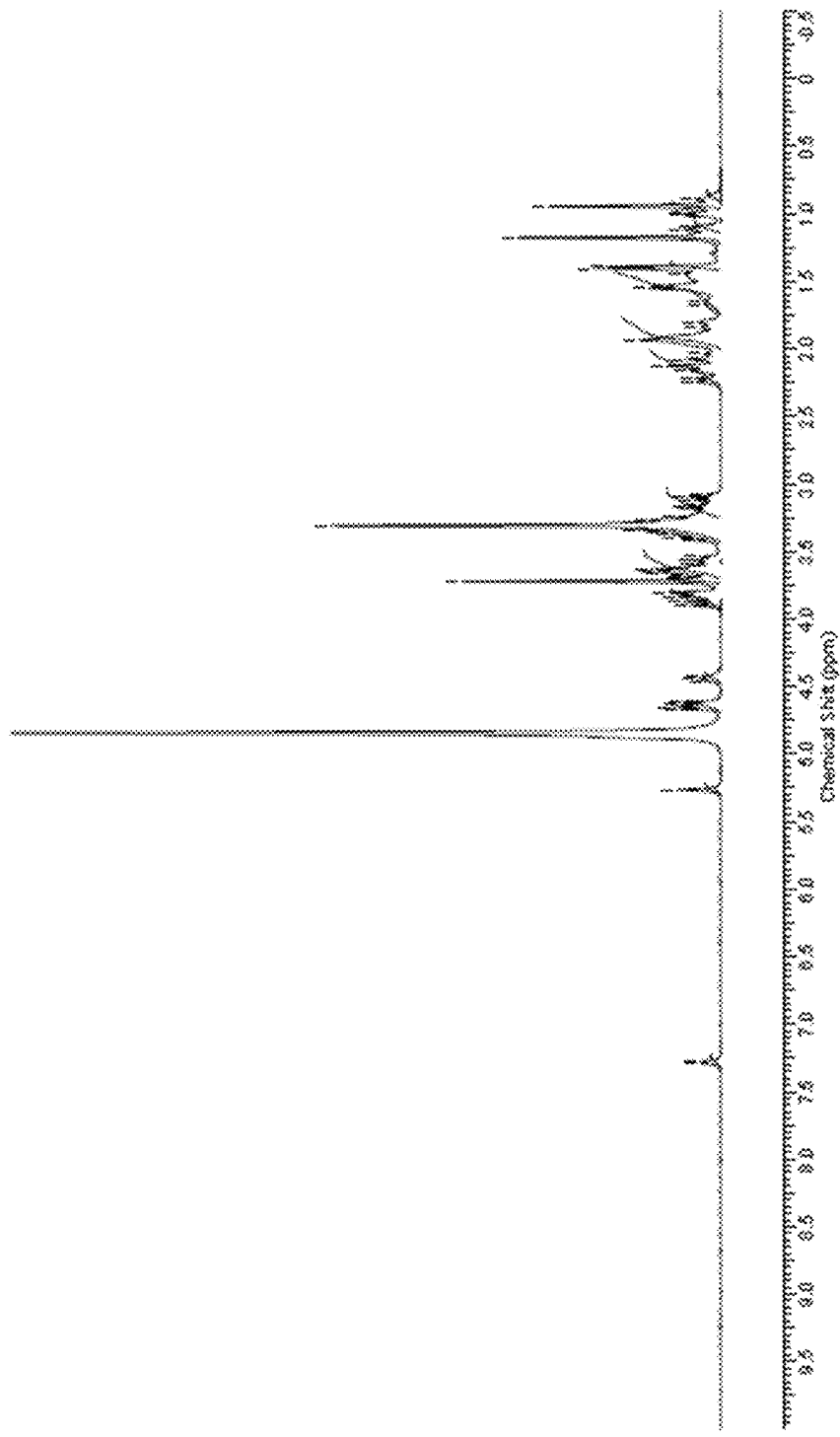
Figure 5C:
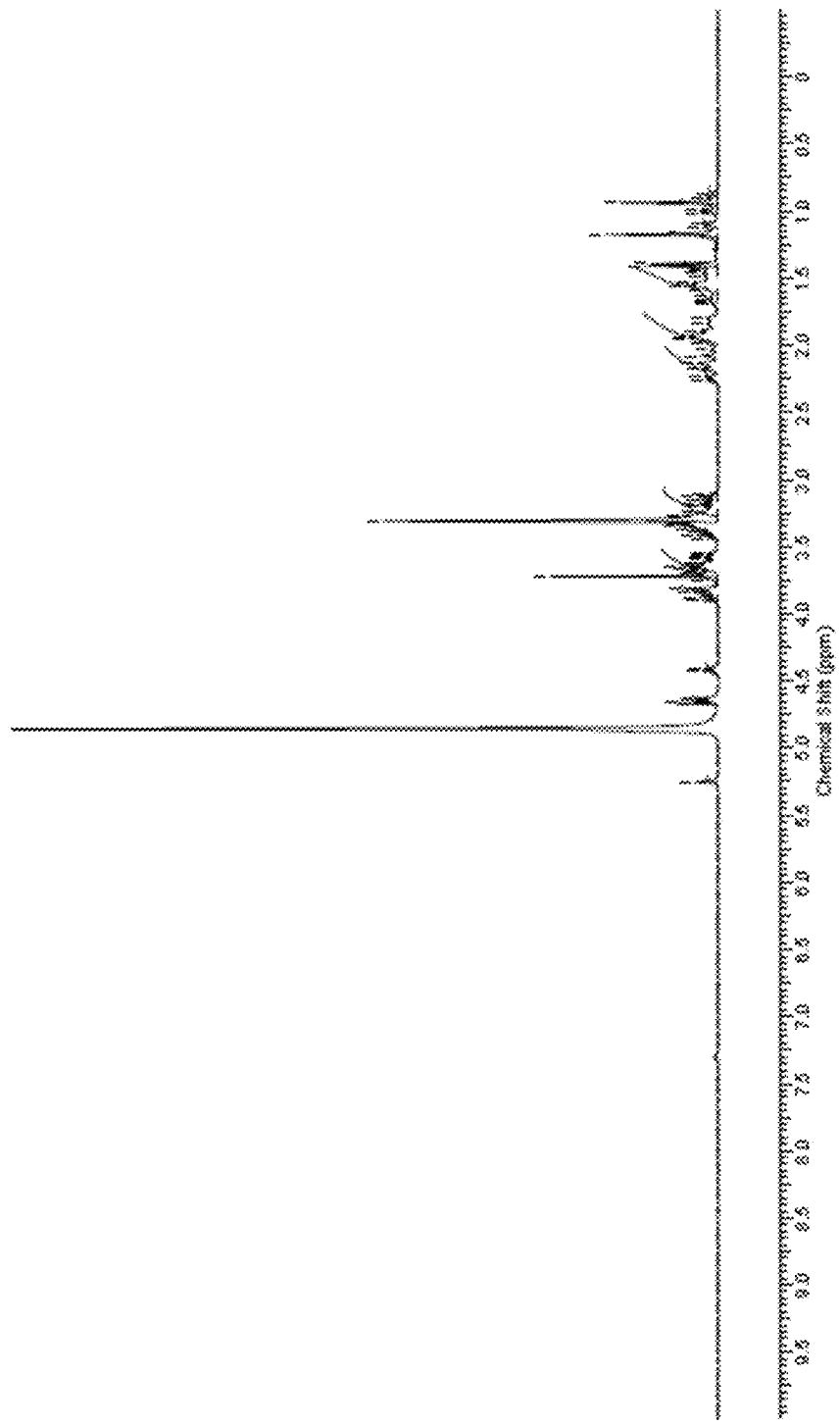
Figure 5D:
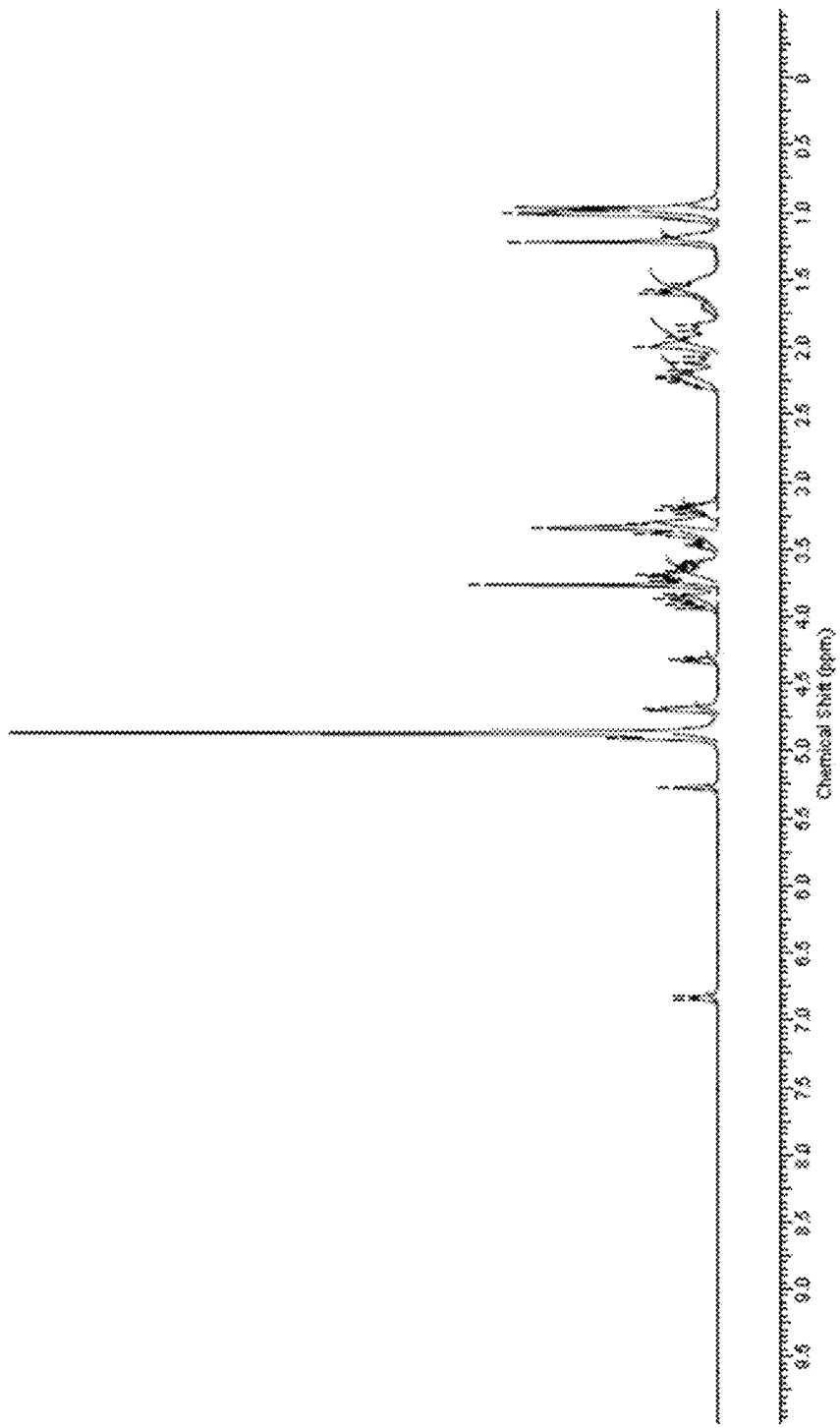
Figure 6A:
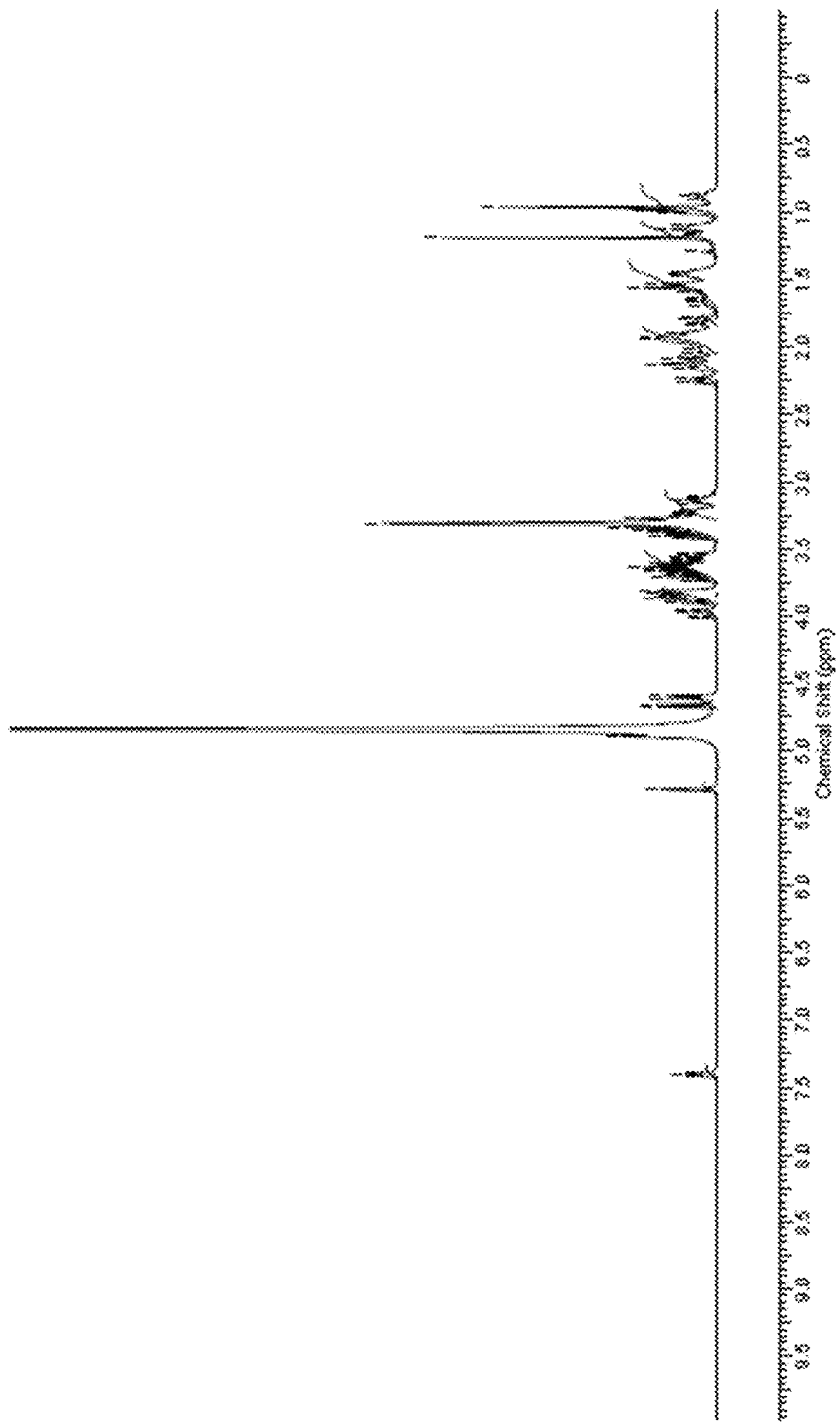
FIGS. 6A-6E are $^1$H NMR spectra of compounds 5A2-5E2, respectively.
Figure 6B:
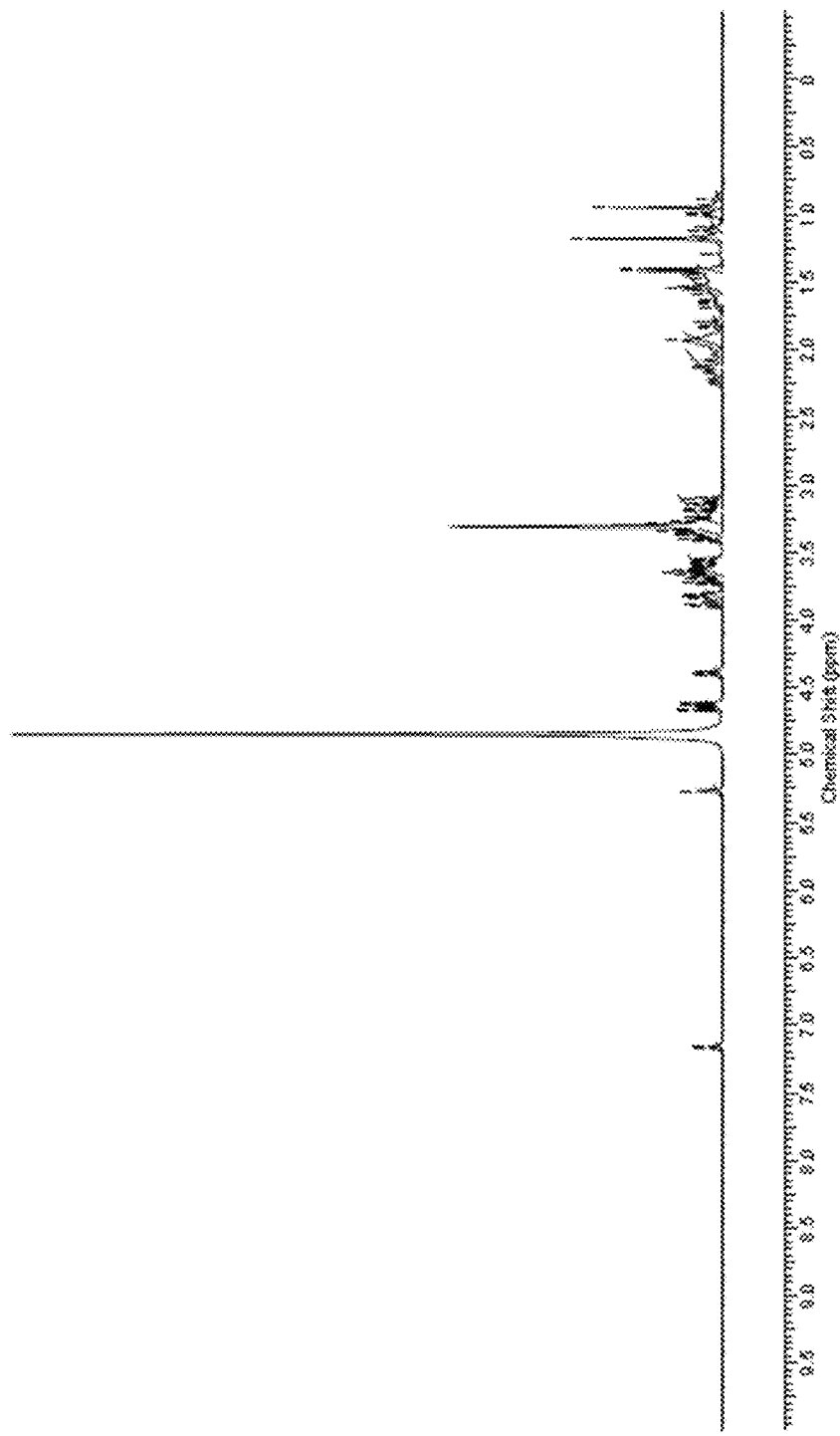
Figure 6C:
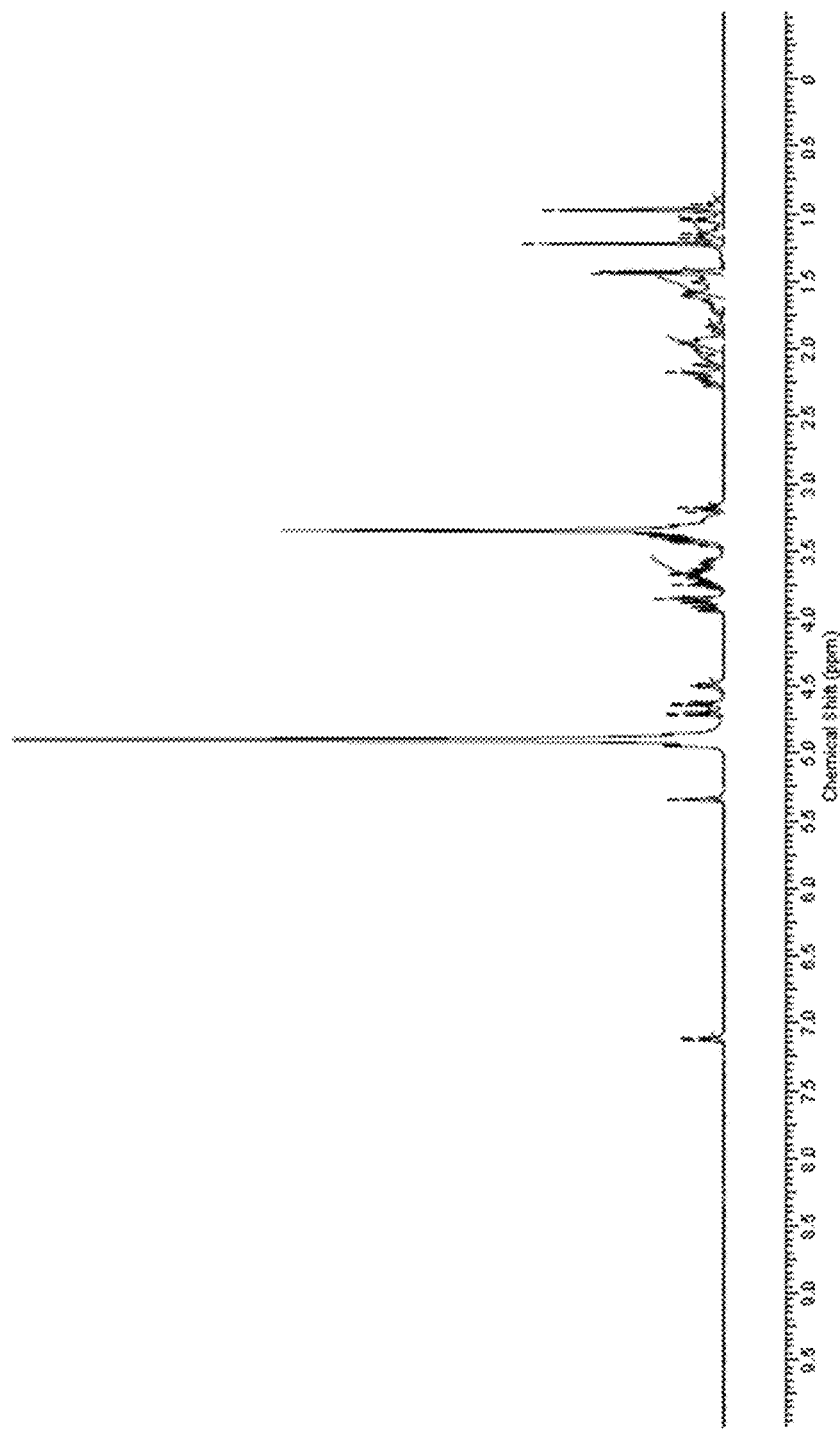
Figure 6D:
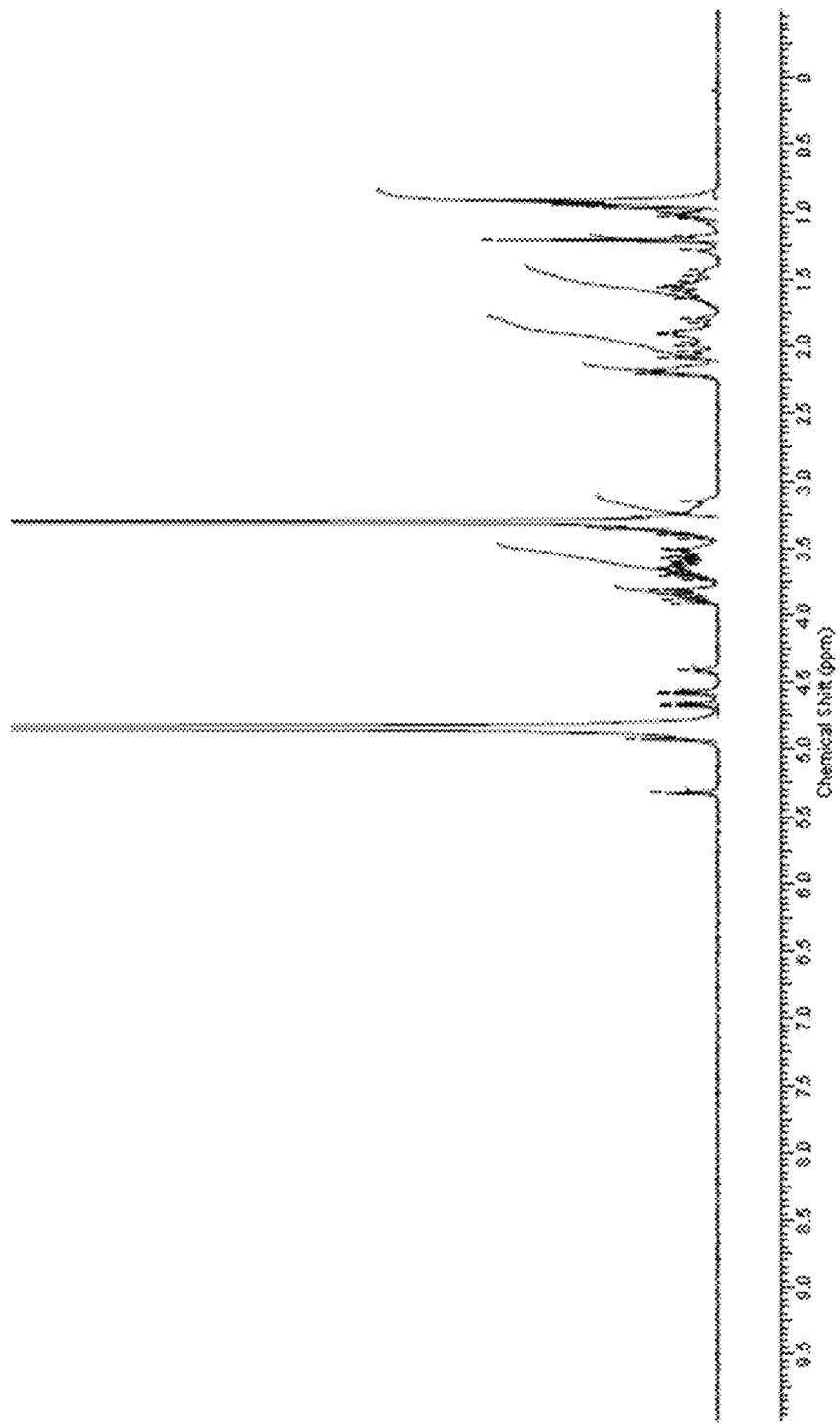
Figure 6E:
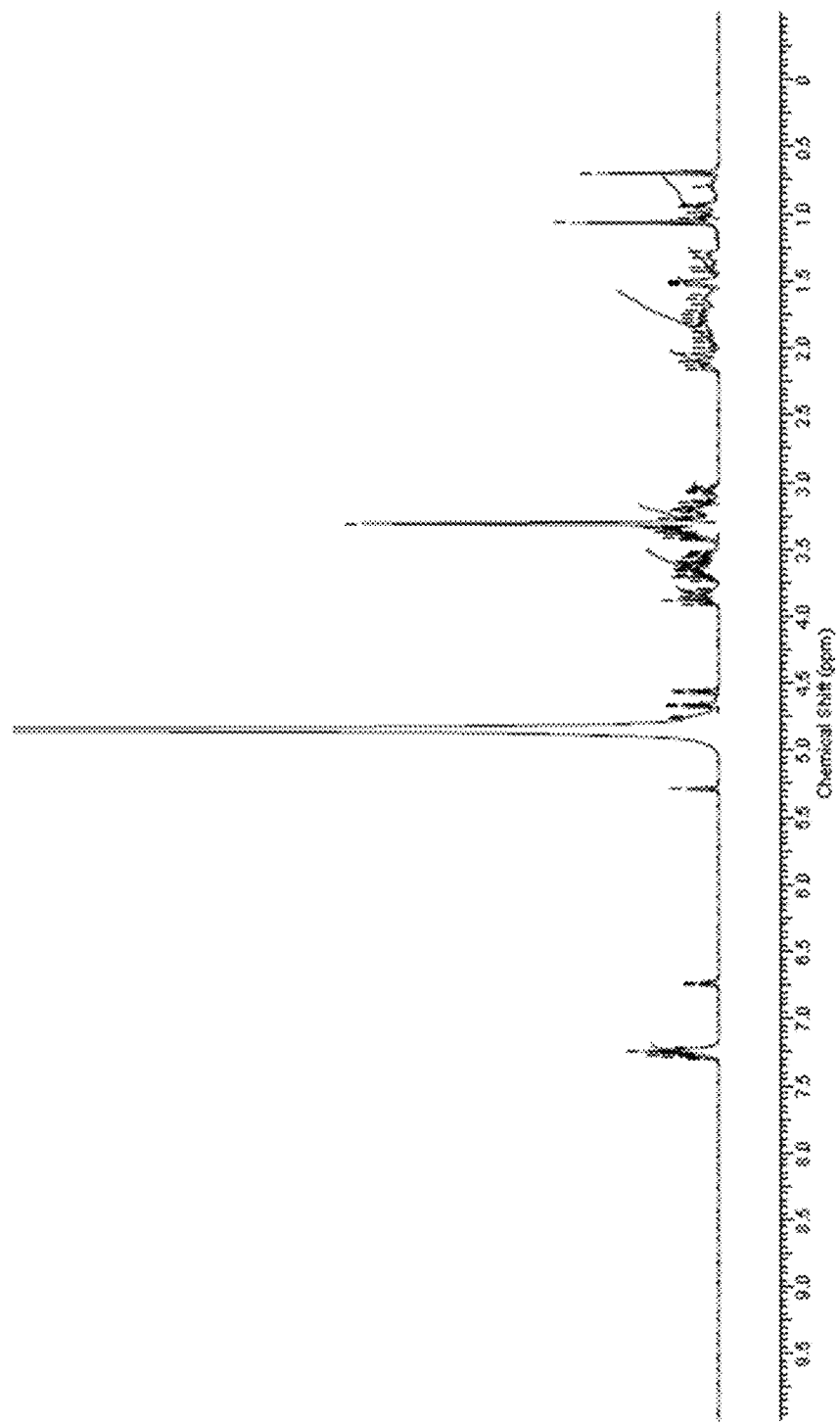
Figure 7A:
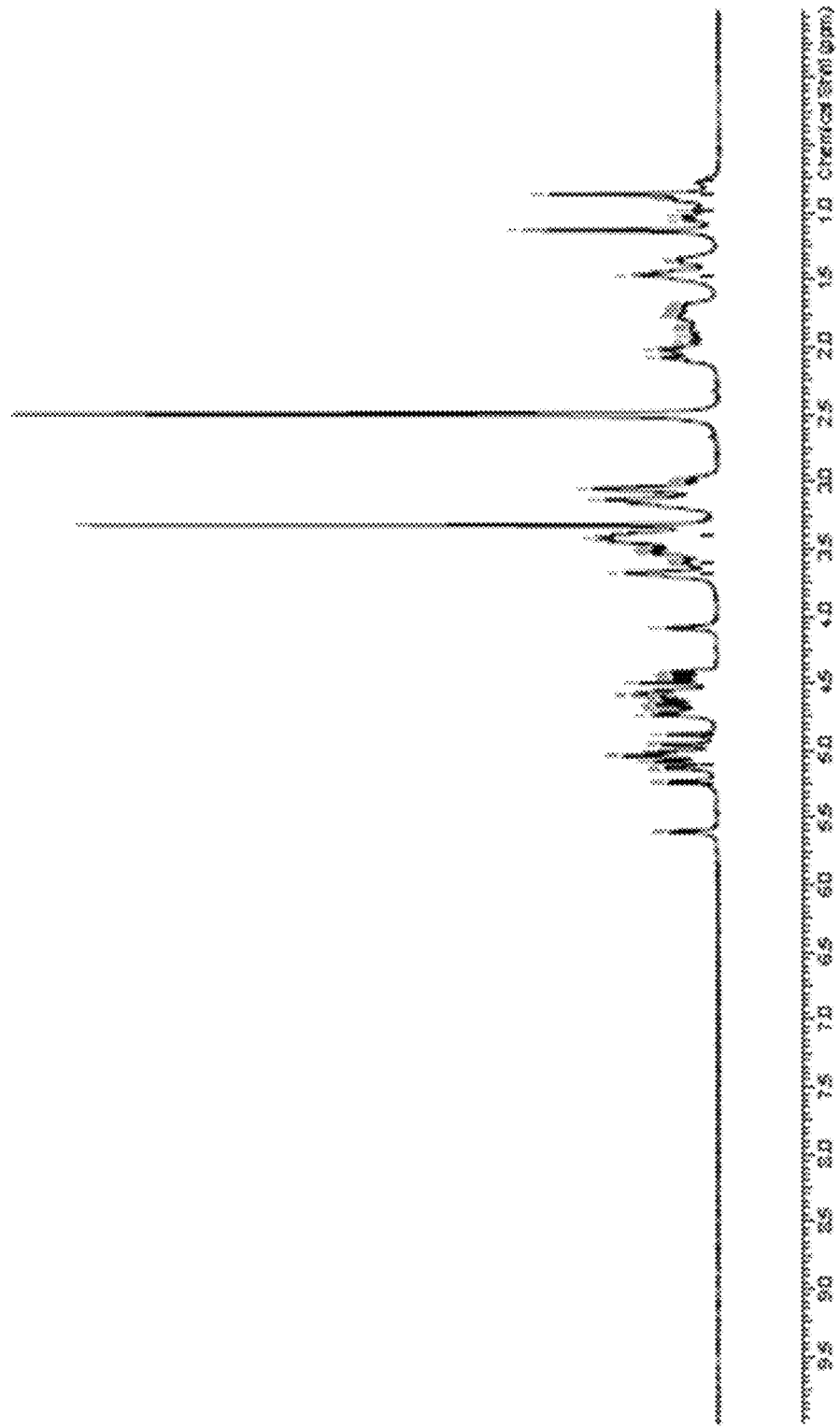
FIGS. 7A-7D are $^1$H NMR spectra of compounds 7A-7D, respectively.
Figure 7B:
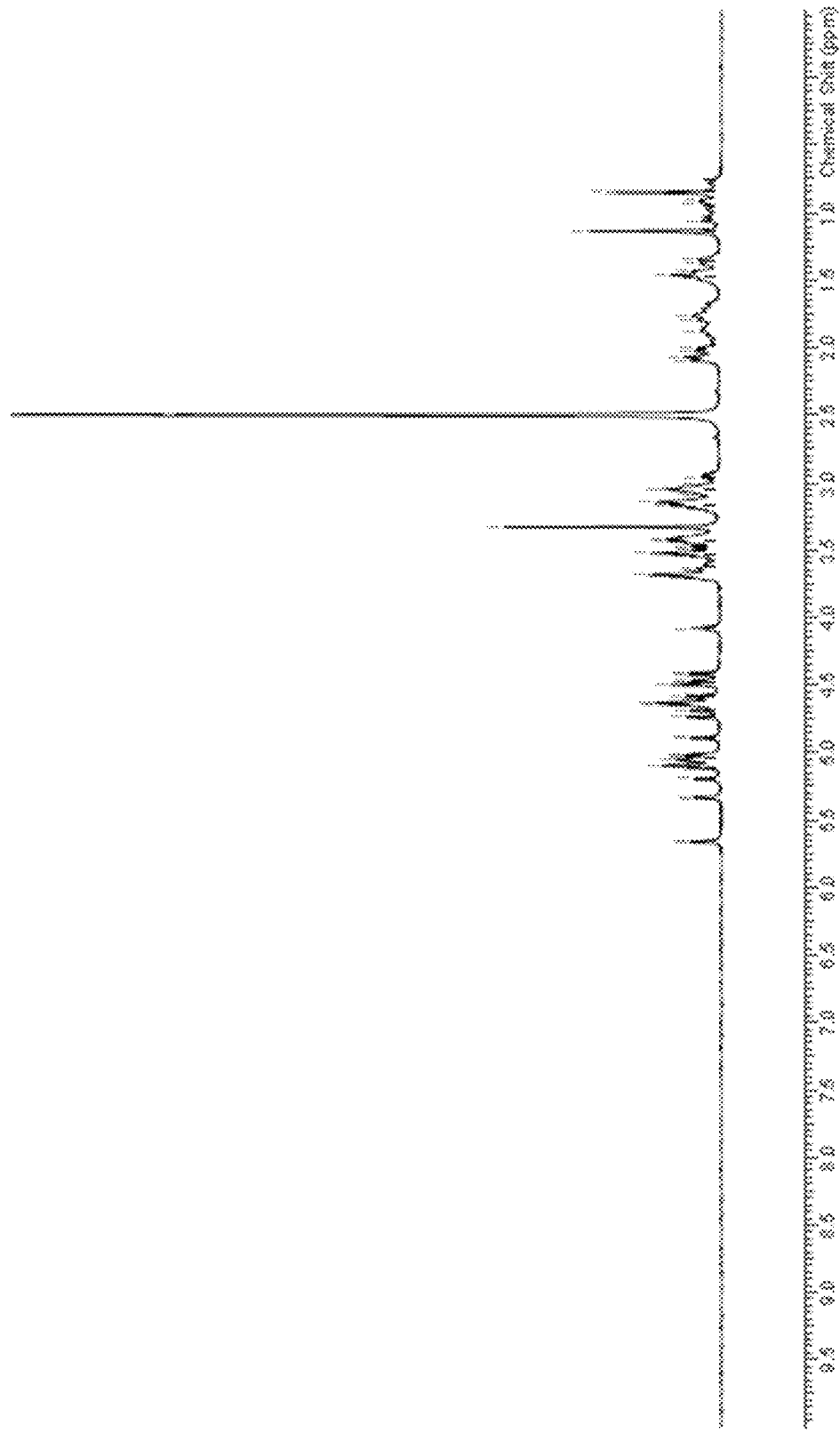
Figure 7C:
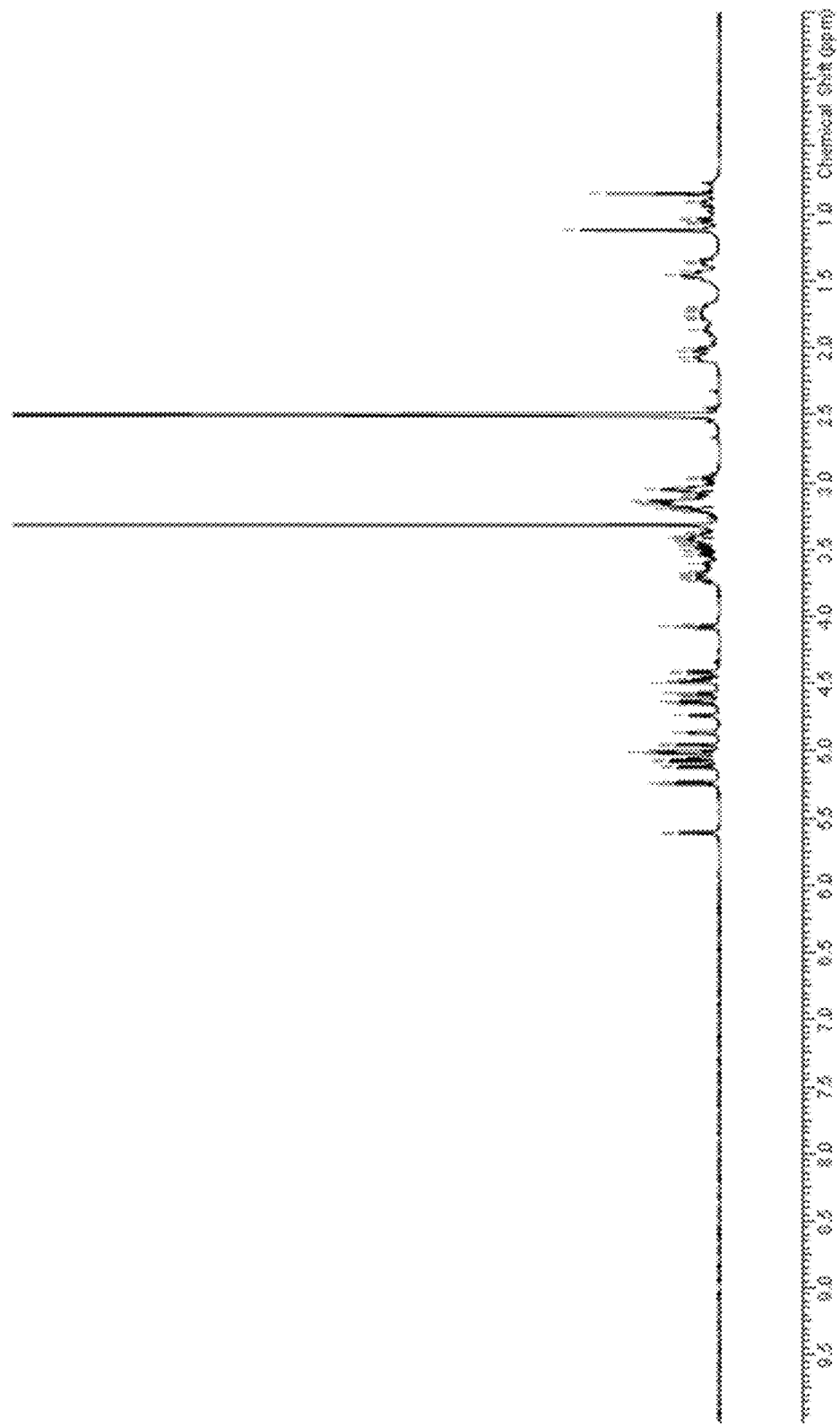
Figure 7D:
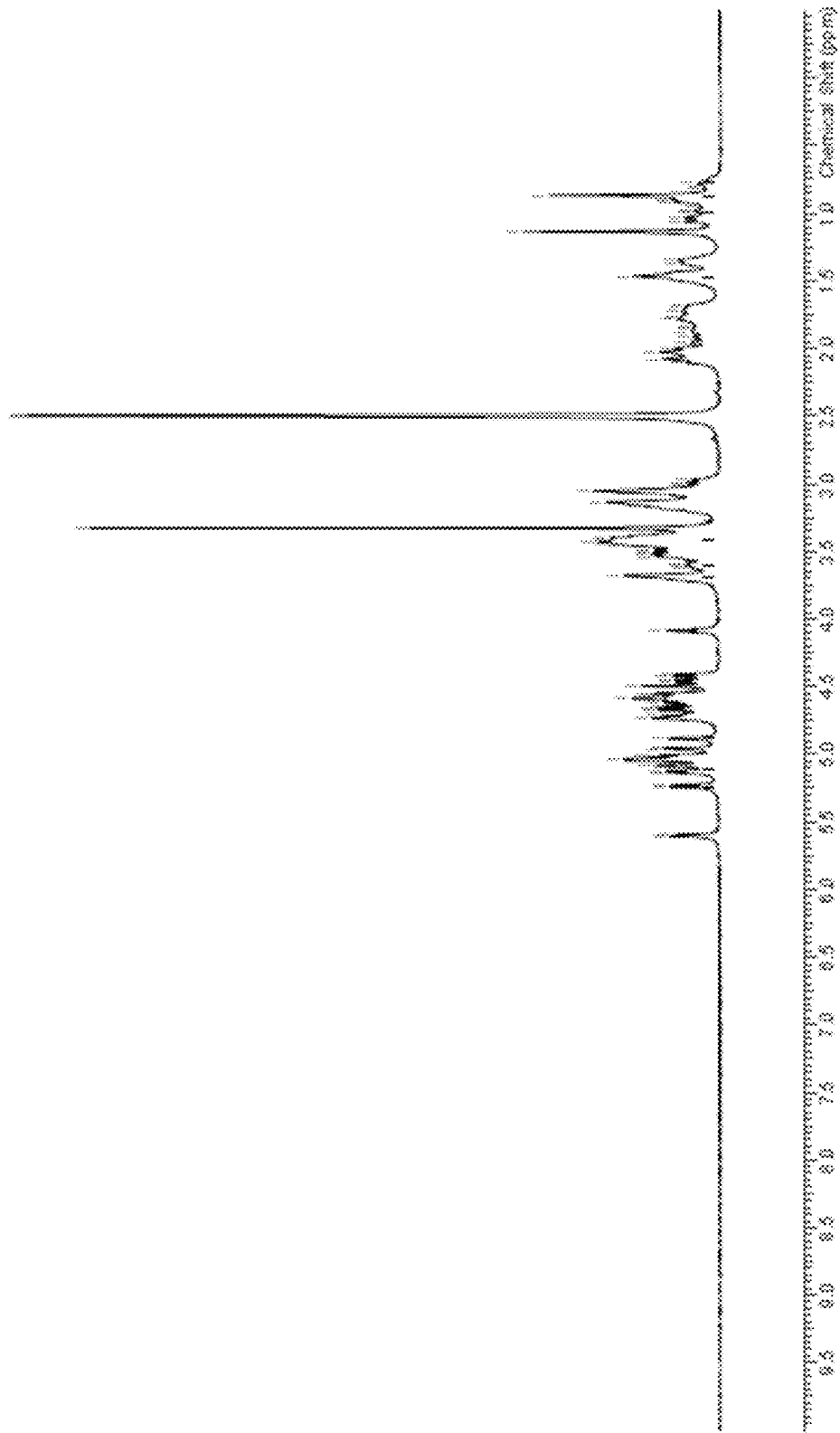

Enhancement:

Panelists were asked to rank 4 samples from least sweet to most sweet, with 1=least sweet and 4=most sweet As shown in FIGS. 1-3, Enhancement of Reb A, high-fructose corn syrup and sucrose were observed.

Alternative Embodiments

The present disclosure also provides the following, non-limiting, set of alternative embodiments.

Embodiment 1

A compound of Formula I:

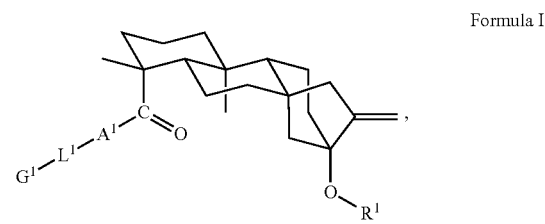

Formula I wherein:

R$^1$ is hydrogen, 1-β-D-glucopyranosyl, 2-(1-β-D-glucopyranosyl)-1-β-D-glucopyranosyl, 2,3-bis(1-β-D-glucopyranosyl)-1-β-D-glucopyranosyl, 2-(1-α-L-rhamnopyranosyl)-1-β-D-glucopyranosyl, 2-(1-α-L- rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl;

$A^1$ is $NR^{10}$ or O;

$L^1$ is a bond linking $A^1$ and $G^1$, a $C_{1-6}$ alkylene linker, a tetrahydropyran ring, or forms a 5- to 7-membered heterocyclic ring with $A^1$ when $A^1$ is $NR^{10}$, $G^1$ is OH, $CH_2OH$, COOH, $R^{11}$, $OR^{12}$, $CONR^{13}R^{14}$, $COOR^{15}$, a tetrahydropyran ring, or

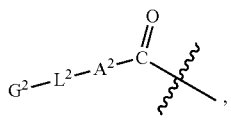

wherein $A^2$ is $NR^{20}$ or O;

$L^2$ is a bond linking $A^2$ and $G^2$, a $C_{1-6}$ alkylene linker, a tetrahydropyran ring, or forms a 5- to 7-membered heterocyclic ring with $A^2$ when $A^2$ is $NR^{20}$;

and $G^2$ is OH, $CH_2OH$, COOH, $R^{21}$, $OR^{22}$, $CONR^{23}R^{24}$ or $COOR^{25}$, wherein the $C_{1-6}$ alkylene linker at each occurrence is independently optionally substituted with one or more substituents independently selected from the group consisting of OH and alkyl, wherein the alkyl is optionally substituted with one or more groups each independently selected from the group consisting of optionally substituted aryl, optionally substituted heteroaryl, COOH, $CONH_2$, $NH_2$, $NHN(=N)NH_2$, SH, SMe, OMe, OH, and $Me_3N^+$;

each of the tetrahydropyran ring at each occurrence is independently optionally substituted with one or more groups each independently selected from the group consisting of OH, Cl, $CH_2Cl$, $CH_2OH$, COOH, alkyl, and $OR^{30}$, wherein $R^{30}$ is a pyranosyl or a tetrahydrofuran ring;

each of the tetrahydrofuran ring at each occurrence is independently optionally substituted with one or more groups each independently selected from the group consisting of OH, Cl, $CH_2Cl$, $CH_2OH$, COOH, and alkyl; and each of $R^{10}$, $R^{11}$, $R^{12}$, $R^{13}$, $R^{14}$, $R^{20}$, $R^{21}$, $R^{22}$, $R^{23}$, and $R^{24}$ is independently selected from the group consisting of H, alkyl, cycloalkyl, and heterocycle, wherein each of the alkyl, cycloalkyl, and heterocycle is optionally substituted with one or more groups each independently selected from the group consisting of alkyl, optionally substituted aryl, optionally substituted heteroaryl, COOH, $CONH_2$, $NH_2$, $NHN(=N)NH_2$, SH, SMe, OMe, OH, and $Me_3N^+$; and $R^{15}$ and $R^{25}$ are each independently a $C_{1-6}$ alkyl.

or a salt thereof, provided that the compound of Formula I is not rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, or rebaudioside O.

Embodiment 2

The compound of embodiment 1, having a Formula S:

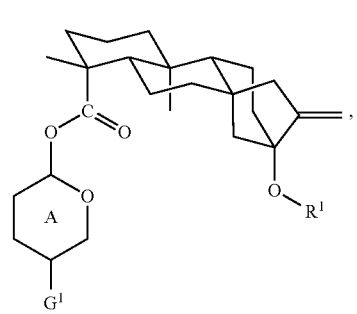

Formula S wherein: $R^1$ is 2,3-bis(1-β-D-glucopyranosyl)-1-β-D-glucopyranosyl, $G^1$ is OH, and ring A is optionally further substituted with up to four $R^{100}$, each independently selected from the group consisting of OH, $CH_2OH$, Cl, COOH, $CH_2Cl$, Me, and $OR^{30}$, wherein $R^{30}$ is a pyranosyl or a tetrahydrofuran ring.

Embodiment 3

The compound of embodiment 2, selected from the group consisting of

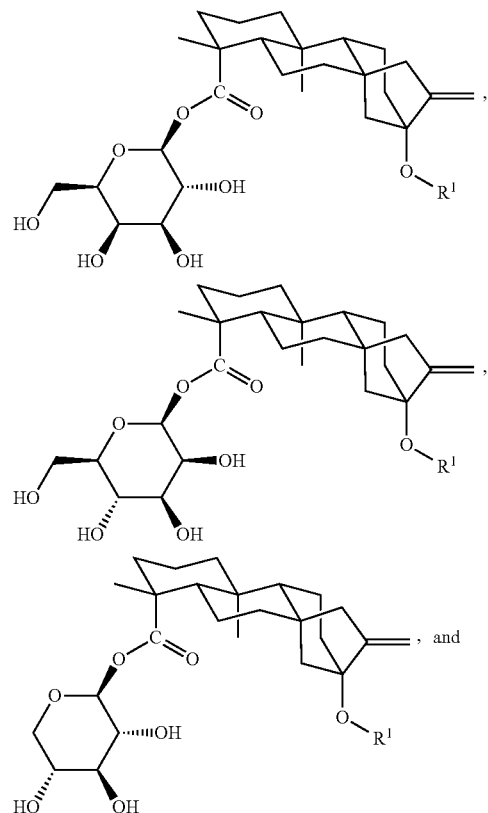

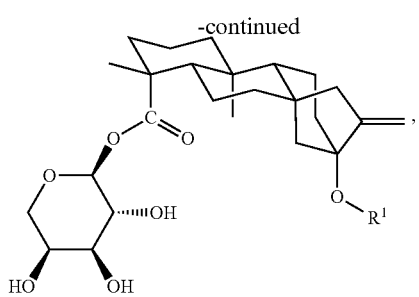

wherein R¹ is 2,3-bis(1-β-D-glucopyranosyl)-1-β-D-glucopyranosyl.

Embodiment 4

The compound of claim 1, wherein R¹ is 2-(1-α-L-rhamnopyranosyl)-3-(1-β-D-glucopyranosyl)-1-β-D-glucopyranosyl Embodiment 5

The compound of claim 1, wherein R¹ is 2-(1-β-D-xylopyranosyl)-3-(1-β-D-glucopyranosyl)-1-β-D-glucopyranosyl.

Embodiment 6

The compound of embodiment 1, having a structure of

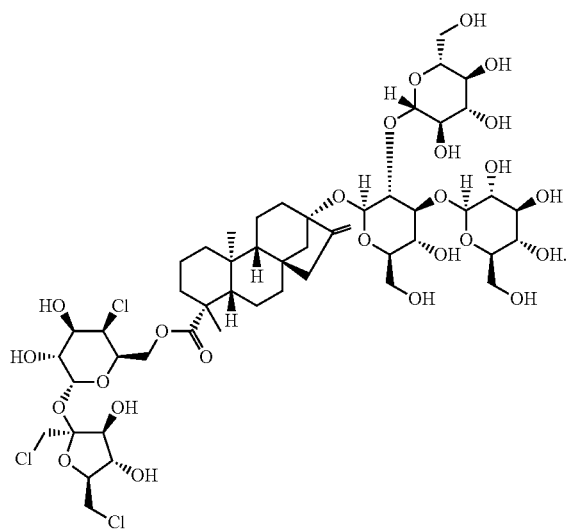

Embodiment 7

The compound of embodiment 1, wherein
A¹ is O,
L¹ is a $C_{1-6}$ alkylene linker, and
G¹ is OH, $CH_2OH$, COOH, or $COOR^{15}$, wherein $R^{15}$ is a $C_{1-4}$ alkyl; and
wherein the $C_{1-6}$ alkylene linker is optionally substituted with 1-5 OH.

Embodiment 8

The compound of embodiment 7, wherein
L¹ is $CH_2CH_2$, and G¹ is OH.

Embodiment 9

The compound of embodiment 7, wherein
L¹ is CHMe, and
G¹ is COOH or $COOR^{15}$, wherein $R^{15}$ is a $C_{1-4}$ alkyl.

Embodiment 10

The compound of embodiment 7, wherein
$A^1$-$L^1$-$G^1$ represents a sugar alcohol residue selected from the group consisting of glycerol, erythritol, threitol, arabitol, xylitol, ribitol, mannitol, sorbitol, galactitol, fucitol, and iditol.

Embodiment 11

The compound of embodiment 10, wherein $A^1$-$L^1$-$G^1$ represents a sugar alcohol residue selected from the group consisting of glycerol, erythritol, xylitol, sorbitol, and mannitol, wherein the sugar alcohol residue is in a D-configuration.

Embodiment 12

The compound of any one of embodiments 7-11, wherein R¹ is 2,3-bis(1-β-D-glucopyranosyl)-1-β-D-glucopyranosyl.

Embodiment 13

The compound of any one of embodiments 7-11, wherein R¹ is 2-(1-α-L-rhamnopyranosyl)-3-(1-β-D-glucopyranosyl)-1-β-D-glucopyranosyl.

Embodiment 14

The compound of any one of embodiments 7-11, wherein R¹ is 2-(1-β-D-xylopyranosyl)-3-(1-β-D-glucopyranosyl)-1-β-D-glucopyranosyl.

Embodiment 15

The compound of embodiment 1, wherein
A¹ is O,
L¹ is a bond linking A¹ and G¹; and
G¹ is $R^{11}$,
wherein $R^{11}$ is a H or $C_{1-4}$ alkyl.

Embodiment 16

The compound of embodiment 15, wherein R¹ is 2,3-bis(1-β-D-glucopyranosyl)-1-β-D-glucopyranosyl and $R^{11}$ is a $C_{1-4}$ alkyl.

Embodiment 17

The compound of embodiment 1, wherein
A¹ is $N^{10}$, wherein $R^{10}$ is H,
L¹ is $CRH^{101}$, and
G¹ is COOH or $COOR^{15}$,
wherein $R^{101}$ is H or a $C_{1-4}$ alkyl which is optionally substituted with one or more groups each independently selected from the group consisting of phenyl, 4-hydroxyphenyl, imidazolyl, COOH, CONH$_2$, NH$_2$, NHN(=N)NH$_2$, SH, SMe, OMe, OH, and Me$_3$N$^+$.

Embodiment 18

The compound of embodiment 17, wherein L$^1$ is CH$_2$.

Embodiment 19

The compound of embodiment 17, wherein R$^{101}$ is a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine.

Embodiment 20

The compound of any one of embodiments 17-19, wherein R$^{101}$ is H or a side chain of an amino acid selected from the group consisting of alanine, phenylalanine, and valine.

Embodiment 21

The compound of any one of embodiments 17-20, wherein G$^1$ is COOH.

Embodiment 22

The compound of any one of embodiments 17-21, wherein G$^1$ is COOR$^{15}$, wherein R$^{15}$ is a C$_{1-4}$ alkyl.

Embodiment 23

The compound of any one of embodiments 17-22, wherein R$^1$ is 2,3-bis(1-β-D-glucopyranosyl)-1-β-D-glucopyranosyl.

Embodiment 24

The compound of any one of embodiments 17-22, wherein R$^1$ is 2-(1-α-L-rhamnopyranosyl)-3-(1-β-D-glucopyranosyl)-1-β-D-glucopyranosyl or 2-(1-β-D-xylopyranosyl)-3-(1-β-D-glucopyranosyl)-1-β-D-glucopyranosyl.

Embodiment 25

The compound of embodiment 1, wherein A$^1$-L$^1$-G$^1$ is

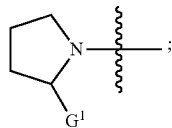

and
G$^1$ is COOH or COOR$^{15}$.

Embodiment 26

The compound of embodiment 25, wherein G$^1$ is COOH, and R$^1$ is 2,3-bis(1-β-D-glucopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl.

Embodiment 27

The compound of embodiment 1, wherein

A$^1$ is NR$^{10}$;

L$^1$ is CHR$^{101}$, R$^{101}$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine; and G$^1$ is

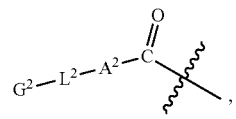

wherein A$^2$ is NR$^{20}$;

L$^2$ is CHR$^{201}$, wherein R$^{201}$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine; and G$^2$ is COOH, COOR$^{25}$, or CONR$^{23}$R$^{24}$.

Embodiment 28

The compound of embodiment 27, wherein G$^2$ is COOH.

Embodiment 29

The compound of embodiment 27, wherein G$^2$ is COOR$^{25}$, wherein R$^{25}$ is a C$_{1-4}$ alkyl.

Embodiment 30

The compound of embodiment 27, wherein G$^2$ is CONR$^{23}$R$^{24}$, wherein one of R$^{23}$ and R$^{24}$ is H, and the other of R$^{23}$ and R$^{24}$ is a heterocycle, wherein the heterocycle is optionally substituted with one or more groups each independently selected from the group consisting of alkyl, optionally substituted aryl, optionally substituted heteroaryl, COOH, CONH$_2$, NH$_2$, NHN(=N)NH$_2$, SH, SMe, OMe, OH, and Me$_3$N$^+$.

Embodiment 31

The compound of embodiment 30, wherein the heterocycle is a thietane.

Embodiment 32

The compound of any one of embodiments 27-31, wherein $R^{20}$ is H or a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, NHN(=N)$NH_2$, SH, SMe, OMe, OH and $Me_3N^+$.

Embodiment 33

The compound of embodiment 32, wherein $R^{20}$ is H.

Embodiment 34

The compound of any one of embodiments 27-33, wherein $R^{10}$ is H or a $C_{1-4}$ alkyl, which is optionally substituted with one or more groups each independently selected from the group consisting of a $C_{1-4}$ alkyl, phenyl, 3'-hydroxy-4'-methoxyphenyl, COOH, $CONH_2$, $NH_2$, NHN(=N)$NH_2$, SH, SMe, OMe, OH and $Me_3N^+$.

Embodiment 35

The compound of embodiment 34, wherein $R^{10}$ is H.

Embodiment 36

The compound of embodiment 35, wherein $R^{10}$ is a $C_{1-4}$ alkyl optionally substituted with one of a $C_{1-4}$ alkyl, phenyl, and 3'-hydroxy-4'-methoxyphenyl.

Embodiment 37

The compound of any one of embodiments 27-36, wherein $R^1$ is 2,3-bis(1-β-D-glucopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl.

Embodiment 38

The compound of embodiment 1, having a structure of Formula A2:

Formula A2 or a salt thereof.

Embodiment 39

The compound of embodiment 38, wherein $G^1$ is COOH.

Embodiment 40

The compound of embodiment 38, wherein $G^1$ is selected from the group consisting of:

or a salt thereof.

Embodiment 41

The compound of embodiment 27, selected from the group consisting of

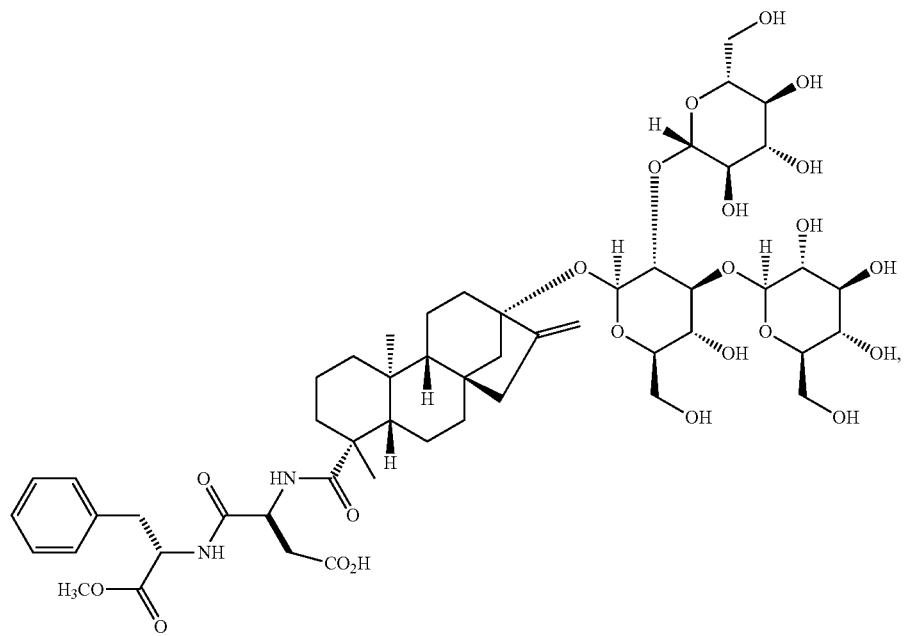
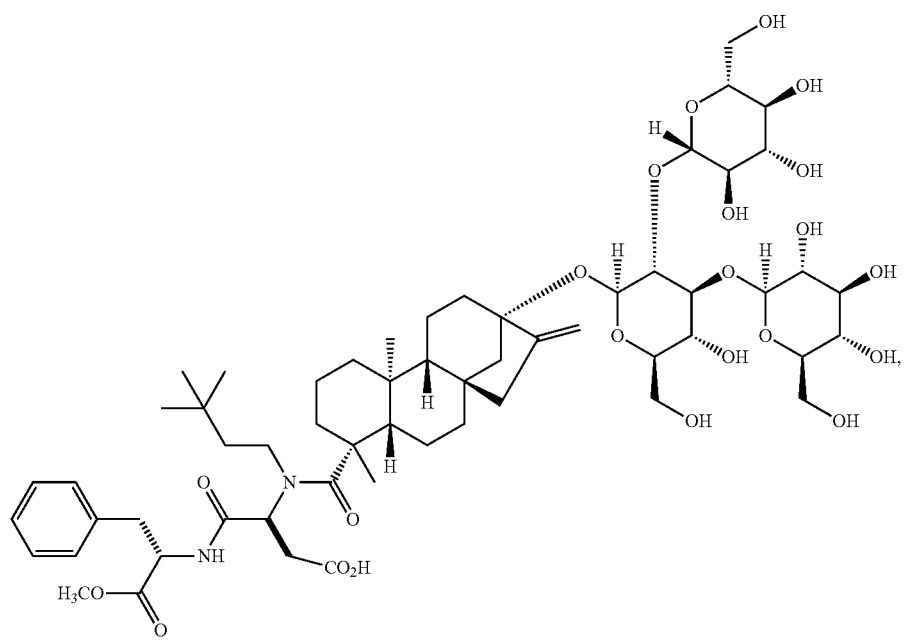

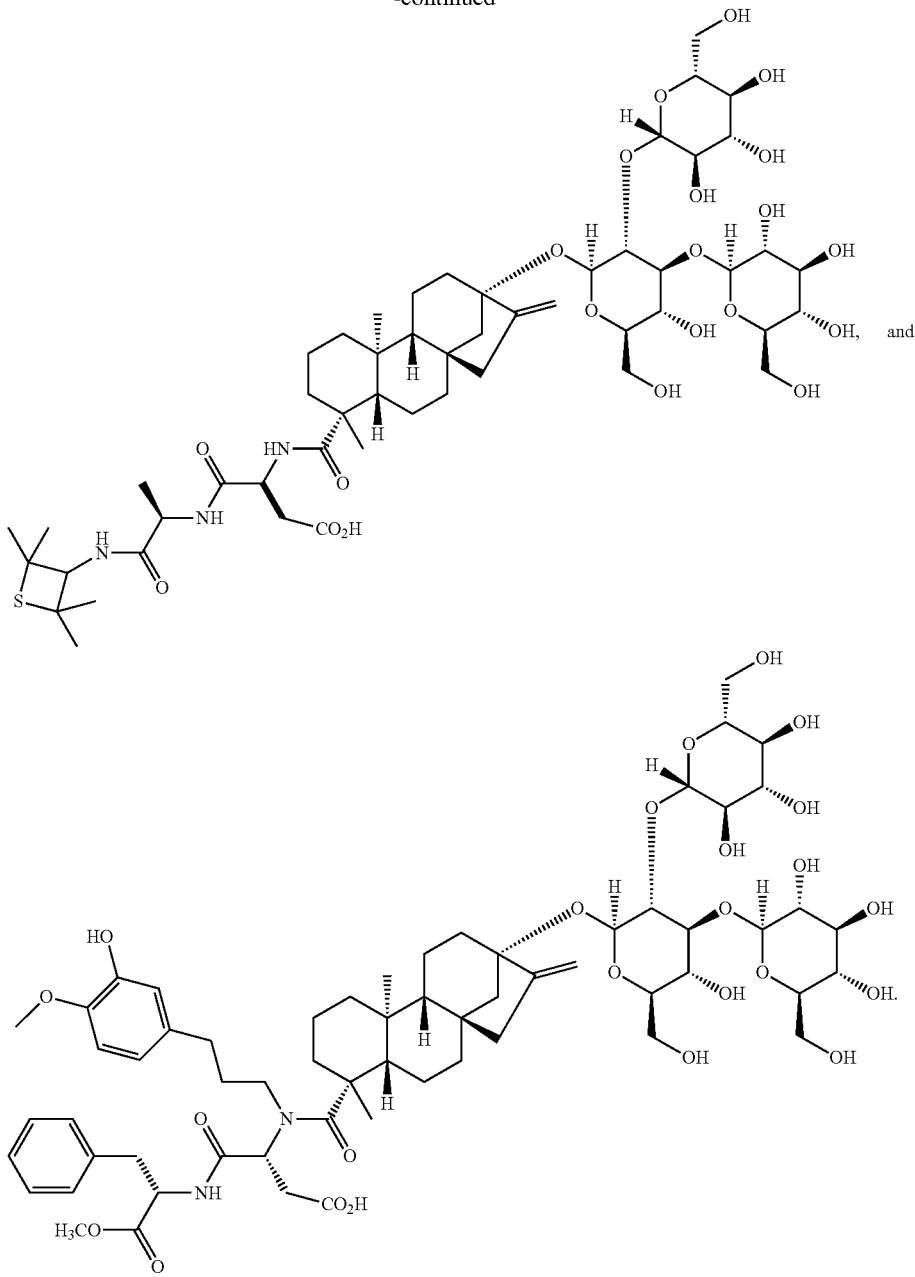

Embodiment 42

A sweetener composition comprising a compound of any one of embodiments 1-41, wherein the compound is present in a concentration above its sweetness recognition threshold concentration.

Embodiment 43

The sweetener composition of embodiment 42, further comprising a second sweetener.

Embodiment 44

The sweetener composition of embodiment 43, wherein the second sweetener is a nutritive sweetener.

Embodiment 45

The sweetener composition of embodiment 43, wherein the second sweetener is a non-nutritive sweetener.

Embodiment 46

The sweetener composition of embodiment 43, wherein the second sweetener is selected from the group consisting of a steviol glycoside, Stevia rebaudiana extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and mixtures of any of them.

Embodiment 47

The sweetener composition of embodiment 46, wherein the second sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

Embodiment 48

The sweetener composition of any one of embodiments 42-47, further comprising at least one sweetness enhancer in a concentration sufficient to further enhance the sweetness of the compound and/or the second sweetener but in a concentration below the sweetness enhancer's sweetness recognition threshold concentration.

Embodiment 49

The sweetener composition of embodiment 48, wherein the at least one sweetness enhancer is D-psicose, erythritol, rubusoside, rebaudioside B, rebaudioside C, trilobatin, phyllodulcin, brazzein, mogrosides, or a combination of any of the foregoing.

Embodiment 50

A sweetener composition comprising a sweetener and a compound of any one of embodiments 1-41, wherein the compound is present in a concentration sufficient to further enhance the sweetness of the sweetener but in a concentration below the compound's sweetness recognition threshold concentration.

Embodiment 51

The sweetener composition of embodiment 50, wherein the sweetener is a nutritive sweetener.

Embodiment 52

The sweetener composition of embodiment 50, wherein the sweetener is a non-nutritive sweetener.

Embodiment 53

The sweetener composition of embodiment 50, wherein the sweetener is selected from the group consisting of a steviol glycoside, Stevia rebaudiana extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and mixtures of any of them.

Embodiment 54

The sweetener composition of embodiment 53, wherein the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

Embodiment 55

The sweetener composition of any one of embodiments 50-54, further comprising at least one supplemental sweetness enhancer in a concentration sufficient to further enhance the sweetness of the sweetener but in a concentration below the supplemental sweetness enhancer's sweetness recognition threshold concentration.

Embodiment 56

The sweetener composition of embodiment 55, wherein the at least one supplemental sweetness enhancer is D-psicose, erythritol, rubusoside, rebaudioside B, rebaudioside C, trilobatin, phyllodulcin, brazzein, mogrosides, or a combination of any of the foregoing.

Embodiment 57

A beverage product comprising a sweetener composition of any one of embodiments 42-56.

Embodiment 58

A beverage product comprising a compound of any one of embodiments 1-41.

Embodiment 59

The beverage product of embodiment 57 or 58, wherein the beverage product is selected from the group consisting of carbonated beverages, non-carbonated beverages, fountain beverages, frozen carbonated beverages, powdered concentrates, beverage concentrates, fruit juices, fruit juice-flavored drinks, fruit-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and mixtures of any of them.

Embodiment 60

A beverage concentrate comprising a compound of any one of embodiments 1-41.

Embodiment 61

A beverage concentrate comprising a sweetener composition of any one of embodiments 42-56.

Embodiment 62

A food product comprising a food component and a compound of any one of embodiments 1-41.

Embodiment 63

A food product comprising a food component and a sweetener composition of any one of embodiments 42-56.

Embodiment 64

The food product of embodiment 62 or 63, wherein the food product is selected from the group consisting of oatmeal, cereal, baked goods, cookies, crackers, cakes, brownies, breads, snack foods, potato chips, tortilla chips, popcorn, snack bars, rice cakes, and grain-based food products.

Embodiment 65

A method of reducing the amount of sweetener in a food product or a beverage product, comprising replacing at least a portion of the sweetener in the food or beverage product with a compound of any one of embodiments 1-41.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed:

1. A compound of Formula I:

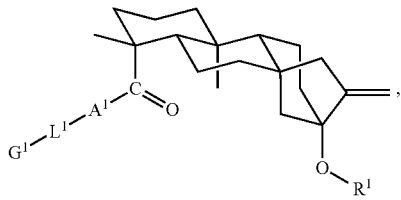

Formula I wherein:

$R^1$ is 2,3-bis(1-β-D-glucopyranosyl)-1-β-D-glucopyranosyl, 2-(1-α-L-rhamnopyranosyl)-3-(1-β-D-glucopyranosyl)-1-β-D-glucopyranosyl, or 2-(1-β-D-xylopyranosyl)-3-(1-β-D-glucopyranosyl)-1-β-D-glucopyranosyl, $A^1$ is $NR^{10}$ or O;

$L^1$ is a bond linking $A^1$ and $G^1$, a $C_{1-6}$ alkylene linker, a tetrahydropyran ring, or forms a 5- to 7-membered heterocyclic ring with $A^1$ when $A^1$ is $NR^{10}$, $G^1$ is OH, $CH_2OH$, $R^{11}$, $OR^{12}$, $CONR^{13}R^{14}$, $COOR^{15}$, or

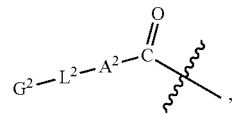

wherein $A^2$ is $NR^{20}$ or O;

$L^2$ is a bond linking $A^2$ and $G^2$, a $C_{1-6}$ alkylene linker, a tetrahydropyran ring, or forms a 5- to 7-membered heterocyclic ring with $A^2$ when $A^2$ is $NR^{20}$;

and $G^2$ is OH, $CH_2OH$, COOH, $R^{21}$, $OR^{22}$, $CONR^{23}R^{24}$ or $COOR^{25}$, wherein the $C_{1-6}$ alkylene linker at each occurrence is independently optionally substituted with one or more alkyl, wherein the alkyl is optionally substituted with one or more groups each independently selected from the group consisting of optionally substituted aryl, optionally substituted heteroaryl, COOH, $CONH_2$, $NH_2$, NHC(=N)$NH_2$, SH, SMe, OMe, OH, and $Me_3N^+$;

each tetrahydropyran ring at each occurrence is independently optionally substituted with one or more groups each independently selected from the group consisting of OH, Cl, $CH_2Cl$, $CH_2OH$, COOH, alkyl, and $OR^{30}$, wherein $R^{30}$ is a tetrahydrofuran ring;

each tetrahydrofuran ring at each occurrence is independently optionally substituted with one or more groups each independently selected from the group consisting of OH, Cl, $CH_2Cl$, $CH_2OH$, COOH, and alkyl; and each of $R^{10}$, $R^{12}$, $R^{13}$, $R^{14}$, $R^{20}$, $R^{21}$, $R^{22}$, $R^{23}$, and $R^{24}$ is independently selected from the group consisting of H, alkyl, cycloalkyl, and heterocycle, wherein each of the alkyl, cycloalkyl, and heterocycle is optionally substituted with one or more groups each independently selected from the group consisting of alkyl, optionally substituted aryl, optionally substituted heteroaryl, COOH, $CONH_2$, $NH_2$, NHC(=N)$NH_2$, SH, SMe, OMe, OH, and $Me_3N^+$; and $R^{11}$ is cycloalkyl or heterocycle, wherein the cycloalkyl and heterocycle are optionally substituted with one or more groups each independently selected from the group consisting of alkyl, optionally substituted aryl, optionally substituted heteroaryl, $CONH_2$, NHC(=N)$NH_2$, SH, SMe, OMe, and $Me_3N^+$; and $R^{15}$ and $R^{25}$ are each independently a $C_{1-6}$ alkyl;

or a salt thereof, provided that the compound of Formula I is not rebaudioside A, rebaudioside B, rebaudioside C, rebaudioside D, rebaudioside F, rebaudioside I, rebaudioside J, rebaudioside K, rebaudioside M, rebaudioside N, or rebaudioside O.

2. The compound of claim 1, having a Formula S:

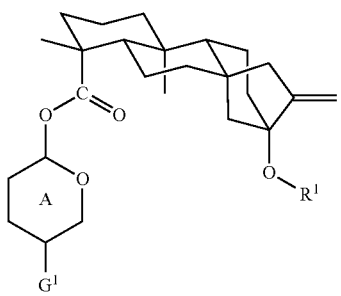

Formula S wherein: $G^1$ is OH, and ring A is optionally further substituted with up to four $R^{100}$, wherein each $R^{100}$ is independently selected from the group consisting of OH, $CH_2OH$, Cl, COOH, $CH_2Cl$, Me, and $OR^{30}$, wherein $R^{30}$ is tetrahydrofuran ring.

3. The compound of claim 2, selected from the group consisting of

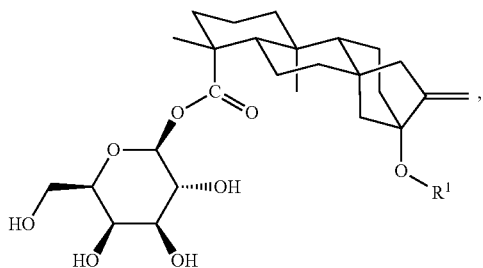

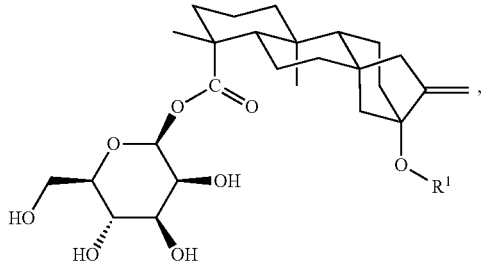

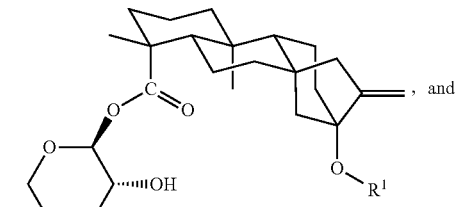
, and

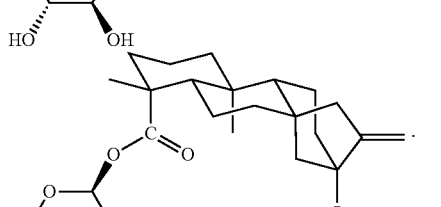
.

4. The compound of claim 1, wherein $R^1$ is 2,3-bis(1-β-D-glucopyranosyl)-1-β-D-glucopyranosyl.

5. The compound of claim 1, wherein
$A^1$ is O,
$L^1$ is a $C_{1-6}$ alkylene linker, and
$G^1$ is OH, $CH_2OH$, or $COOR^{15}$, wherein $R^{15}$ is a $C_{1-4}$ alkyl.

6. The compound of claim 5, wherein
$L^1$ is $CH_2CH_2$, and $G^1$ is OH.

7. The compound of claim 5, wherein
$L^1$ is CHMe, and
$G^1$ is $COOR^{15}$, wherein $R^{15}$ is a $C_{1-4}$ alkyl.

8. The compound of claim 5, wherein $A^1$-$L^1$-$G^1$ represents a sugar alcohol residue selected from the group consisting of glycerol, erythritol, xylitol, sorbitol, and mannitol, wherein the sugar alcohol residue is in a D-configuration.

9. The compound of claim 1, wherein
$A^1$ is $NR^{10}$, wherein $R^{10}$ is H,
$L^1$ is $CHR^{101}$, and
$G^1$ is $COOR^{15}$,
wherein $R^{101}$ is H or a $C_{1-4}$ alkyl which is optionally substituted with one or more groups each independently selected from the group consisting of phenyl, 4-hydroxyphenyl, imidazolyl, COOH, $CONH_2$, $NH_2$, $NHC(=N)NH_2$, SH, SMe, OMe, OH, and $Me_3N^+$.

10. The compound of claim 9, wherein $L^1$ is $CH_2$.

11. The compound of claim 9, wherein $R^{101}$ is H or a side chain of an amino acid selected from the group consisting of alanine, phenylalanine, and valine.

12. The compound of claim 1, wherein
$A^1$ is $NR^{10}$;
$L^1$ is $CHR^{101}$, $R^{101}$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine; and
$G^1$ is

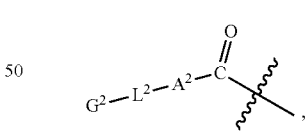
, wherein $A^2$ is $NR^{20}$;
$L^2$ is $CHR^{201}$, wherein $R^{201}$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, serine, threonine, tryptophan, tyrosine, and valine; and
$G^2$ is COOH, $COOR^{25}$, or $CONR^{23}R^{24}$.

13. The compound of claim 1, having a structure of Formula A2:

Formula A2
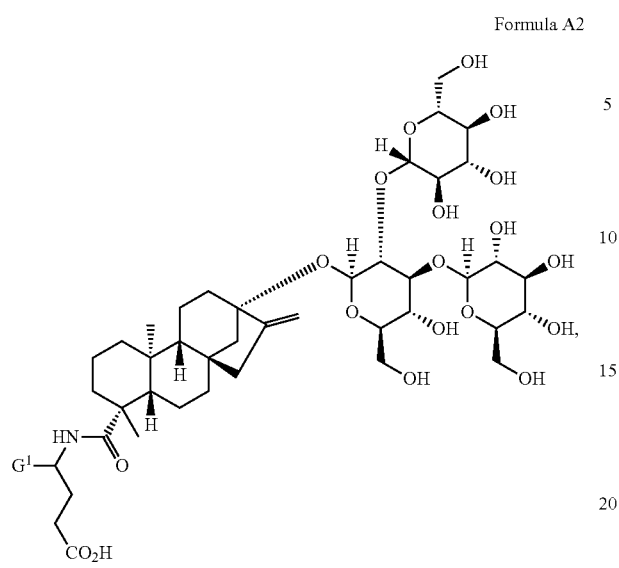
or a salt thereof.
14. The compound of claim 13, wherein $G^1$ is selected from the group consisting of:
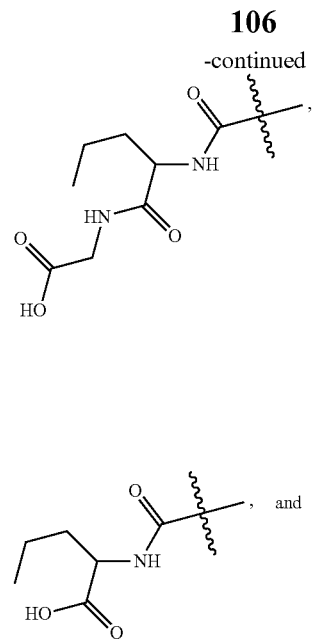
or a salt thereof.
15. The compound of claim 1, selected from the group consisting of
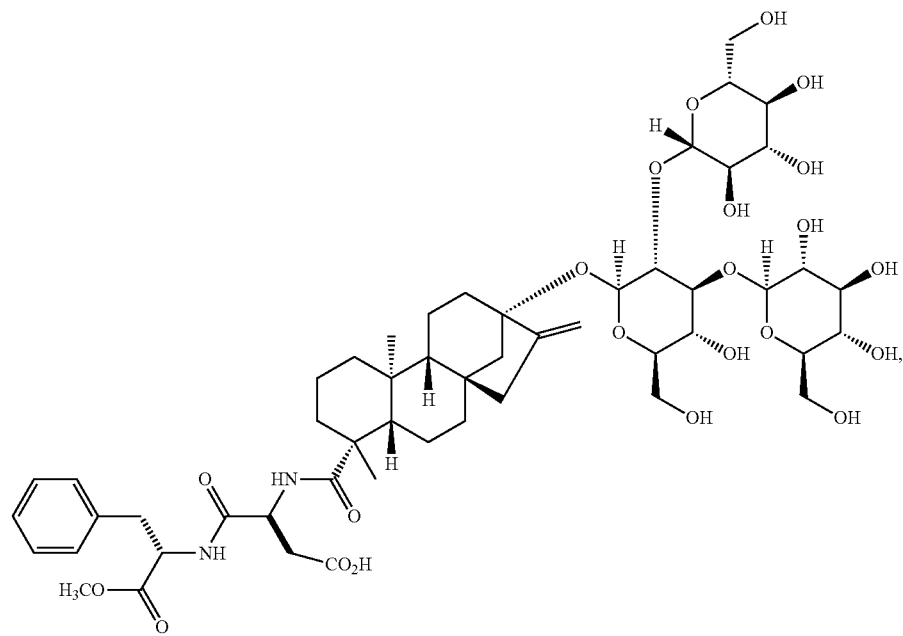

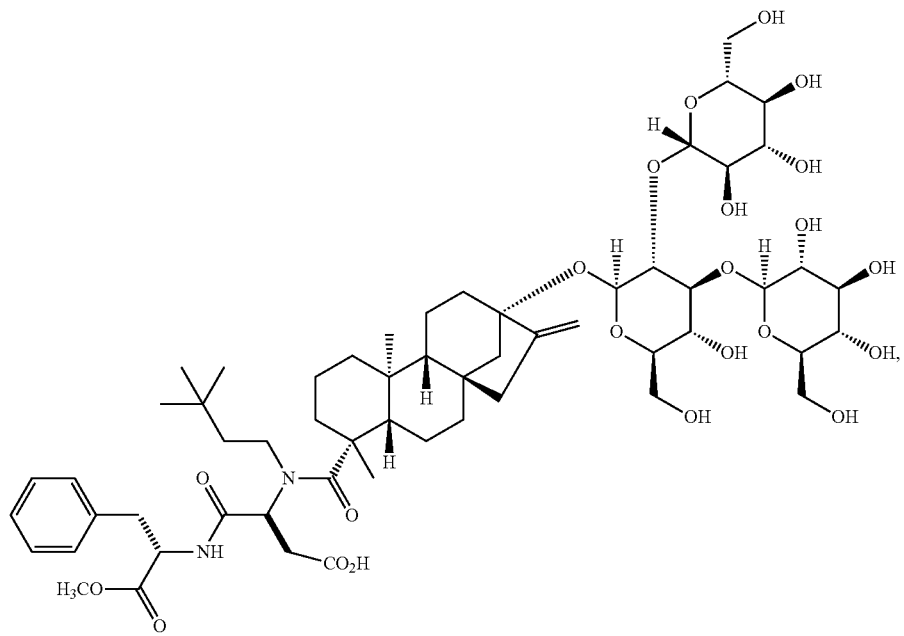
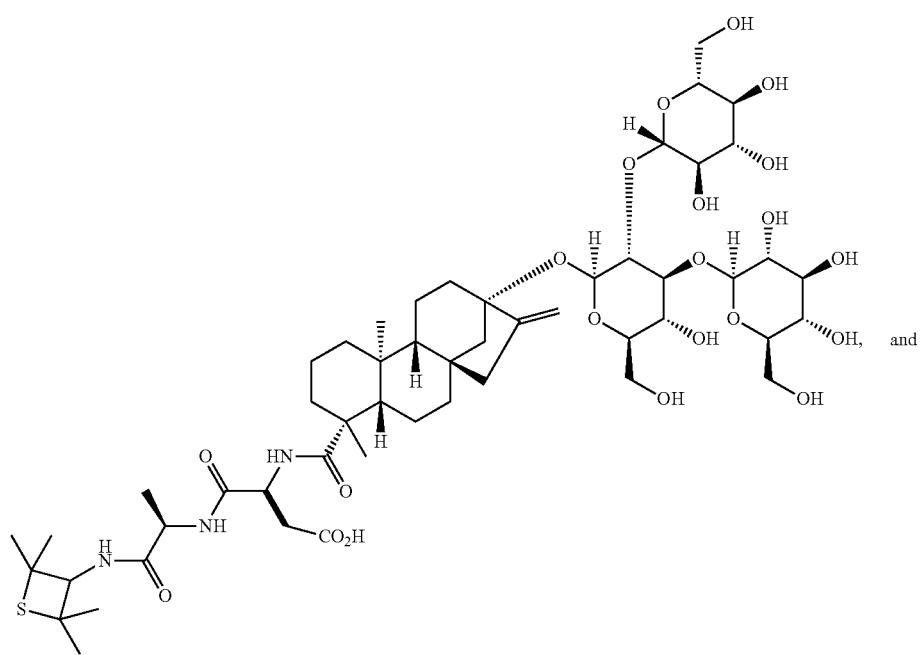

-continued

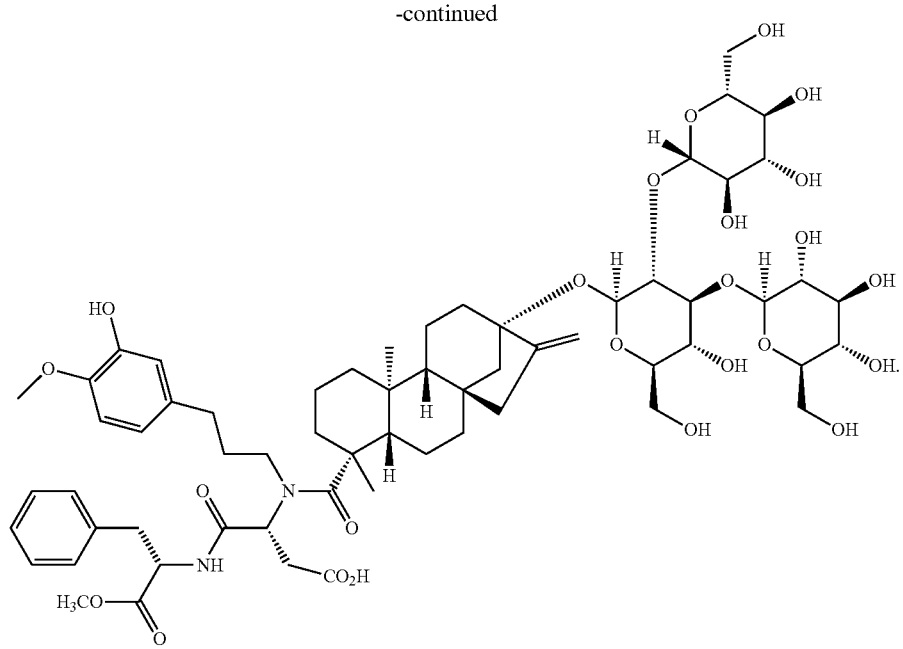

16. The compound:

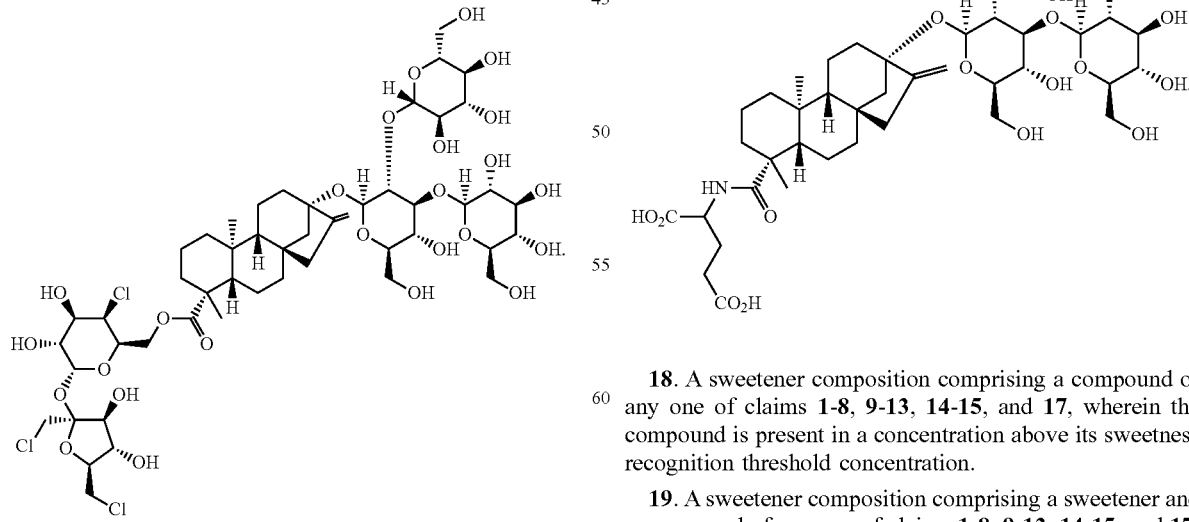

17. A compound having the formula

18. A sweetener composition comprising a compound of any one of claims 1-8, 9-13, 14-15, and 17, wherein the compound is present in a concentration above its sweetness recognition threshold concentration.

19. A sweetener composition comprising a sweetener and a compound of any one of claims 1-8, 9-13, 14-15, and 17, wherein the compound is present in a concentration sufficient to further enhance the sweetness of the sweetener but in a concentration below the compound's sweetness recognition threshold concentration.

20. The sweetener composition of claim 19, wherein the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof.

21. A beverage product comprising a compound of any one of claims 1-8, 9-13, 14-15, and 17.

22. A food product comprising a food component and a compound of any one of claims 1-8, 9-13, 14-15, and 17.

23. A method of reducing the amount of sweetener in a food product or a beverage product, comprising replacing at least a portion of the sweetener in the food or beverage product with a compound of any one of claims 1-8, 9-13, 14-15, and 17.

* * * * *